US006187792B1

(12) United States Patent
Delorme et al.

(10) Patent No.: US 6,187,792 B1
(45) Date of Patent: Feb. 13, 2001

(54) COMPOUNDS WITH ANALGESIC EFFECT

(75) Inventors: Daniel Delorme, St. Lazare; Edward Roberts, St. Lazare de Vaudreuil; Zhongyong Wei, Pierrefonds, all of (CA)

(73) Assignee: Astra Pharma Inc. (CA)

( * ) Notice: Under 35 U.S.C. 154(b), the term of this patent shall be extended for 0 days.

(21) Appl. No.: 09/029,633

(22) PCT Filed: Dec. 9, 1997

(86) PCT No.: PCT/SE97/02050

§ 371 Date: Mar. 5, 1998

§ 102(e) Date: Mar. 5, 1998

(87) PCT Pub. No.: WO98/28275

PCT Pub. Date: Jul. 2, 1998

(30) Foreign Application Priority Data

Dec. 20, 1996 (SE) .................................................. 9604785
Jul. 1, 1997 (SE) .................................................. 9702535

(51) Int. Cl.$^7$ ..................... A61K 31/445; C07D 307/81; C07D 211/70
(52) U.S. Cl. ..................... 514/320; 514/314; 514/319; 514/326; 514/331; 546/22; 546/152; 546/197; 546/205; 546/213; 546/229; 546/232; 546/234
(58) Field of Search ..................... 514/314, 319, 514/320, 326, 331; 546/22, 152, 197, 205, 213, 229, 232, 234

(56) References Cited

U.S. PATENT DOCUMENTS

| 2,898,339 |   | 8/1959 | Wheeler et al. ..................... 546/194 |
| 4,581,171 | * | 4/1986 | Kennis ..................... 514/258 |
| 4,939,137 | * | 7/1990 | Russell ..................... 514/183 |
| 5,140,029 | * | 8/1992 | Kennis ..................... 514/272 |
| 5,574,159 | * | 11/1996 | Chang ..................... 544/396 |
| 5,683,998 | * | 11/1997 | Shibayama ..................... 514/218 |

FOREIGN PATENT DOCUMENTS

WO 93/15062   8/1993  (WO) ........................ C07D/241/04

OTHER PUBLICATIONS

Greene "Protective groups in organic synthesis" Wiley& Sons, p.218–220,232,233,251, 1982.*
Barber, et al., "Antinociceptive Effects of the 5–HT$_2$ Antagonist Ritanserin in Rats: Evidence for an Activation of Descending Monoaminergic Pathways in the Spinal Cord," *Neurosci. Letters* 99:234–238 (1989).
Takemori, et al., "Selective Natrexone–Derived Opinoid Receptor Antagonists," *Annu. Ref. Pharmacol. Toxicol.* 32:239–269 (1992).

* cited by examiner

*Primary Examiner*—Ceila Chang
(74) *Attorney, Agent, or Firm*—Michael A. Sanzo; Pillsbury Madison & Sutro LLP

(57) ABSTRACT

Compounds of general formula (I)

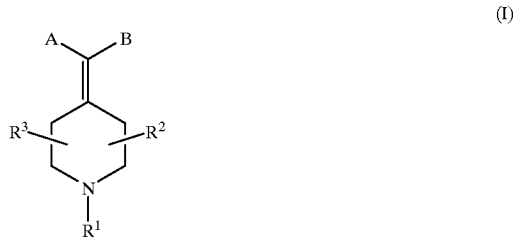

are disclosed and claimed in the present application, as well as their pharmaceutically acceptable salts, pharmaceutical compositions comprising the novel compounds and their use in therapy, in particular in the management of pain.

14 Claims, No Drawings

COMPOUNDS WITH ANALGESIC EFFECT

CROSS REFERENCE TO RELATED APPLICATIONS

The present application represents U.S. national stage of international application PCT/SE97/02050, filed Dec. 9, 1997. The international application claims priority to Swedish applications filed on Dec. 20,1996 (application 9604785-7) and on Jul. 1,1997 plication 9702535-7).

FIELD OF THE INVENTION

The present invention is related to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. Some non-peptidic δ antagonists have been available for some time (see Takemori and Portoghese, 1992, Ann. Rev. Pharmacol. Tox., 32: 239–269. for review). These compounds, e.g. naltrindole, suffer from rather poor (i.e., <10-fold) selectivity for the δ receptor vs. μ receptor binding and exhibit no analgesic activity, a fact which underscores the need for the development of highly selective non-peptidic δ ligands.

Thus, the problem underlying the present invention was to find new compounds having improved analgesic effects, but also with an improved side-effect profile over current μ agonists and potential oral efficacy.

Analgesics that have been identified and are existing in the prior art have many disadvantages such as that they suffer from poor pharmacokinetics and are not analgesic when administered by systemic routes. Also, it has been documented that preferred compounds, described within the prior art, show significant convulsive effects when administered systemically.

The problem mentioned above has been solved by developing novel compounds which possess a piperidine ring with an exocyclic double bond, as will be described below.

Outline of the Invention

The novel compounds according to the present invention are defined by the general formula (I)

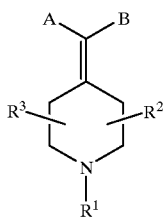

wherein $R^1$ is selected from hydrogen, a branched or straight $C_1$–$C_6$ alkyl, $C_1$–$C_6$ alkenyl, $C_3$–$C_8$ cycloalkyl, $C_4$–$C_8$(alkyl-cycloalkyl) wherein alkyl is $C_1$–$C_2$ alkyl and cycloalkyl is $C_3$–$C_6$ cycloalkyl;

$C_6$–$C_{10}$ aryl; or heteroaryl having from 5 to 10 atoms selected from any of C, S, N and O;

wherein the aryl and heteroaryl may optionally and independently be substituted by 1 or 2 substituents independently selected from any of hydrogen, $CH_3$, —$(CH_2)_pCF_3$, halogen, —$CONR^5R^4$, —$COOR^5$, —$COR^5$, —$(CH_2)_pNR^5R^4$, —$(CH_2)_pCH_3(CH_2)_pSOR^5R^4$, —$(CH_2)_pSO_2R^5$, and —$(CH_2)_pSO_2NR^5$, wherein $R^4$ and $R^5$ is each and independently as defined for $R^1$ above and p is 0, 1 or 2;

($C_1$–$C_2$ alkyl)–($C_6$–$C_{10}$ aryl); or ($C_1$–$C_2$ alkyl)heteroaryl, the heteroaryl moieties having from 5 to 10 atoms selected from any of C, S, N and , and where the aryl or heteroaryl may optionally and independently be substituted by 1 or 2 substituents independently selected from any of hydrogen, $CH_3$, —$(CH_2)_qCF_3$, halogen, —$CONR^5R^4$, —$COOR^5$, —$COR^5$, —$(CH_2)_qNR^5R^4$, —$(CH_2)_qCH_3(CH_2)_qSOR^5R^4$, —$(CH_2)_qSO_2R^5$, —$(CH_2)_qSO_2NR^5$ and —$(CH_2)_pOR^5$, wherein $R^4$ and $R^5$ is each and independently as defined for $R^1$ above and q is 0, 1 or 2; and

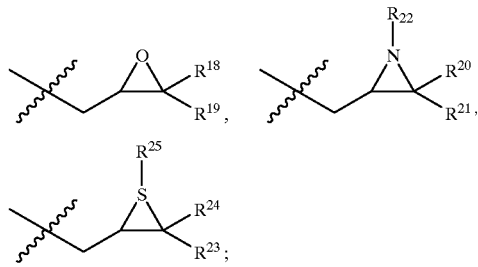

wherein $R^{18}$, $R^{19}$, $R^{20}$, $R^{21}$, $R^{22}$, $R^{23}$, $R^{24}$ and $R^{25}$ is each and independently hydrogen, $C_1$–$C_6$ alkyl or $C_1$–$C_6$ alkenyl;

$R^2$ and $R^3$ is each and independently hydrogen or $C_1$–$C_6$ alkyl;

A is selected from

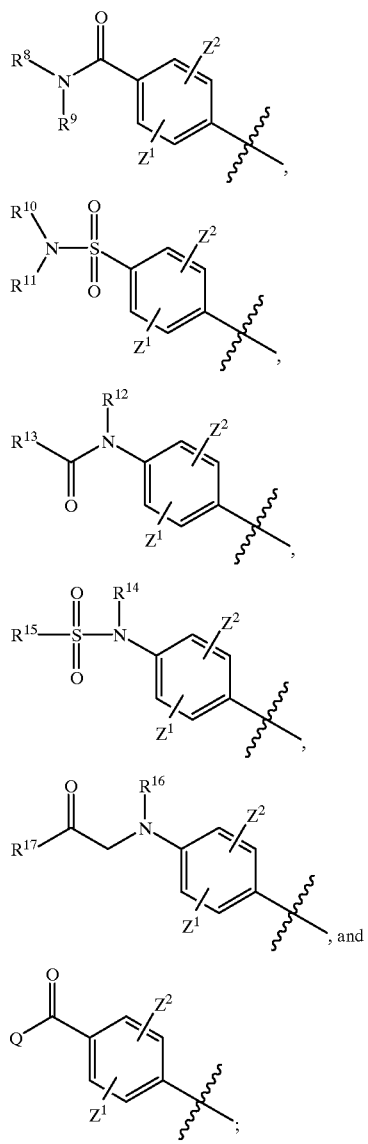

wherein $R^8$, $R^9$, $R^{10}$, $R^{11}$, $R^{12}$, $R^{13}$, $R^{14}$, $R^{15}$, $R^{16}$ and $R^{17}$ is each and independently as defined for $R^1$ above, and wherein the phenyl ring of each A substituent may be optionally and independently substituted at any position of the phenyl ring by 1 or 2 substituents $Z^1$ and $Z^2$ which are each and independently selected from hydrogen, $CH_3$, —$(CH_2)_qCF_3$, halogen, —$CONR^6R^7$, —$COOR6$, —$COR^6$, —$(CH_2)_rNR^6R^7$, —$(CH_2)_rCH_3(CH_2)_rSOR^6$, —$(CH_2)_rSO_2R^6$ and —$(CH_2)_rSO_2NR^6R^7$ wherein $R^6$ and $R^7$ is each and independently as defined for $R^1$ above and r is 0, 1, or 2;

Q is $C_5$–$C_6$ hydroaryl or heterohydroaromatic having 5 or 6 atoms selected from anyone of C, S, N and O; $C_5$–$C_6$ cykloalkyl, or heterocycloalkyl having 5 or 6 atoms selected from anyone of C, N, O and S; and where each Q may optionally be substituted by a substituent $Z^1$ and $Z^2$ as defined above;

B is a substituted or unsubstituted aromatic, heteroaromatic, hydroaromatic or heterohydroaromatic moiety having from 5 to 10 atoms selected from any of C, S, N and O, optionally and independently substituted by 1 or 2 substituents independently selected from hydrogen, $CH_3$, —$(CH_2)_tCF_3$, halogen, —$(CH_2)_tCONR^5R^4$, —$(CH_2)_tNR^5R^4$, —$(CH_2)_tCOR^5$, —$(CH_2)_tCOOR^5$, —$OR^5$, —$(CH_2)_tSOR^5$, —$(CH_2)_tSO_2R^5$, and —$(CH_2)_tSO_2NR^5R^4$, wherein $R^4$ and $R^5$ is each and independently as defined for $R^1$ above, and t is 0, 1, 2 or 3; and $R^4$ and $R^5$ is each and independently as defined for $R^1$ above.

Within the scope of the invention are also pharmaceutically acceptable salts of the compounds of the formula (I), as well as isomers, hydrates, isoforms and prodrugs thereof.

Preferred compounds according to the invention are compounds of the formula (I)
wherein
A is selected from

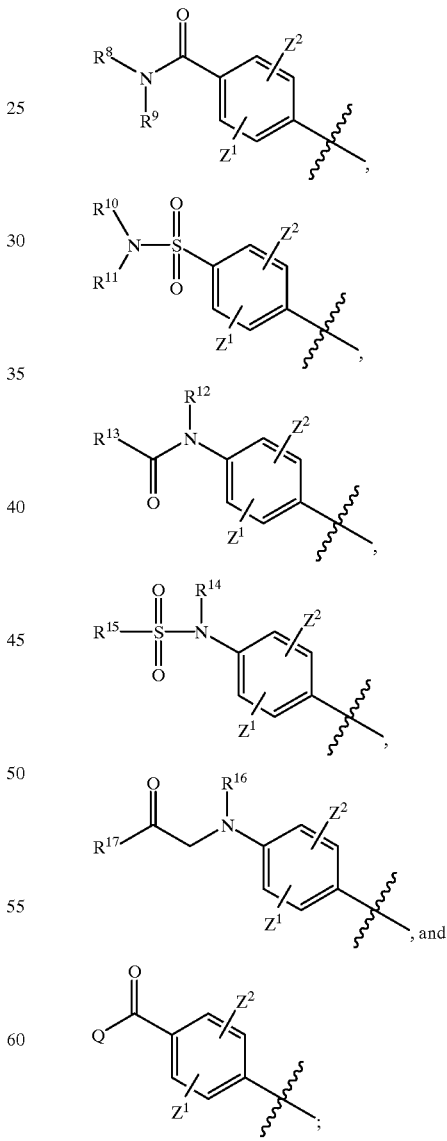

wherein $R^8$, $R^9$, $R^{10}$, $R^{11}$, $R^{12}$, $R^{13}$, $R^{14}$, $R^{15}$, $R^{16}$ and $R^{17}$ is each and independently as defined for $R^1$ above, and wherein the phenyl ring of each A substituent may be optionally and independently substituted at any position of the phenyl ring by 1 or 2 substituents $Z^1$ and $Z^2$ which are each and independently selected from hydrogen, $CH_3$, —$(CH_2)_qCF_3$, halogen, —$CONR^6R^7$, —$COOR^6$, —$COR^6$, —$(CH_2)_rNR^6R^7$, —$(CH_2)_rCH_3(CH_2)_rSOR^6$, —$(CH_2)_rSO_2R^6$ and —$(CH_2)_rSO_2NR^6R^7$ wherein $R^6$ and $R^7$ is each and independently as defined for $R^1$ above, and r is 0, 1, or 2;

Q is selected from morpholine, piperidine and pyrrolidine;

$R^1$, $R^4$, and $R^5$ is each and independently selected from hydrogen, a branched or straight $C_1$–$C_4$ alkyl, $C_3$–$C_5$ cycloalkyl, $C_4$–$C_8$ (alkyl-cycloalkyl) wherein alkyl is $C_1$–$C_2$ alkyl an cycloalkyl is $C_3$–$C_6$ cycloalkyl; $C_6$–$C_{10}$ aryl; and heteroaryl having from 5 to 6 atoms selected from any of C, S, N and O; and where the aryl or heteroaryl may optionally and independently be substituted by 1 or 2 substituents independently selected from any of hydrogen, $CH_3$, —$(CH_2)_pCF_3$, halogen, —$CONR^5R^4$, —$COOR^5$, —$COR^5$, —$(CH_2)_pNR^5R^4$, —$(CH_2)_pCH_3(CH_2)_pSOR^5R^4$, —$(CH_2)_pSO_2R^5$, and —$(CH_2)_pSO_2NR^5$, wherein $R^4$ and $R^5$ is each and independently as defined for $R^1$ above and p is 0, 1 or 2;

B is selected from phenyl, naphthyl, indolyl, benzofuranyl, dihydrobenzofuranyl, benzothiophenyl, pyrryl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, pyrrolidinyl, and indazolinyl, each optionally and independently substituted by 1 or 2 substituents independently selected from hydrogen, $CH_3$, $CF_3$, halogen, —$(CH_2)_qCONR^5R^4$, —$(CH_2)_qNR^5R^4$, —$(CH_2)_qCOR^5$, —$(CH_2)_qCO_2R^5$, and —$OR^5$, wherein q is 0 or 1, and wherein $R^4$ and $R^5$ are as defined above;

$R^2$ and $R^3$ is each and independently hydrogen or methyl.

Especially preferred compounds according to the invention are compounds of the formula (I) wherein A is

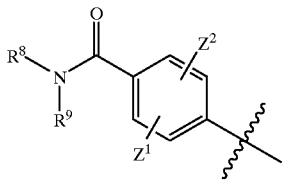

wherein $R^8$ and $R^9$ are both ethyl, and where the phenyl ring optionally and independently may be substituted at any position of the phenyl ring by 1 or 2 substituents $Z^1$ and $Z^2$ which are each and independently selected from hydrogen, $CH_3$, —$(CH_2)_qCF_3$, halogen, —$CONR^6R^7$, —$COOR^6$, —$COR^6$, —$(CH_2)_rNR^6R^7$, —$(CH_2)_rCH_3(CH_2)_rSOR^6$, —$(CH_2)_rSO_2R^6$ and —$(CH_2)_rSO_2NR^6R^7$ wherein $R^6$ and $R^7$ is each and independently as defined for $R^1$ above and r is 0, 1, or 2;

$R^1$ is selected from hydrogen, methyl, ethyl, —$CH_2CH=CH_2$, —$CH_2$-cyclopropyl, —$CH_2$—aryl, or $CH_2$-heteroaryl, the heteroaryl moieties having from 5 to 6 atoms selected from any of C, S, N and O;

B is selected from phenyl, naphthyl, indolyl, benzofuranyl, dihydrobenzofuranyl, benzothiophenyl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, and indazolinyl, each optionally and independently substituted by 1 or 2 substituents independently selected from hydrogen, $CH_3$, $CF_3$, halogen, —$(CH_2)_qCONR^5R^4$, —$(CH_2)_qNR^5R^4$, —$(CH_2)_qCOR^5$, —$(CH_2)_qCO_2R^5$, and —$OR^5$, wherein q is 0 or 1, and wherein $R^4$ and $R^5$ are as defined above;

$R^2$ and $R^3$ is each and independently hydrogen or methyl.

The substituents A and B respectively, may optionally be substituted at any position of the ring.

By "halogen" we mean chloro, fluoro, bromo and iodo.

By "aryl" we mean an aromatic ring having from 6 to 10 carbon atoms, such as phenyl and naphtyl.

By "heteroaryl" we mean an aromatic ring in which one or more of the from 5–10 atoms in the ring are elements other than carbon, such as N, S and O.

By "hydroaromatic" we mean a partly or fully saturated aromatic ring structure having 5–10 carbon atoms in the ring.

By "heterohydroaromatic" we mean a partly or fully saturated aromatic ring structure in which one or more of the 5–10 atoms in the ring are elements other than carbon, such as N, S and O.

By "isomers" we mean compounds of the formula (I), which differ by the position of their functional group and/or orientation. By "orientation" we mean stereoisomers, diastereoisomers, regioisomers and enantiomers.

By "isoforms" we mean compounds of the formula (I) which differ by their crystal lattice, such as crystalline compound and amorphous compounds.

By "prodrug" we mean pharmacologically acceptable derivatives, e.g. esters and amides, such that the resulting biotransformation product of the derivative is the active drug. The reference by Goodman and Gilmans, The Pharmacological basis of Therapeutics, 8th ed., McGraw-Hill, Int. Ed. 1992, "Biotransformation of Drugs, p. 13–15, describing prodrugs generally, is hereby incorporated.

The novel compounds of the present invention are useful in therapy, especially for the treatment of various pain conditions such as chronic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (eg. Amnesia, analgesia, muscle relaxation and sedation). Included in this combination are inhaled anaesthetics, hypnotica, anxiolytics, neuromuscular blockers and opioids.

The compounds of the present invention in isotopically labelled form are useful as a diagnostic agent.

Also within the scope of the invention is the use of any of the compounds according to the formula (I) above, for the manufacture of a medicament for the treatment of any of the conditions discussed above.

A further aspect of the invention is a method for the treatment of a subject suffering from any of the conditions discussed above, whereby an effective amount of a compound according to the formula (I) above, is administered to a patient in need of such treatment.

Methods of Preparation

The compounds of the present invention may be prepared as described in the following.

SCHEME I

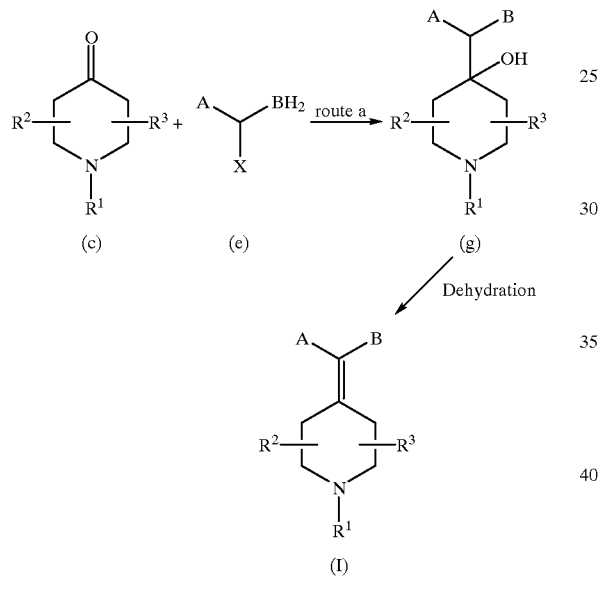

SCHEME II

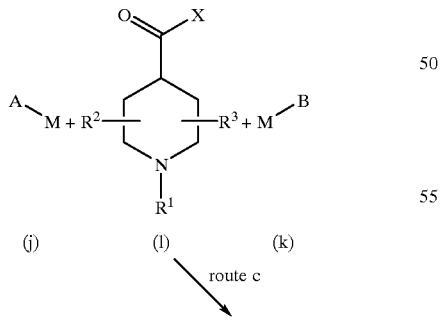

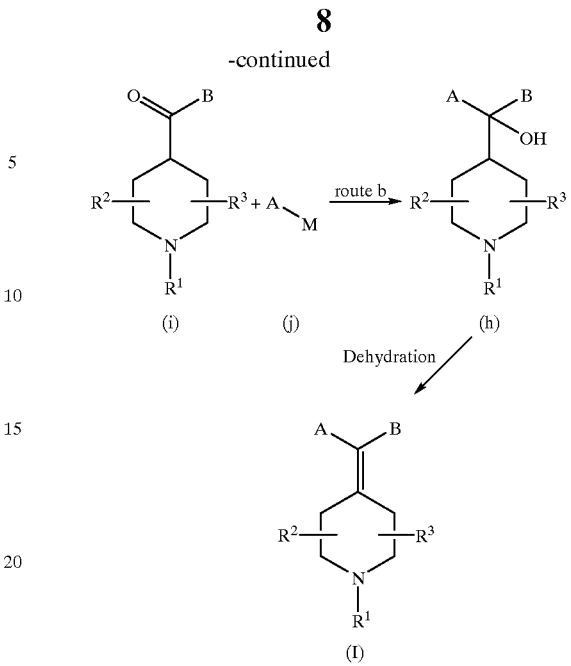

SCHEME III

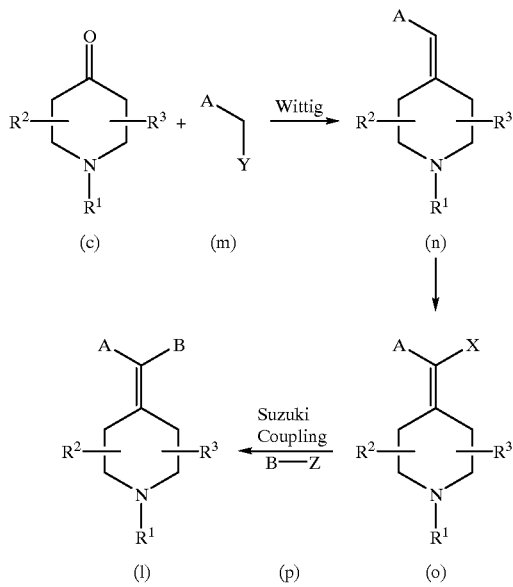

SCHEME IV

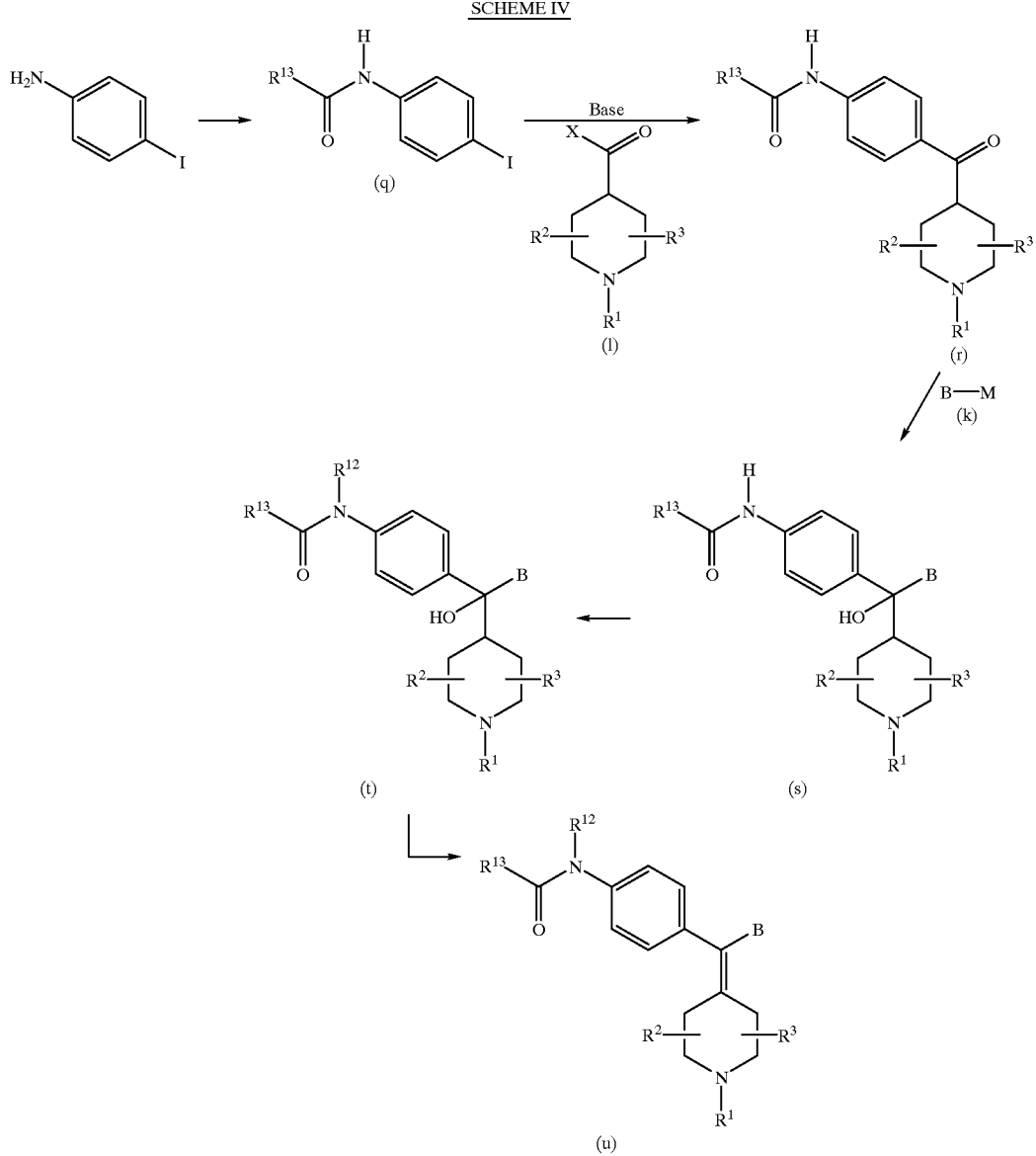

As shown in SCHEME I & II above, compounds of the formula (I) above, may be obtained by dehydration of hydroxy compounds (g) or (h), wherein $R^1$, $R^2$, $R^3$, A and B are as defined in formula (I) above. Subsequent dehydration of hydroxyl compounds (g) or (h), wherein $R^1$, $R^2$, $R^3$, A and B are as defined in formula (I), may be performed without solvents or in a solvent such as water, alcohols, esters, HMPA, dichloromethane, toluene, ethers, ketones, carboxylic acids or in a solvent mixture in the presence of Bronstedt or Lewis acids such as sulphuric acid, hydrochloric acid, trifluoroacetic acid, aluminium trichloride, $ZnCl_2$ or the like, or in the presence of metallic oxides such as $Al_2O_3$, $Cr_2O_3$, $TiO_2$, $WO_3$, $P_2O_5$ or the like, or in the presence of other dehydrating agents such as $I_2$, dimethyl sulfoxide, KHSO4, $CuSO_4$, phthalic anhydride or the like.

The substituents $R^1$, $R^2$ and $R^3$ and the substituents on A and B of compound (I), as defined above, may be modified by methods known in the art and exemplfied in the literature, see e.g. *Protecting groups* by Green, or *Modern Synthetic Reactions* by House, which are well known to a person skilled in the art, after or during the preparation of (I) from (g) and (h).

As shown the route a of SCHEME I, compounds of formula (g), as described above, may be obtained by a reaction between a ketone of formula (c) wherein $R^1$, $R^2$ and $R^3$ are as defined in formula (I), and a compound of formula (e) wherein A and B are as defined in formula (I), and X is a suitable group such as H, Cl, Br, I, $OSO_2R$ or the like The reaction may be performed without solvents, or in an organic solvent such as THF, toluene, ethers, dimethylsulfoxide, or in solvent mixtures by treatment with an appropriate metal such as magnesium, lithium, zinc, copper, cerium or the like, or by treatment with a metal halide such as $SmI_2$, $CrCl_2$ or the like, or by treatment with an organometallic agents such as alkylmagnesium halides, alkyllithium or the like.

$R^1$, $R^2$ and $R^3$ and the substituents on A and B of compounds (g), as defined above, may be modified, by methods known in the art, after or during the organometallic reactions (March, J., *Advanced Organic Chemistry*, 4$^{th}$ Ed, John Wiley & Sons, 1992).

Compounds of formula (c) and (e) may be commercially available, or prepared by methods known in the art (March, J., *Advanced Organic Chemistry*, 4$^{th}$ Ed, John Wiley & Sons, 1992).

As shown in route b of SCHEME II, compounds of formula (h), as described above, may be obtained by a reaction between a ketone of formula (i) wherein $R^1$, $R^2$ and $R^3$, and B are as defined in formula (I), and an organometallic reagent of formula (j) wherein A is as defined in formula (I), and M is an appropriate metal group such as magnesium, lithium, zinc, copper, cerium or the like. The reaction may be performed without solvents, or in an organic solvent such as THF, toluene, ethers, dimethylsulfoxide, or in solvent mixtures.

As shown in route c of SCHEME II, compounds of formula (h) may also be obtained by reactions among a carbonyl compound of formula (I), wherein $R^1$, $R^2$ and $R^3$ are as defined in formula (I), and X is an appropriate leaving group such as Cl, Br, OH, OR, SR, $NR_2$, N(OR')R or the like, and organometallic reagents of formula (j) and (k), wherein A and B are as defined in formula (I), and M is an appropriate metal group such as magnesium, lithium, zinc, copper, cerium or the like. The reactions may be performed without solvents or in solvents such as THF, toluene, ethers, dimethyl formamide, dioxane, dimethylsulfoxide, or in solvent mixtures.

$R^1$, $R^2$ and $R^3$ and the substituents on A and B of compounds (h), as defined above, may be modified, by methods known in the art and exemplfied in the literature, see e.g. *Protecting groups* by Green, or *Modern Synthetic Reactions* by House, which are well known to a person skilled in the art, after or during the organometallic reactions.

Compounds of formula (i), (j), (k) and (l) may be commercially available, or prepared by methods known in the art (March, J., *Advanced Organic Chemistry*, 4$^{th}$ Ed, John Wiley & Sons, 1992).

As shown in SCHEME III above, compounds of the formula (I) above, may be obtained from the Suzuki coupling of vinylic halide (o) (X=Br, I) with a boronic acid, boronate ester (p), in the presence of a base such as $Na_2CO_3$, $K_2CO_3$, $K_3PO_4$, triethylamine, CsF, NaOH or alkoxides and palladium catalyst such as $(PPh_3)_4Pd$, Bis (dibenzylideneacetone)Pd(0), Pd on carbon with $PPh_3$; Pd(II) species may also be used as a catalyst including: $(PPh_3)_2PdCl_2$, 1,4-Bis(diphenylphosphinobutane)palladium (II) chloride, Palladium acetate, Bis(acetonitrile)palladium (II) chloride, dichloro[1,1'-bis(diphenylphosphino) ferrocene] palladium(II) and palladium acetate-tri(O-tolyl) phosphine, wherein $R^1$, $R^2$, $R^3$, A and B are as defined in formula (I) above. The Suzuki coupling may be performed in toluene, xylene, anisole, DMF, THF, alcohols, ethers, water or in a solvent mixture.

Compounds or formula (p), where B is as defined in formula (I) and Z is $B(OH)_2$, may be commercially available or prepared from the hydrolysis of a boronate ester. Compounds or formula (p), where B is as defined in formula (I) and Z is $B(OR)_2$ (R=Me, Et), may be prepared from the reaction of a compound of formula B-M and $B(OR)_3$ where R=Me or Et, and M is an appropriate metal group such as lithium or magnesium or the like. Compounds of formula (p) where B is as defined in formula (I) and Z is 9-borabicyclo [3.3.1]nonane (9-BBN) may be prepared from the reaction of an alk-1-yne with borabicyclo[3.3.1]nonane.

The substituents $R^1$, $R^2$, $R^3$ and the substituents on A and B of compound (I) as defined above, may be modified by methods known in the art and exemplified in the literature, see e.g. *Protecting groups* by Green or *Modern Synthetic Reactions* by House, which are well known to a person skilled in the art, after or during the preparation of (I) from (o) and (p).

As shown in SCHEME III, compounds of formula (o) wherein X is Br or I, may be prepared from the halogenation and elimination of an alkene of formula (n) wherein $R^1$, $R^2$, $R^3$ and A are as defined in formula (I). The halogenation may be performed in a solvent such as dichloromethane, chloroform, carbon tetrachloride, dichloroethane, or acetic acid using molecular bromine or iodine as halogenation agent. The subsequent elimination step is accomplished in a solvent such as water, alcohols, DMF, or ethers using a base such as sodium hydroxide, potassium hydroxide, metal alkoxides, or triethylamine.

As shown in SCHEME III, compounds of formula (n), as described above, may be prepared from the Wittig reaction of a ketone of formula (c), where $R^1$, $R^2$ and $R^3$ are as defined in formula (I), and a reagent of formula (m) where A is as defined in formula (I) and Y is an appropriate phosphonate or phosphonium salt. The Wittig reaction may be carried out under a variety of conditions known in the art and exemplified in the literature (March, J., *Advanced Organic Chemistry*, 4$^{th}$ Ed., John Wiley & Sons, 1992).

Reagents of formula (c) and (m) may be commercially available, or prepared by methods known in the art (March, J., *Advanced Organic Chemistry*, 4$^{th}$ Ed., John Wiley & Sons, 1992).

As shown in SCHEME IV above, compounds of formula (u) may be obtained by dehydration of hydroxy compound (t) wherein $R^1,R^2,R^3,R^{12},R^{13}$ and B are as defined above. Dehydration step may be performed without solvent or in a solvent such as water, alcohols, esters, HMPA, dichloromethane, toluene, ethers, ketones, carboxylic acids, or in a solvent mixture in the presence of Bronstedt or Lewis acids such as sulfuric acid, hydrochloric acid, trifluoroacetic acid, aluminium trichloride, $ZnCl_2$, or the like, or in the presence of metallic oxides such as $Al_2O_3$, $Cr_2O_3$, $TiO_2$, $WO_3$, $P_2O_5$ or the like, or presence of other dehydrating agents such as $I_2$, dimethylsulfoxide, $KHSO_4$, $CuSO_4$, phthalic anhydride or the like.

The substituents $R^1,R^2$ and $R^3$ and the substituent B of compound (u) as defined above may be modified by methods known in the art and exemplified in the literature, see e.g. *Protecting Groups* by Green, or *Modern Synthetic Reactions* by House, which are well known to a person skilled in the art, after or during the preparation of (u) from (t).

As shown in SCHEME IV above, compounds of formula (t) may be obtained from compound (s) wherein $R^1,R^2,R^3$, $R^{13}$ and B are as defined above using alkylation reaction with alkyl halide such as MeI in presence of a base such as sodium hydroxide and a phase transfer agent such as $Bu_4NHSO_4$. Compounds of formula (s) may be prepared by a reaction between a ketone of formula (r) wherein $R^1,R^2$, $R^3,R^{13}$ are as defined above and an organometallic reagent of formula (k) wherein B is defined in formula (I) and M is an appropriate metal group such as magnesium, lithium, zinc, copper, cerium, or the like. The reaction may be performed without solvent or in solvents such as THF, toluene, ethers, dimethylformamide, dioxane, dimethylsufoxide, or in solvent mixtures.

The substituents $R^1,R^2,R^3,R^{13}$ of compound (s) as defined above may be modified by methods known in the art and exemplified in the literature, see e.g. *Protecting Groups* by Green, or *Modern Synthetic Reactions* by House, which are well known to a person skilled in the art, after or during the preparation of (s) from (r) and (k).

As shown in SCHEME IV, a compound of formula (r) may be obtained by reactions among a carbonyl compound of formula (I) wherein $R^1$, $R^2$ and $R^3$ are as defined in formula (I) and X is an appropriate leaving group such as Cl, Br, OH, OR, SR, $NR_2$, $N(OR^1)R$ or the like and organometallic reagent obtained by first base treatment such as NaH on compound (q) wherein $R^{13}$ is as defined above followed by subsequent transmetallation using alkyl lithium such as Buli. The reaction may be performed in solvents such as THF, toluene, ethers, dimethylformamide, dioxane, or in solvent mixtures. The substituents $R^1, R^2, R^3, R^{13}$ of compound (r) as defined above may be modified by methods known in the art and exemplified in the literature, see e.g. *Protecting Groups* by Green, or *Modern Synthetic Reactions* by House, which are well known to a person skilled in the art, after or during the preparation of (r) from (q) and (l).

As shown in SCHEME IV, compounds of formula (q) may be obtained by acylation of 4-iodoaniline using either acylanhydride or acylchloride in an organic solvent such as dichloromethane. The substituent $R^{13}$ of compound (q) is as defined above.

The invention will now be described in more detail by way of the following Examples, which are not to be construed as limiting the invention in any way.

A) Synthetic Scheme for the Preparation of the Compounds of Examples 1–7

The compounds of Examples 1–7 were prepared by following the procedure as is shown in Scheme 1 below.

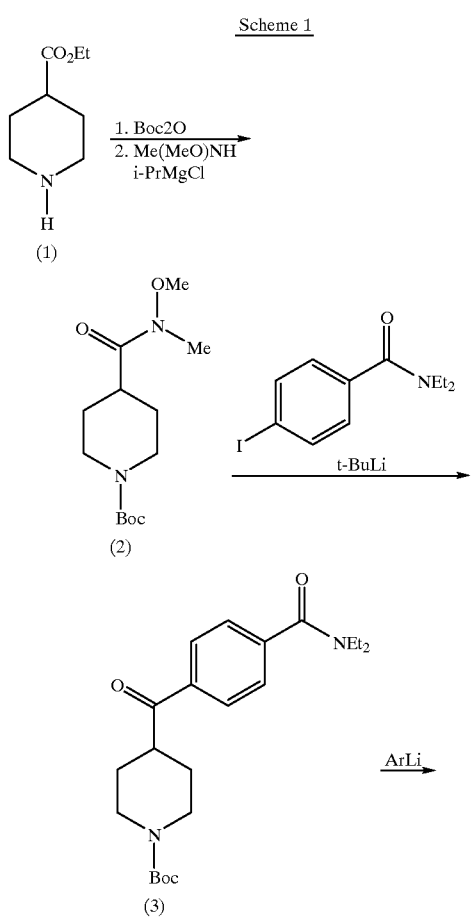

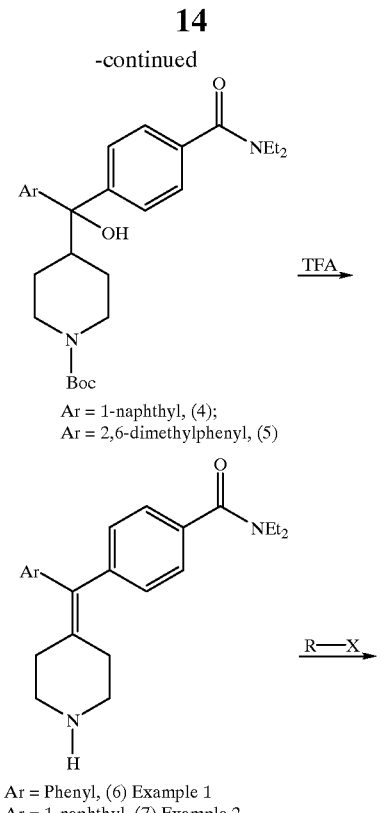

Ar = 1-naphthyl, (4);
Ar = 2,6-dimethylphenyl, (5)

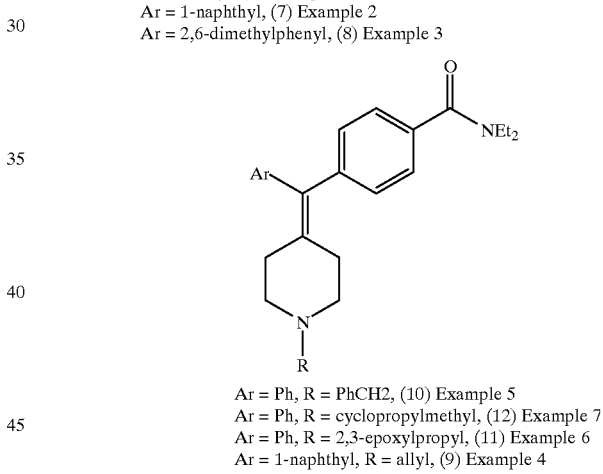

Ar = Phenyl, (6) Example 1
Ar = 1-naphthyl, (7) Example 2
Ar = 2,6-dimethylphenyl, (8) Example 3

Ar = Ph, R = PhCH2, (10) Example 5
Ar = Ph, R = cyclopropylmethyl, (12) Example 7
Ar = Ph, R = 2,3-epoxylpropyl, (11) Example 6
Ar = 1-naphthyl, R = allyl, (9) Example 4

(i) Preparation of N-t-Butoxylcarbonyl N'-methyl-N'-methoxyl-isonipecotamide (compound 2)

A mixture of ethyl isonipecotate (compound 1) (4.71 g, 30.0 mmol), di-tert-butyl dicarbonate (6.55 g, 30.0 mmol) and $Na_2CO_3$ (4.77 g, 45 mmol) in $H_2O$-THF (90/10 mL) was refluxed for 2 h. The reaction mixture was extracted with ethyl acetate (150 mL). The organic layer was washed with brine, dried over $MgSO_4$. Removal of solvents gave N-t-butoxylcarbonyl ethyl isonipecotate (7.67 g):

$\delta_H$(400 MHz, $CDCl_3$) 1.25 (t, J=7.2 Hz, 3H), 1.45 (s, 9H), 1.62 (m, 2H), 1.87 (m, 2H), 2.43 (m, 1H), 2.84 (m, 2H), 4.02 (m, 2H), 4.13 (q, J=7.2 Hz, 2H); $\delta_{C-13}$ (100 MHz, $CDCl_3$) δ: 14.0, 27.8, 28.2, 40.9, 42.9, 60.2, 79.2, 154.4, 174.2.

The above N-t-butoxylcarbonyl ethyl isonipecotate was dissolved in dry THF (60 mL) and mixed with NHMe(OMe) HCl (4.39 g, 45.0 mmol). The mixture was treated with i-PrMgCl (2.0 M in THF, 45 ml, 90 mmol) at −20° C. and the resulting solution was stirred for 1 hr at −5° C. and then quenched with aqueous NH$_4$Cl solution and extracted with ethyl acetate (2×100 mL). The combined organic layers were washed with brine, dried over MgSO$_4$. Removal of solvents gave N-t-butoxylcarbonyl N'-methyl-N'-methoxyl-isonipecotamide (compound 2) (8.0 g, 98%):

δ$_H$(400 MHz, CDCl$_3$) 1.30 (s, 9H), 1.54 (m, 4H), 2.65 (m, 3H), 3.02 (s, 3H), 3.56 (s,3H), 3.99 (brs, 2H); δ$_{C-13}$ (100 MHz, CDCl$_3$) δ: 27.7, 28.1, 32.0, 37.8, 43.1, 61.3, 79.1, 154.4, 176.0.

(ii) Preperation of 4-(4'-N',N'-Diethylaminocarbonylbenzoyl)-N-t-butoxylcarbonylpiperidine (compound 3)

To a solution of 4-iodo-N,N-diethylbenzamide (9.09 g, 30.0 mmol) and TMEDA (6.96 g, 60.0 mmol) in dry THF (60 mL) was added t-butyllithium (35.0 mL, 1.7 M, 60.0 mmol) at −78° C. After 30 min, N-t-butoxylcarbonyl N'-methyl-N'-methoxyl-isonipecotamide (compound 2) (8.0 g, 29.4 mmol) in THF (10 mL) was dropwise added. The reaction mixture was warmed to r.t. and then quenched with aqueous NH$_4$Cl solution, neutralized with hydrochloric acid (concentrated, 20 mL) at 0° C., and extracted with ethyl acetate (2×100 mL). The combined organic layers were washed with brine, dried over MgSO$_4$. Removal of solvents gave a crude product, which was purified by silica gel column eluting with MeOH—CH$_2$Cl$_2$ (2:98) to provide 4-(4'-N',N'-diethylaminocarbonylbenzoyl)-N-t-butoxylcarbonylpiperidine (compound 3) (3.15 g, 28%):

δ$_H$(400 MHz, CDCl$_3$) 1.08 (brs, 3H), 1.23 (brs, 3H), 1.43 (s, 9H), 1.61 (m, 2H), 1.80 (m, 2H), 2.89 (m, 2H), 3.20 (brs, 2H), 3.40 (m, 1H), 3.53 (brs, 2H), 4.11 (brs, 2H), 7.44 (d, J=8.0 Hz, 2H), 7.94 (d, J=8.0 Hz, 2H).

(iii) Preparation of 4-(α-Hydroxyl-α-(4-N-t-butoxylcarbonylpiperidinyl)-α-(1-naphthyl)-methyl)-N,N-diethylbenzamide (compound 4)

To a solution of 1-bromonaphthalene (0.52 g, 2.5 mml) in dry THF (10 mL) was added n-butyllithium (1.1 mL, 2.5 M, 2.75 mmol) at −78° C. After 30 min, 4-(4'-N',N'-diethylaminocarbonylbenzoyl)-N-t-butoxylcarbonylpiperidine (compound 3) (776 mg, 2.0 mmol) in THF (2 mL) was dropwise added. The reaction mixture was warmed to r.t. and then quenched with aqueous NH$_4$Cl solution, and extracted with ethyl acetate (2×50 mL). The combined organic layers were washed with brine, dried over MgSO$_4$. Removal of solvents gave a crude product, which was purified by silica gel column eluting with MeOH—CH$_2$Cl$_2$ (0.5:99.5→5:95) to provide 4-(α-hydroxyl-α-( 4-N-t-butoxylcarbonylpiperidinyl)-α-(1-naphthyl)-methyl)-N,N-diethylbenzamide (compound 4) (760 mg, 74%):

m.p. 121–124° C. (CH$_2$Cl$_2$); ν$_{max}$ (KBr) cm$^{-1}$ 3402, 2960,1685, 1626, 1425, 1283, 1160;

Anal.Calcd.for C$_{32}$H$_{40}$N$_2$O$_4$. 0.50H$_2$O: C, 73.11; H, 7.86; N, 5.33. Found: C, 72.86; H, 7.64; N, 5.26; δ$_H$(400 MHz, CDCl$_3$) 1.03 (brs, 3H), 1.16 (brs, 3H), 1.18–1.35 (m, 3H), 1.95 (m, 1H), 2.60 (m, 2H), 2.75 (brs, 2H), 3.15 (brs, 2H), 3.42 (brs, 2H), 4.10 (brs, 2H), 7.10–7.50 (m, 7H), 7.75 (m, 3H), 8.27 (brs, 1H); δ$_{C-13}$ (100 MHz, CDCl$_3$) δ: 12.8, 14.1, 27.1, 27.2, 28.4, 39.2, 43.3, 45.4, 79.3, 80.4, 124.1, 124.9, 125.2, 125.3, 126.0, 127.3, 128.8, 129.2, 131.4, 135.0, 135.2, 139.4, 146.5, 154.6, 171.0.

(iv) Preparation of 4-(α-Hydroxyl-α-(4-N-t-butoxylcarbonylpiperidinyl)-2,6-dimethylbenzyl)-N,N-diethylbenzamide (compound 5)

Method as described for compund 4, except using 2-bromo-m-xylene; (749 mg, 76%):

m.p. 92–96° C. (CH$_2$Cl$_2$); ν$_{max}$ (KBr) cm$^{-1}$ 3451, 2970, 1690,1631, 1425,1165; Anal.Calcd.for C$_{30}$H$_{42}$N$_2$O$_4$.

0.50H$_2$O: C, 71.54; H, 8.61; N, 5.56. Found: C, 71.70; H, 8.34; N, 5.62; δ$_H$(400 MHz, CDCl$_3$) 1.10 (brs, 3H), 1.21 (brs, 3H), 1.32 (m, 2H), 1.43 (s, 9H), 1.69 (m, 1H), 1.77 (m, 1H), 2.32 (s, 6H), 2.47 (s, 1H), 2.75 (m, 3H), 3.25 (brs, 2H), 3.51 (brs, 2H), 4.13 (brs, 2H), 6.91 (m, 2H), 7.00 (m, 1H), 7.26 (d, J=8.4 Hz, 2H), 7.39 (d, J=8.4 Hz, 2H); δ$_{C-13}$ (100 MHz, CDCl$_3$) δ: 12.6, 14.0, 25.0, 27.7, 28.2, 39.1, 42.9, 43.1, 44.4, 53.3, 79.1, 83.0, 125.8, 126.3, 127.2, 131.2, 135.3, 136.7, 142.9, 147.8, 154.5, 170.7.

EXAMPLE 1

Preparation of N,N-Diethyl-4-(phenyl-piperidin-4-ylidene-methyl)-benzamide (compound 6)

To a solution of 4-(α-hydroxyl-α-(4-N-t-butoxylcarbonylpiperidinyl)-benzyl)-N,N-diethylbenzamide (932 mg, 2.0 mmol) in dry dichloromethane (10 mL) was added trifluoroacetic acid (10.0 mL) at r.t. The reaction mixture was stirred for 16 h at r.t., and then condensed. The residue was dissolved in AcOEt (100 ml). The resulting solution was washed with 1 N NaOH solution, aqueous NH$_4$Cl solution and brine, dried over MgSO$_4$. Removal of solvents gave a crude product, which was purified by silica gel column eluting with MeOH—CH$_2$Cl$_2$ (20:80) to provide (α-phenyl-α-(4-N',N'-diethylaminocarbonylphenyl))-4-methylene-piperidine (compound 6), (632 mg, 91%):

δ$_H$(400 MHz, CDCl$_3$) 1.08 (brs, 3H), 1.17 (brs, 3H), 2.29 (m, 4H), 2.86 (m, 4H), 2.94 (brs, 1H), 3.24 (brs, 2H), 3.47 (brs, 2H), 7.09 (m, 4H), 7.15 (m, 1H), 7.24 (m, 4H); δ$_{C-13}$ (100 MHz, CDCl$_3$) δ: 12.6, 14.1, 32.7, 32.8, 39.1, 43.2, 47.9, 126.0, 126.4, 127.9, 129.6, 134.9, 135.4, 135.9, 141.7, 143.2, 171.1.

HCl salt: m.p. 110–120° C.(AcOEt-Ether-CH$_2$Cl$_2$); ν$_{max}$ (KBr) cm$^{-1}$ 3440, 2970, 1617, 1438, 1289;

Anal.Calcd.for C$_{23}$H$_{28}$N$_2$O. 1.0 HCl. 0.50CH$_2$Cl$_2$. 0.25H$_2$O: C, 65.35; H, 7.12; N, 6.49. Found: C, 65.14; H, 7.08; N, 6.55.

EXAMPLE 2

Preparation of N,N-Diethyl-4-(1-naphtyl-piperidin-4-ylidene-methyl)-benzamide (compound 7)

Method as described for Example 1, using compound 4;(226 mg, 71%):

m.p. 80–85° C. (MeOH—CH$_2$Cl$_2$); ν$_{max}$ (KBr) cmr$^{-1}$ 3052, 2970, 1628, 1431, 1286;

Anal.Calcd.for C$_{27}$H$_{30}$N$_2$O. 0.20CH$_2$Cl$_2$: C, 78.62; H, 7.37; N, 6.74. Found: C, 78.63; H, 7.07; N, 6.54; δ$_H$(400 MHz, CDCl$_3$) 1.06 (brs, 3H), 1.16 (brs, 3H), 2.00 (m, 2H), 2.53 (m, 2H), 2.64 (brs, NH), 2.77 (m, 2H), 2.97 (m, 2H), 3.20 (brs, 2H), 3.47 (brs, 2H), 7.26 (m, 5H), 7.43 (m, 3H), 7.74 (m, 2H), 8.0 (m, 1H); δ$_{C-13}$ (100 MHz, CDCl$_3$) δ: 12.8, 14.1, 32.6, 33.5, 39.1, 43.2, 47.9, 48.2, 125.5, 125.7, 125.8, 126.1, 127.1, 127.2, 129.1, 131.9, 132.5, 133.8, 135.1, 138.3, 139.8, 142.6, 171.1

EXAMPLE 3

Preparation of N,N-Diethyl-4-(2,6-dimethylphenyl-piperidin-4-ylidene-methyl)-benzamide (compound 8)

Method as described for Example 1, using compound 5 (242 mg, 80%).

Its HCl salt: Dec. ≧115° C. (AcOEt-Ether-CH$_2$Cl$_2$); ν$_{max}$ (KBr) cm$^{-1}$ 2970, 2725, 1590, 1464, 1290, 1101;

EXAMPLE 4

Preparation of N,N-Diethyl-4-(1-naphtyl-N-allyl-piperidin-4-ylidene-methyl)-benzamide (compound 9)

A mixture of (α-(1-Naphthyl)-α-(4-N',N'-diethylaminocarbonylphenyl))-4-methylene-piperidine (compound 7) (125 mg), allyl bromide (90 mg) and $K_2CO_3$ (138 mg) in MeCN (10 mL) was stirred for 14 hr at r.t., and then quenched with 1 N $NH_4OH$ solution, extracted with AcOEt (100 ml). The organic phase was washed with aqueous $NH_4Cl$ solution and brine, dried over $MgSO_4$. Removal of solvents gave a crude product, which was purified by silica gel column eluting with MeOH—$CH_2Cl_2$ (2:98) to provide (α-(1-naphthyl)-α-(4-N',N'-diethylaminocarbonylphenyl))-4-methylene-N-allylpiperidine (50 mg, 36%):

$\delta_H$(400 MHz, $CDCl_3$) 1.08 (brs, 3H), 1.19 (brs, 3H), 2.08 (m, 2H), 2.39 (m, 2H), 2.61 (m, 4H), 3.01 (m, 2H), 3.24 (brs, 2H), 3.52 (brs, 2H), 5.13 (m, 2H), 5.90 (m, 1H), 7.27 (m, 5H), 7.45 (m, 3H), 7.80 (m, 2H), 8.04 (m, 1H); $\delta_{C-13}$ (100 MHz, $CDCl_3$) δ: 12.8, 14.1, 30.9, 32.0, 39.1, 43.2, 54.7, 54.9, 61.5, 117.8, 125.4, 125.6, 125.8, 126.0, 127.1, 128.2, 129.1, 131.8, 132.4, 133.7, 135.0, 138.0, 139.8, 142.6, 171.1.

Its HCl salt: m.p. 110–120° C. (AcOEt-Ether-$CH_2Cl_2$); $\nu_{max}$ (KBr) $cm^{-1}$ 3416, 2961, 1620, 1430, 1288;

Anal.Calcd.for $C_{30}H_{34}N_2O$. 1.0 HCl. 0.50$CH_2Cl_2$. 0.25$H_2O$: C, 70.17; H, 7.05; N, 5.37. Found: C, 70.15; H, 6.92; N, 5.24.

EXAMPLE 5

Preparation of N,N-Diethyl-4-(phenyl-N-benzyl-piperidin-4-ylidene-methyl)-benzamide (compound 10)

Method as described for Example 4, using compound 6 and benzyl bromide (215 mg, 98%):

$\delta_H$(400 MHz, $CDCl_3$) 1.09 (brs, 3H), 1.19 (brs, 3H), 2.37 (m, 4H), 2.47 (m, 4H), 3.25 (brs, 2H), 3.50 (brs, 4H), 7.0–7.30 (m, 14 H); $\delta_{C-13}$ (100 MHz, $CDCl_3$) δ: 12.7, 14.0, 31.6, 39.1, 43.1, 54.9, 55.0, 62.8, 125.9, 126.2, 126.8, 127.8, 128.0, 128.9, 129.6, 129.7, 134.9, 135.0, 136.3, 138.2, 141.9, 143.3, 171.0.

Its HCl salt: m.p. 230–245° C. (AcOEt-Ether-$CH_2Cl_2$); $\nu_{max}$ (KBr) $cm^{-1}$ 3423, 2976, 1624, 1434, 1288;

Anal.Calcd.for $C_{30}H_{34}N_2O$. 1.0 HCl. 0.25$CH_2Cl_2$. 0.25$H_2O$: C, 72.55; H, 7.25; N, 5.59. Found: C, 72.38; H, 7.16; N, 5.50.

EXAMPLE 6

Preparation of N,N-Diethyl-4-(N-2,3-epoxypropeyl-phenyl-piperidin-4-ylidene-methyl)-benzamide (compound 11)

Method as described for Example 4, using compound 6 and epibromohydrin (102 mg, 84%):

$\delta_H$(400 MHz, $CDCl_3$) 1.10 (brs, 3H), 1.20 (brs, 3H), 2.28 (m, 1H), 2.39 (m, 4H), 2.45 (m, 1H), 2.54 (m, 2H), 2.61 (m, 2H), 2.74 (m, 2H), 3.09 (m, 1H), 3.26 (brs, 2H), 3.50 (brs, 2H), 7.10 (m, 4H), 7.15 (m, 1H), 7.25 (m, 4H); $\delta_{C-13}$ (100 MHz, $CDCl_3$) δ: 12.8, 14.1, 31.4, 39.1, 43.2, 44.9, 50.1, 55.5, 60.8, 126.0, 126.4, 127.9, 129.6, 129.7, 135.0, 135.3, 135.7, 141.8, 143.2, 171.1.

EXAMPLE 7

Preparation of N,N-Diethyl-4-(1-cyclopropylmethyl-phenyl-piperidin-4-ylidene-methyl)-benzamide (compound 12)

Method as described for Example 4, using compound 6 and cyclopropylmethyl chloride (104 mg, 86%):

$\delta_H$(400 MHz, $CDCl_3$) 0.20 (m, 2H), 0.59 (m, 2H), 1.04 (m, 1H), 1.14 (brs, 3H), 1.24 (brs, 3H), 2.48 (d, J=6.4 Hz, 2H), 2.56 (brs, 4H), 2.80 (brs, 4H), 3.29 (brs, 2H), 3.53 (brs, 2H), 7.14 (m, 4H), 7.22 (m, 1H), 7.27 (m, 4H); $\delta_{C-13}$ (100 MHz, $CDCl_3$) δ: 4.18, 7.3, 12.8, 14.1, 30.3, 39.2, 43.2, 54.3, 62.7, 126.2, 126.6, 128.0, 129.5, 129.6, 134.1, 135.3, 136.3, 141.5, 142.9, 171.0.

Its HCl salt: Dec. $\geq$100° C.(AcOEt-Ether-$CH_2Cl_2$); $\nu_{max}$ (KBr) $cm^{-1}$ 3027, 2359, 1620, 1439, 958;

Anal.Calcd.for $C_{27}H_{34}N_2O$. 1.0 HCl. 0.50$CH_2Cl_2$. 0.75$H_2O$: C, 66.73; H, 7.64; N, 5.66. Found: C, 66.60; H, 7.45; N, 5.78.

B) Synthetic Scheme for the Preparation of the Compound of Example 8

The compound of Example 8 was prepared by following the procedure as is shown in Scheme 2 below.

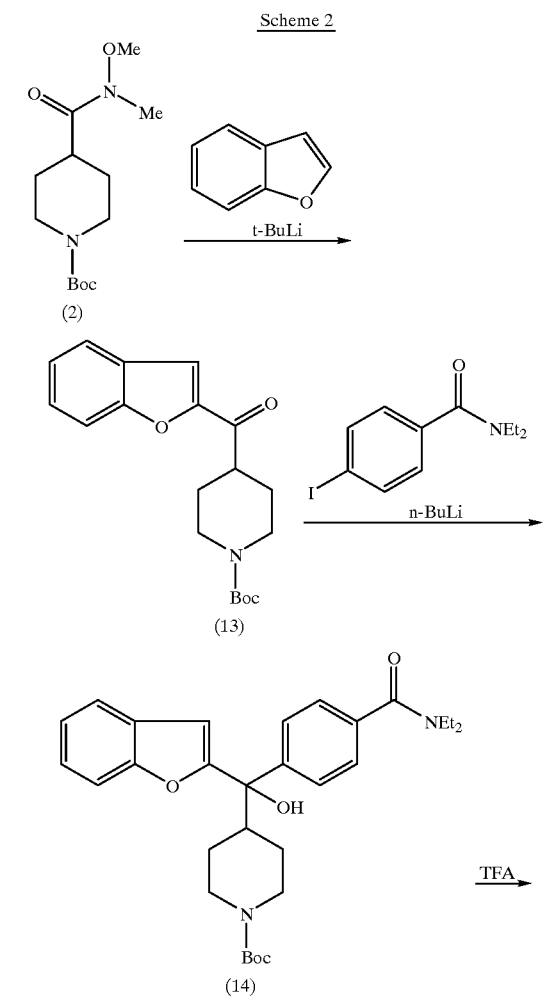

Scheme 2

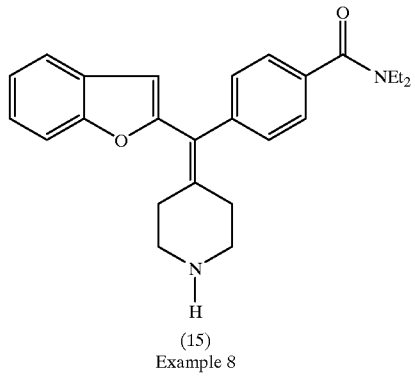

(15)
Example 8

(i) Preparation of 4-(2-Benzofuroyl)-N-t-butoxylcarbonylpiperidine (compound 13)

To a solution of 2,3-benzofuran (295 mg, 2.5 mmol) in dry THF (10 mL) was added t-butyllithium (1.5 mL, 1.7 M, 2.5 mmol) at −78° C. After 30 min, N-t-butoxylcarbonyl N-methyl-N-methoxyl-isonipecotamide (544 mg, 2.0 mmol) in THF (2 mL) was dropwise added. the reaction mixture was warmed to r.t. and then quenched with aqueous NH$_4$Cl solution, and extracted with ethyl acetate (2×50 mL). The combined organic layers were washed with brine, dried over MgSO$_4$. Removal of solvents gave a crude product, which was purified by silica gel column eluting with MeOH—CH$_2$Cl$_2$ (5:95) to provide 4-(2-benzofuroyl)-N-t-butoxylcarbonylpiperidine (13) (456 mg, 69%):

$\delta_H$(400 MHz, CDCl$_3$) 1.46 (s, 9H), 1.75 (m, 2H), 1.91 (m, 2H), 2.91 (m, 2H), 3.37 (m, 1H), 4.20 (brs, 2H), 7.29 (m, 1H), 7.46 (m, 1H), 7.53 (s, 1H), 7.56 (m, 1H), 7.69 (m, 1H); $\delta_{C-13}$ (100 MHz, CDCl$_3$) δ: 27.8, 28.3, 43.1, 44.4, 79.5, 112.3, 112.9, 123.1, 123.8, 126.9, 128.2, 151.8, 154.5, 155.5, 192.8.

(ii) Preparation of 4-(α-Hydroxy-α-(4-N-t-butoxylcarbonylpiperidinyl)-2-benzofuryl)-N,N-diethylbenzamide (compound 14)

Method as described for compound 4, using 4-iodo-N,N-diethylbenzamide (425 mg, 61%:

m.p. 102–106° C. (CH$_2$Cl$_2$); $\nu_{max}$ (KBr) cm$^{-1}$ 3362, 2970, 1690, 1617, 1425, 1288, 1160; $\delta_H$ (400 MHz, CDCl$_3$) 1.06 (brs, 3H), 1.20 (brs, 3H), 1.24 (m, 2H), 1.46 (m, 11 H), 2.42 (m, 1H), 2.58 (brs, 2H), 3.20 (brs, 2H), 3.50 (brs, 2H), 4.05 (brs, 2H), 4.37 (s, 1H), 6.70 (s, 1H), 7.16 (m, 2H), 7.23 (d, J=8.0 Hz, 2H), 7.41 (d, J=7.6 Hz, 1H), 7.47 (d, J=7.6 Hz, 1H), 7.58 (d, J=8.0 MHz, 2H); $\delta_{C-13}$ (100 MHz, CDCl$_3$) δ: 12.6, 13.9, 25.5, 26.3, 28.2, 39.0, 43.1, 44.9, 77.3, 79.0, 103.3, 110.9, 120.6, 122.5, 123.5, 125.6, 125.8, 127.9, 135.3, 144.0, 154.4, 154.5, 160.5, 170.9.

EXAMPLE 8

Preparation of N,N-Diethyl-4-(2-benzofuryl-piperidin-4-ylidene-methyl)-benzamide (compound 15)

Method as described for Example 1, using compound 14 (135 mg, 88%):

$\delta_H$(400 MHz, CDCl$_3$) 1.20 (brs, 3H), 1.24 (brs, 3H), 2.36 (brs, 2H), 3.00 (brs, 4H), 3.15 (brs, 2H), 3.33 (brs, 2H), 3.56 (brs, 2H), 4.45 (brs, 1H), 6.25 (s, 1H), 7.24 (m, 4H), 7.41 (m, 4H); $\delta_{C-13}$ (100 MHz, CDCl$_3$) δ: 12.9, 14.2, 29.6, 32.0, 32.4, 39.3, 43.4, 47.2, 107.4, 111.0, 120.7, 122.7, 124.2, 126.0, 126.5, 128.2, 129.9, 136.1, 139.5, 140.5, 154.4, 156.2, 171.0.

Its HCl salt: Dec. ≧120° C.(AcOEt-Ether-CH$_2$Cl$_2$); $\nu_{max}$ (KBr) cm$^{-1}$ 2977, 2801, 1586, 1449, 1257.

C) Synthetic Scheme for the Preparation of the Compounds of Examples 9–10

The compounds of Examples 9 and 10 were prepared by following the procedure of 5 Scheme 3 below.

Scheme 3

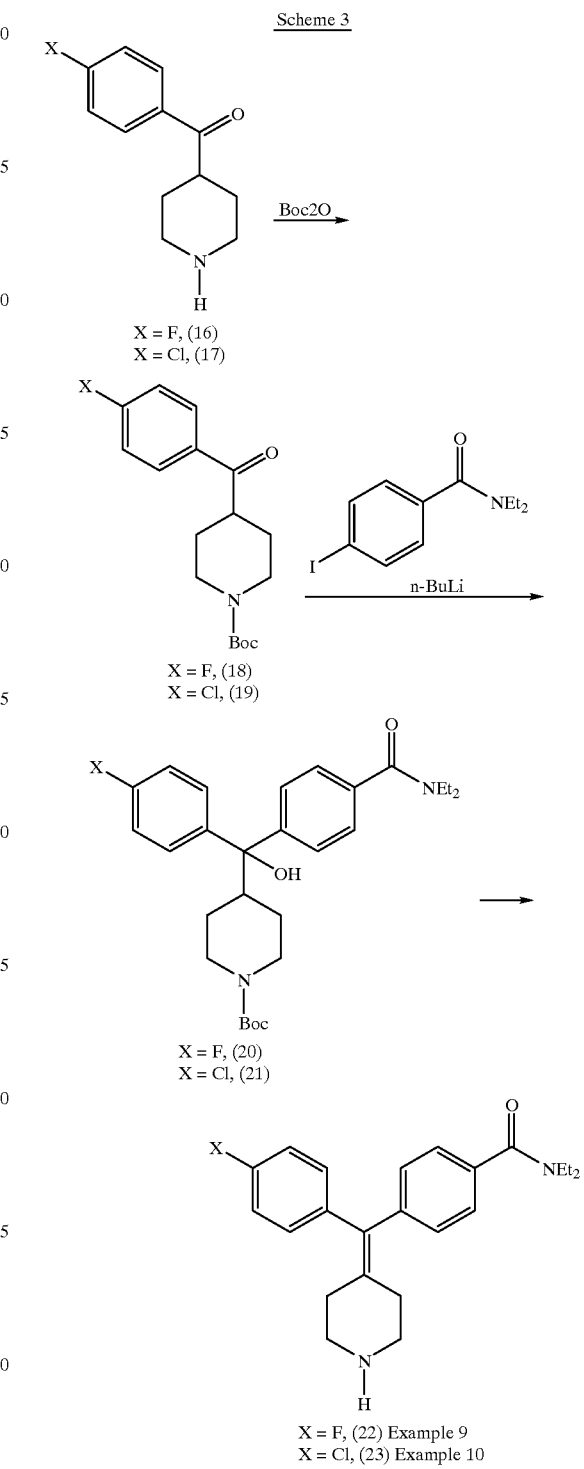

X = F, (22) Example 9
X = Cl, (23) Example 10

(i) Preparation of 4-(4-Fluorobenzoyl)-N-t-butoxylcarbonylpiperidine (compound 18)

A mixture of 4-(4-fluorobenzoyl)piperidine hydrochloride (compound 16) (2.44 g, 10.0 mmol), Di-tert-butyl dicarbonate (2.18 g, 10.0 mmol) and $Na_2CO_3$ (1.59 g, 15 mmol) in is $H_2O$-THF (50/5 mL) was refluxed for 1 h. The reaction mixture was extracted with ethyl acetate (2×100 mL). The combined organic layers were washed with brine, dried over $MgSO_4$. Removal of solvents gave 4-(4-fluorobenzoyl)-N-t-butoxylcarbonylpiperidine (OB 701–31, 2.28 g, 74%);

m.p. 80–83° C. ($CH_2Cl_2$); $\nu_{max}$ (KBr) $cm^{-1}$ 2980, 2842, 1680, 1587, 1416, 1160; $\delta_H$(400 MHz, $CDCl_3$) 1.44 (s, 9H), 1.69 (m, 2H), 1.79 (m, 2H), 2.87 (m, 2H), 3.34 (m, 1H), 4.13 (brs, 2H), 7.12 (m, 2H), 7.95 (m, 2H); $\delta_{C-13}$ (100 MHz, $CDCl_3$) δ: 27.4, 38.4, 43.2, 43.4, 79.6, 115.8, 115.9, 130.8, 130.9, 132.2, 154.6, 164.4, 166.9, 200.4.

(ii) Preparation of 4-(4-Chlorobenzoyl)-N-t-butoxylcarbonylpiperidine (compound 19)
Method as described for compound 18, using compound 17 (1.23 g, 85%):

m.p. 122–125° C. ($CH_2Cl_2$); $\nu_{max}$ (KBr) $cm^{-1}$ 2970, 2842, 1680, 1582, 1420, 1200; $\delta_H$(400 MHz, $CDCl_3$) 1.47(s, 9H), 1.69 (m, 2H), 1.81 (m, 2H), 2.90 (m, 2H), 3.36 (m, 1H), 4.18 (brs, 2H), 7.44 (m, 2H), 7.88 (m, 2H); $\delta_{C-13}$ (100 MHz, $CDCl_3$) δ: 28.3, 28.4, 43.2, 43.4, 79.6, 129.0, 129.6, 134.1, 139.4, 154.6, 200.7.

(iii) Preparation of 4-(α-Hydroxy-α-(4-N-t-butoxylcarbonylpiperidinyl)-4-fluorobenzyl)-N,N-diethylbenzamide (compound 20)
Method as described for compound 4, using compound 18 and 4-iodo-N,N-diethylbenzamide (454 mg, 47%):

m.p. 84–86° C. ($CH_2Cl_2$); $\nu_{max}$ (KBr) $cm^{-1}$ 3421, 2970, 1685, 1612, 1430, 1288, 1165; $\delta_H$(400 MHz, $CDCl_3$) 1.13 (brs, 3H), 1.23 (brs, 3H), 1.32 (m, 4H), 1.44 (s, 9H), 2.48 (m, 1H), 2.68 (brs, 2H), 3.26 (brs, 2H), 3.54 (brs, 2H), 3.57 (s, 1H), 4.11 (brs, 2H), 6.96 (m, 2H), 7.27 (d, J=8.0 Hz, 2H), 7.44 (m, 2H), 7.47 (d, J=8.0 Hz, 2H); $\delta_{C-13}$ (100 MHz, $CDCl_3$) δ: 12.9, 14.0, 26.2, 28.2, 39.1, 43.2, 43.6, 44.3, 78.9, 79.1, 114.5, 114.7, 125.7, 126.1, 127.5, 127.6, 135.0, 141.2, 146.9, 154.5, 160.0, 162.5, 170.9.

(iv) Preparation of 4-(α-Hydroxy-α-(4-N-t-butoxylcarbonylpiperidinyl)-4-chlorobenzyl)-N,N-diethylbenzamide (compound 21)
Method as described for compound 4, using compound 19 and 4-iodo-N,N-diethylbenzamide (626 mg, 63%):

m.p. 100–105° C. ($CH_2Cl_2$); $\nu_{max}$ (KBr) $cm^{-1}$ 3411, 2970, 1685, 1617, 1425, 1288, 1165, 1092; $\delta_H$(400 MHz, $CDCl_3$) 1.08 (brs, 3H), 1.20 (brs, 3H), 1.33 (m, 4H), 1.41 (s, 9H), 2.44 (m, 1H), 2.63 (brs, 2H), 3.22 (brs, 2H), 3.49 (brs, 2H), 3.99 (s, 1H), 4.05 (m, 2H), 7.20 (m, 4H), 7.39 (d, J=8.0 Hz, 2H), 7.44 (d, J=8.0 Hz, 2H); $\delta_{C-13}$ (100 MHz, $CDCl_3$) δ: 12.5, 13.9, 25.9, 28.1, 39.0, 43.0, 44.1, 78.7, 79.0, 125.6, 126.0, 127.2, 127.8, 131.9, 134.8, 144.1, 146.6, 154.3, 170.7.

EXAMPLE 9

Preparation of N,N-Diethyl-4-(4-fluorophenyl-piperidin-4-ylidene-methyl)-benzamide (compound 22)

Method as described for Example 1 (compound 6), using compound 20. $^1$H-NMR (400 MHz, $CDCl_3$) δ 1.12 (3H, br m, C$\underline{H}_3CH_2$—), 1.24 (3 H, br m, C$\underline{H}_3CH_2$—), 2.32 (4H, m, piperidine C$\underline{H}$—), 2.54 (1 H, br m, N$\underline{H}$), 2.91 (4 H, m, piperidine C$\underline{H}$—), 3.27 (2 H, br m, C$\underline{H}_2$N—), 3.52 (2 H, br m, C$\underline{H}_2$N—), 7.00 (2 H, m, Ar$\underline{H}$), 7.09 (2 H, m, Ar$\underline{H}$), 7.11 (2 H, d, J=8.0 Hz, Ar$\underline{H}$), 7.29(2 H, d, J=8.0 Hz, Ar$\underline{H}$).

EXAMPLE 10

Preparation of N,N-Diethyl-4-(4-chlorophenyl-piperidin-4-ylidene-methyl)-benzamide (compound 23)

Method as described for Example 1 (compound 6), using compound 21.
$^1$H-NMR (400 MHz, $CDCl_3$) δ 1.13 (3 H, br m, C$\underline{H}_3CH_2$—), 1.22 (3 H, br m, C$\underline{H}_3CH_2$—), 2.02 (1 H, br m, N$\underline{H}$), 2.30 (4 H, m, piperidine C$\underline{H}$—), 2.90 (4 H, m, piperidine C$\underline{H}$—), 3.28 (2 H, br m, C$\underline{H}_2$N—), 3.53 (2 H, br m, C$\underline{H}_2$N—), 7.04 (2 H, d, J=8.0 Hz, Ar$\underline{H}$), 7.11 (2 H, d, J=8.0 Hz, Ar$\underline{H}$), 7.25 (2 H, d, J=8.0 Hz, Ar$\underline{H}$), 7.30 (2 H, d, J=8.0 Hz, Ar$\underline{H}$).

Its HCl salt: m.p. 115–120° C. ($H_2O$—$CH_2Cl_2$); IR (KBr) 3337,2973, 1618, 1431, 1290, 1092 $cm^{-1}$;

AnaL Calcd. for $C_{23}H_{27}ClN_2O.1.0HCl.1.20H_2O$: C, 62.64%; H, 6.95%; N, 6.35%; Found: C, 62.53%; H, 6.91%; N, 6.30%.

D) Synthetic Scheme for the Preparation of the Compound of Example 11

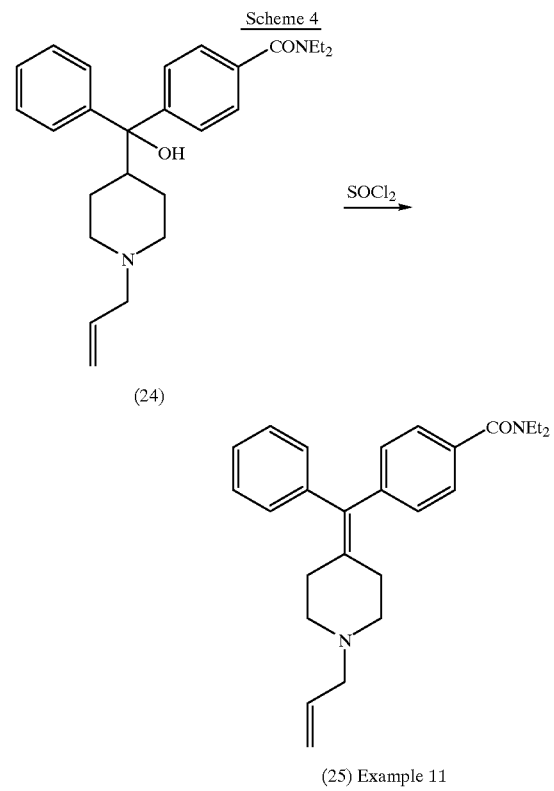

(24)

(25) Example 11

EXAMPLE 11

Preparation of N,N-Diethyl-4-(phenyl-N-allyl-piperidin-4-ylidene-methyl)-benzamide (compound 25)

4-(α-hydroxy-α-(4-N-allylpiperidinyl)-benzyl)-N,N-diethylbenzamide (compound 24) (81 mg) was dissolved in $CH_2Cl_2$ (10 ml) and was treated with thionyl chloride (2 ml) at r.t. The reaction mixture was refluxed for 2 hrs, and then condensed. The residue was dissolved in ethyl acetate (50 mL) and the resulting solution was washed with $NH_4OH$ (1 N), aqueous $NH_4Cl$ solution and brine, dried over $MgSO_4$.

Removal of solvents gave a crude product, which was purified by silica gel column eluting with MeOH—CH$_2$Cl$_2$ (1:99→5:95) to provide (α-phenyl-α-(4-N',N'-diethylaminocarbonylphenyl))-4-methylene-N-allylpiperidine (compound 25; Example 11) (32 mg, 40%):

δ$_H$(400 MHz, CDCl$_3$) 1.12 (brs, 3H), 1.21 (brs, 3H), 2.43 (m, 4H), 2.55 (m, 4H), 3.08 (d, J=6.8 Hz, 2H), 3.25 (brs, 2H), 3.53 (brs, 2H), 5.18 (m, 2H), 5.86 (m, 1H), 7.12 (m, 4H), 7.20 (m, 1H), 7.27 (m, 4H).

Its HCl salt: m.p. 85–95° C. (AcOEt—CH$_2$Cl$_2$); ν$_{max}$ (KBr) cm$^{-1}$ 3491, 2971, 1624, 1428, 1289, 1096;

Anal.Calcd.for C$_{26}$H$_{32}$N$_2$O.HCl. 0.25 H$_2$O. 0.25CH$_2$Cl$_2$: C, 69.95; H, 7.60; N, 6.21. Found: C, 70.00; H, 7.73; N, 6.07.

EXAMPLE 12

Preparation of N,N-Diethyl-4-(4-chlorophenyl-N-benzyl-piperidin-4-ylidene-methyl)-benzamide (compound 26)

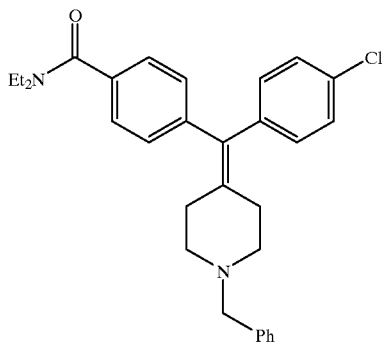

(26)

Method as described for Example 4, using compound 23 (96 mg) and benzyl bromide (43 mg) provided N,N-diethyl4-(4-chlorophenyl-N-benzyl-piperidin-4-ylidene-methyl)-benzamide (110 mg, 93%):

$^1$H-NMR (400 MHz, CDCl$_3$) δ 1.13 (3 H, br m, CH$_3$CH$_2$—), 1.23 (3 H, br m, CH$_3$CH$_2$—), 2.37 (4 H, m, piperidine CH—), 2.49 (4 H, m, piperidine CH—), 3.28 (2H, br m, CH$_3$CH$_2$N—), 3.53 (4 H, br, m, PhCH$_2$N and CH$_3$CH$_2$N—), 7.04 (2 H, d, J=8.0 Hz, ArH), 7.11 (2 H, d, J=8.0 Hz, ArH), 7.25 (2 H, d, J=8.0 Hz, ArH), 7.29 (7 H, m, ArH).

Its (CHOHCO$_2$H)$_2$ salt: m.p. 100–110° C. (MeOH); IR (KBr) 3368, 2977, 1728, 1603, 1433, 1290, 1087 cm$^{-1}$;

AnaL Calcd.for C$_{34}$H$_{39}$ClN$_2$O$_7$.1.50H$_2$O: C, 62.81%; H, 6.51%; N, 4.31%; Found: C, 62.85%; H, 6.17%; N, 4.21%.

EXAMPLE 13

Preparation of N,N-Diethyl-4-[(N-3-methyl-2-butenyl)-phenyl-piperidin-4-ylidene-methyl]-benzamide (compound 27)

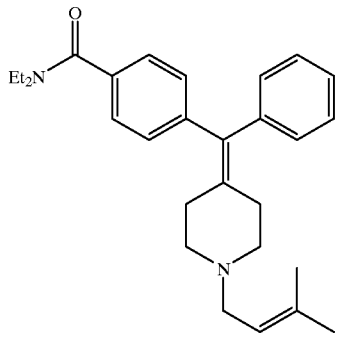

(27)

Method as described for example 4, using 1-Bromo-3-methyl-2-butene as the alkylating reagent.

IR (NaCl Film): HCl salt ν=3432, 2976, 1623, 1434, cm$^{-1}$.

$^1$H NMR: (Base) (CDCl$_3$, TMS) δ: 1.10~1.30 (6H, br, OCNCH$_2$CH$_3$), 1.64 (3H, s, =CCH$_3$), 1.73 (3H, s, =CCH$_3$), 2.40 (4H, m, NCH$_2$CH$_2$), 2.52 (4H, m, =CCH$_2$), 3.0 (2H, d, J=7.6 Hz, NCH$_2$CH=C), 3.20~3.60 (4H, br, OCNCH$_2$CH$_3$),. 5.28 (1H, m, NCH$_2$CH=C), 7.16~7.45(9H, m, Ar)ppm.

ANALYSIS: (%)AnaL.Calcd.for:: C$_{28}$H$_{36}$N$_2$O. 1.8HCl: C, 69.74; H, 7.90; N, 5.81. Found: C, 69.71; H, 7.48; N, 5.58.

EXAMPLE 14

Preparation of N,N-diethyl-4-[r(1-Cyclohexyl-piperidin-4-ylidene)-phenyl-methyl]-benzamide (compound 28)

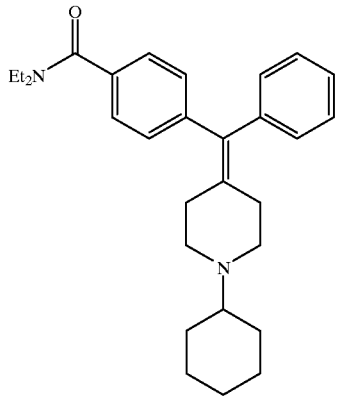

(28)

A mixture of compound 6 (100 mg, 0.29 mmol), cyclohexanone (36 ul, 0.35 mmol) and Ti(OPr-i)$_4$ (0.17 ml, 0.58 mmol) was ultrasonicated for 1 hr and then stirred at rt overnight under a nitrogen atmosphere. The mixture was diluted with ethanol (5 ml) and followed by addition of NaBH$_4$ (33 mg, .87 mmol). The resulting mixture was stirred for 12 hr at rt. 2N NH$_3$.H$_2$O was added to quench the reaction and the mixture filtered through celite. The filtrate was extracted with ethyl acetate several times and the combined organic phases washed with water and brine, and dried over $Na_2SO_4$. Concentration in vacuo and MPLC purification (0::100 to 100:0 EtOAc:Heptane eluting on silcal gel 60) gave the title compound (24 mg, 20%).

m.p. (HCl salt): 105–109° C. IR (HCl salt, film) ν: 3394 (NH), 1620 ($CONEt_2$)$cm^{-1}$.

$^1$H NMR (free amine, 400 MHz, $CDCl_3$) δ: 1.00–1.25 (17H, m, $NCHCH_2CH_2CH_2CH_2$, 2×$CH_3$ and $CH(CH)C=C$), 1.60 (1H, m, $CH(CH)C=C$), 1.75 (1H, m, $CH(CH)C=C$), 1.80 (1H, m, $CH(CH)C=C$), 2.30 (3H, m, $NCH_2$ and $NCH$), 2.60 (2H, m, $NCH_2$), 3.20 (2H, bs, $NCH_2CH_3$), 3.50 (2H, bs, $NCH_2CH_3$), 7.00–7.30 (9H, m, Ar).

$^{13}$C NMR (free amine, 100 MHz, $CDCl_3$) δ: 12.7, 14.1, 25.9, 28.7, 32.0, 39.1, 43.2, 50.7, 50.8, 63.6, 126.0, 126.3, 127.9, 129.7, 129.8, 134.7, 134.9, 136.9, 142.0, 143.4, 171.2. Elemental analysis: Calcd.for $C_{29}H_{40}N_2OCl_2$: C, 69.17; H, 8.01; N, 5.56. Found: C, 69.17; H, 7.82; N, 5.18.

EXAMPLE 15

Preparation of N,N-Diethyl-4-[(N-butyl)-phenyl-piperidin-4-ylidene-methyl]-benzamide (compound 29)

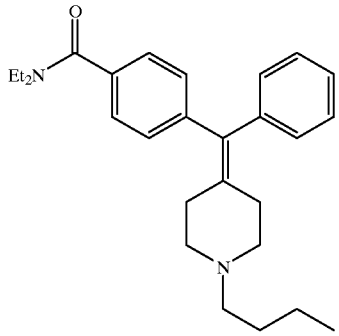

(29)

Method as described for Example 4, using 1-Iodobutane as the alkylating reagent. IR (NaCl Film):(HCl salt) ν=3430, 2967, 2499, 1622, 1433$cm^{-1}$ $^1$H NMR: ($CDCl_3$, TMS) δ: 0.92 (3H, t, J=7.2 Hz, $CH_2CH_3$), 1.10~1.26 (6H, br, $OCNCH_2CH_3$), 1.32 (2H, m, $CH_2CH_3$), 1.53 (2H, m, $CH2CH_2CH2$), 2.42 (6H, m, $NCH_2$), 2.55 (4H, m, $=CCH_2$), 3.20~3.60 (4H, br, $OCNCH_2CH_3$), 7.10~7.31 (9H, m, Ar)ppm. ANALYSIS: (%)
AnaL.Calcd.for:$C_{27}H_{36}N_2O$•HCl•0.4$CH_2Cl_2$•0.4$H_2O$:C, 68.24; H, 8.07; N, 5.81. Found: C, 68.24; H, 8.12; N, 5.89.

EXAMPLE 16

Preparation of N,N-Diethyl-4-[(N-4-methoxybenzyl)-phenyl-piperidin-4-ylidene-methyl]-benzamide (compound 30)

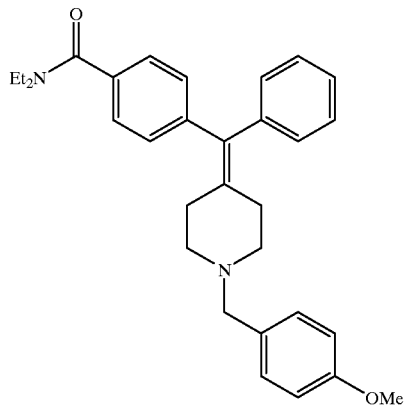

Method as described for Example 4, using compound 6 (174 mg) and 4-methoxybenzyl chloride (78 mg) provided N,N-diethyl-4-[(N-4-methoxybenzyl)-phenyl-piperidin-4-ylidene-methyl]-benzamide (160 mg, 68%):
$^1$H-NMR (400 MHz, $CDCl_3$) δ 1.11 (3 H, br, C$H_3CH_2N$—), 1.20 (3 H, br, $CH_3CH_2N$—), 2.38 (4 H, m, $CCH_2C$), 2.46 (4 H, m, $NCH_2$—), 3.26 (2 H, m, NC$H_2$—), 3.47 (2H, s, $CH_2N$—), 3.49 (2 H, br, $CH_3CH_2N$—), 3.77 (3H, s, $OCH_3$), 6.83 (2H, d, J=8.0 Hz, Ar H), 7.05–7.30 (11 H, m, ArH).
Its HCl salt: m.p. 100–110° C. ($CH_2Cl_2$); IR (KBr) 3425, 2974, 1618, 1515, 1434, 1255 $cm^{-1}$;
Anal.Calcd.for $C_{31}H_{36}N_2O_2$.1.0HCl 0.35$CH_2Cl_2$: C, 70.41%; H, 7.1 1%; N, 5.24%; Found: C, 70.46%; H, 7.10%; N, 5.2 1%.

EXAMPLE 17

Preparation of N,N-Diethyl-4-[(N-2,4-dichlorobenzyl)-phenyl-piperidin-4-ylidene-methyl]-benzamide (compound 31)

(31)

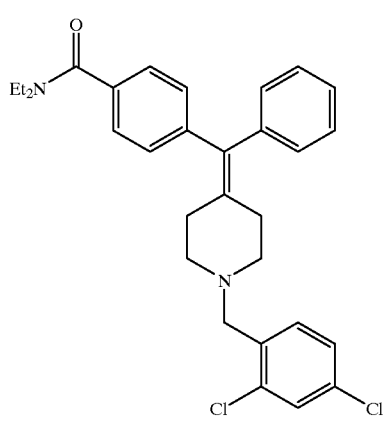

Method as described for Example 4, using compound 6 (174 mg) and α,2,4-trichlorotoluene(98 mg) provided N,N-diethyl-4-[(N-2,4-dichlorobenzyl)-phenyl-piperidin-4-ylidene-methyl]-benzamide (206 mg, 81%):
$^1$H-NMR (400 MHz, $CDCl_3$) δ 1.12 (3 H, br, C$H_3CH_2N$—), 1.21 (3 H, br, $CH_3CH_2N$—), 2.39 (4 H, m, CC H₂C), 2.52 (4 H, m, NCH₂—), 3.28 (2 H, m, NCH₂—), 3.53 (2 H, br, CH₃CH₂N—), 3.57 (2 H, m, NCH₂—), 7.05–7.48 (12 H, m, ArH).

Its HCl salt: m.p. 95–110° C. (CH₂Cl₂); IR (KBr) 3408, 2976, 1620, 1472, 1436, 1288, 1101 cm⁻¹;

Anal.Calcd.for C₃₀H₃₂N₂OCl₂.1.0HCl 0.30CH₂Cl₂: C, 63.91%; H, 5.95%; N, 4.92%; Found: C, 63.81%; H, 6.03%; N, 4.84%.

EXAMPLE 18

Preparation of N,N-Diethyl-4-[(1-methyl-piperidin-4-ylidene)-phenyl-methyl]-benzamide (compound 32)

(32)

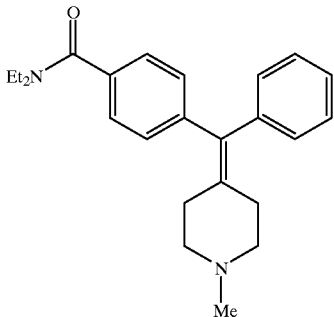

N,N-Diethyl-4-[(piperidin4-ylidene)-phenyl-methyl]-benzamide (0.34 g, 1.0 mmol) was disolved in acetonitrile (5 mL). Potassium carbonate (0.14 g, 1.0 mmol) and methyl iodide (63 μL, 1.0 mmol) was added with stirring at 25° C. After 30 min., the reaction mixture was evaporated and put onto silica gel for purification by chromatography using 0 to 10% MeOH(10% NH₄OH) in CH₂Cl₂ to give 48 mg of the final product (28% of converted starting material), which was converted to the hydrochloride salt by treatment with HCl in ether.

Mp: 110° C. (dec.). IR (KBr) (cm-1): 2361, 1695, 1487, 1289. MS(free amine): 362, 318, 219, 189, 165, 144.

¹H NMR: (amine, CDCl₃): δ=1.1(m, 6H, amide-Me), 2.40 (s, 3H, MeN), 2.49, 2.60 (2 m, 8H, piperazine-H), 3.40 (m, 4H, amide-CH₂) 7.08–7.34 (m, 9H, Ar—H). C₂₄H₃₀N₂O× 0.1 H₂O×3.1 HCl, requires: C:60.39, H:7.03, N:5.87. Found C:60.43, H:6.84, N:5.45.

EXAMPLE 19

Preparation of N,N-Diethyl-4-[(N-tert-butoxycarbonyl-piperidin-4-yl)-8-quinolinyl-hydroxy-methyl]-benzamide (compound 33)

(33)

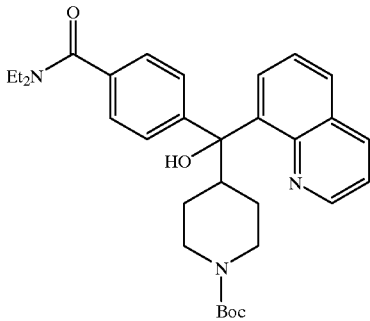

To a solution of 4-iodo-N,N-diethylbenzamide (1.52 g, 5.0 mmol) and 8-bromoquinoline (1.0 g) in dry THF (30 mL) was added n-butyllithium (7.0 mL, 2.5 M, 17.5 mmol) at −78° C. After 10 min, N-t-butoxylcarbonyl ethyl isonipecotate (2) (0.77 g, 3.0 mmol) in THF (5 mL) was dropwise added. The reaction mixture was warmed to ° C., and then quenched with aqueous NH₄Cl solution, and extracted with ethyl acetate (2×100 mL). The combined organic layers were washed with brine, dried over MgSO₄. Removal of solvents gave a crude product, which was purified by silica gel column eluting with MeOH—CH₂Cl₂ (2:98) to MTL 0599 (145 mg, 9%):

m.p. 100–105° C.; IR (NaCl) 2971, 1686,1625,1426, 1167 cm⁻¹;

Anal. Calcd.for C₃₁H₃₉N₃O₄.0.20H₂O: C, 71.43%; H, 7.62%. Found: C, 71.50%; H, 7.75%; ¹H-NMR (400 MHz, CDCl₃) δ 1.07 (3 H, br, CH₃CH₂N—), 1.19 (3 H, br, CH₃CH₂N—), 1.24 (1 H, m, piperidine CH—), 1.43 (9 H, s, CH₃C), 1.65 (1 H, m, piperidine CH—), 1.89 (2 H, m, piperidine CH—), 2.52 (1 H, m, piperidine CH—), 2.64 (1 H, br, piperidine CH—), 2.78 (1 H, br, piperidine CH—), 3.22 (2 H, br, CH₃CH₂N—), 3.49 (2 H, br, CH₃CH₂N—), 4.16 (2 H, br, piperidine CH—), 7.24 (2 H, d, J=8.0 Hz, Ar H), 7.35 (1 H, dd, J=8.0, 4.4 Hz, ArH), 7.55 (2H, d, J=8.0 Hz, ArH), 7.58 (1 H, d, J=8.0 Hz, ArH), 7.71 (1 H, d, J=8.0 Hz, ArH), 7.80 (1 H, d, J=8.0 Hz, ArH), 8.14 (1 H, d, J=8.0 Hz, ArH), 8.69 (1H, m, ArH), 9.80 (1H, s, OH).

EXAMPLE 20

Preparation of N,N-Diethyl-4-(8-quinolinyl-piperidin-4-ylidene-methyl)-benzamide (compound 34)

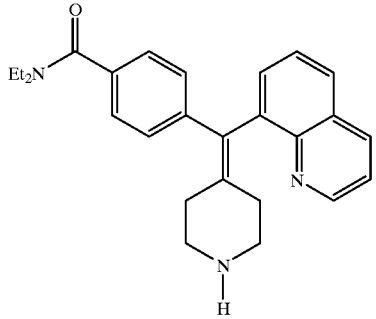
(34)

A mixture of the compound of Example 19 (45 mg), trifluoroacetic acid (1.0 mL) and trifluoromethanesulforic acid (1 mL) was refluxed for 8 hrs., and then condensed. The residue was dissolved in AcOEt (50 ml). The resulting solution was washed with 1 N NaOH solution, aqueous NH$_4$Cl solution and brine, dried over Na$_2$SO$_4$. Removal of solvents gave a crude product, which was purified by silica gel column eluting with NH$_4$OH (1N)—MeOH—CH$_2$Cl$_2$ (2.5:17.5:80) to provide N,N-diethyl-4-(8-quinolinyl-piperidin-4-ylidene-methyl)-benzamide (29 mg, 84%):

$^1$H-NMR (400 MHz, CDCl$_3$) δ 1.07 (3 H, br m, CH$_3$CH$_2$—), 1.20 (3 H, br m, CH$_3$CH$_2$—), 2.00 (2 H, m, piperidine CH—), 2.46 (1H, s, NH), 2.52 (2 H, m, piperidine CH—), 2.75 (1 H, m, piperidine CH—), 2.92 (2 H, m, piperidine CH—), 3.05 (1H, m, piperidine CH—), 3.22 (2 H, m, CH$_2$N—), 3.49 (2 H, m, CH$_2$N—), 7.23 (2 H, m, ArH), 7.32 (2H, m, ArH), 7.36 (1 H, m, ArH), 7.49 (2 H, m, ArH), 7.72 (1 H, dd, J=6.4, 3.2 Hz, ArH), 8.11 (1 H, dd, J=8.4, 1.6 Hz, ArH), 8.91 (1 H,dd, J=4.0, 1.6 Hz, ArH).

Its HCl salt: m.p. >170° C. (Dec.); IR (KBr) 3410, 2973, 1614, 1551, 1436, 1284 cm$^{-1}$;

Anal.Calcd.for C$_{26}$H$_{29}$N$_3$O. 2.0 HCl. 0.50 CH$_2$Cl$_2$. 0.75H$_2$O: C, 60.23%; H, 6.39%; Found: C, 60.27%; H, 6.42%.

EXAMPLE 21

Preparation of N,N-Diethyl-4-[(N-tert-butoxycarbonyl-piperidin-4-yl)-3-methoxyphenyl-hydroxy-methyl]-benzamide (compound 35)

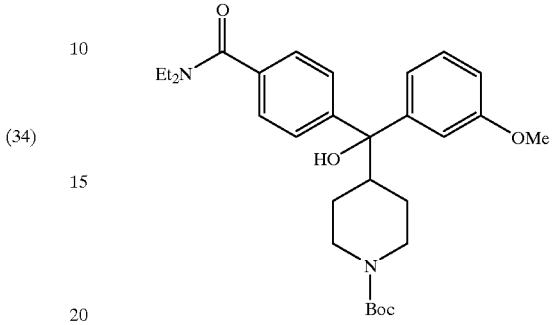
(35)

Method as for Example 19 using 3-bromoanisole provided the title compound (226 mg, 23%):

m.p. 95–103° C.; IR (NaCl) 3422, 2973, 1684, 1614, 1429, 1289 cm$^{-1}$;

Anal.Calcd.for C$_{29}$H$_{40}$N$_2$O$_5$.0.60H$_2$O: C, 68.64%; H, 8.18%; N, 5.52%. Found: C, 68.66%; H, 7.98%; N, 5.64%; $^1$H-NMR (400 MHz, CDCl$_3$) δ 1.07 (3 H, br, CH$_3$CH$_2$N—), 1.19 (3 H, br, CH$_3$CH$_2$N—), 1.31 (4 H, m, piperidine CH—), 1.41 (9 H, s, CH$_3$C), 2.46 (1 H, m, piperidine CH—), 2.64 (2 H, br, piperidine CH—), 3.22 (2 H, br, CH$_3$CH$_2$N—), 3.49 (2 H, br, CH$_3$CH$_2$N—), 3.65 (1H, s, OH), 3.72 (3H, s, OCH$_3$), 4.06 (2 H, br, piperidine CH—), 6.69 (1H, m, ArH), 7.01 (1H, d, J=7.6 Hz, ArH), 7.08 (1 H, s, ArH), 7.17 (1H, d, J=8.0 Hz, ArH), 7.21 (2 H, d, J=8.0 Hz, ArH), 7.48 (2 H, d, J=8.0 Hz, ArH).

EXAMPLE 22

Preparation of N,N-Diethyl-4-(3-methoxyphenyl-piperidin-4-ylidene-methyl)-benzamide (compound 36)

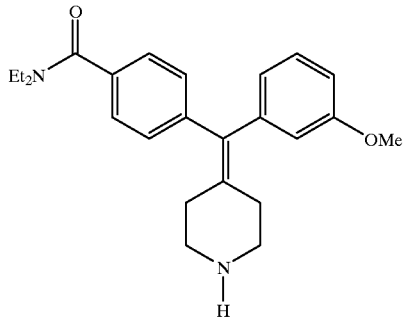
(36)

Method as described for Example 1, using the compound of Example 21 (100 mg) provided N,N-diethyl-4-(3-methoxyphenyl-piperidin-4-ylidene-methyl)-benzamide (75 mg, 98%)

¹H-NMR (400 MHz, CDCl₃) δ 1.12 (3 H, br, CH₃CH₂N—), 1.23 (3 H, br, CH₃CH₂N—), 2.34 (4 H, m, piperidine CH—), 2.91 (4 H, br, piperidine CH—), 3.17 (1H, s, NH), 3.27 (2 H, br, CH₃CH₂N—), 3.52 (2 H, br, CH₃CH₂N—), 3.76 (3H, s, OCH₃), 6.64 (1 H, s ArH), 6.70 (1H, d, J=8.0 Hz, ArH), 6.76 (1 H, d, J=7.6 Hz, ArH), 7.15 (2 H, d, J=8.0 Hz, ArH), 7.22 (1H, m, ArH), 7.29 (2 H, d, J=8.0 Hz, ArH).

Its HCl salt: m.p. >90° C. (Dec); IR (NaCl) 2970, 1621, 1430, 1287 cm⁻¹;

Anal.Calcd.for C₂₄H₃₀N₂O₂.HCl.1.70H₂O: C, 64.69%; H, 7.78%; N, 6.29%; Found: C, 64.82%; H, 7.60%; N, 6.08%.

EXAMPLE 23

Preparation of N,N-Diethyl-4-[(N-benzyl)-3-methoxyphenyl-piperidin-4-ylidene-methyl]-benzamide (compound 37)

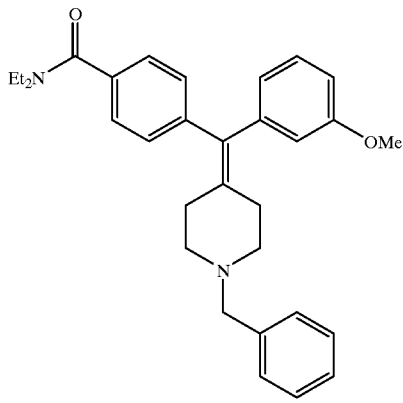

(37)

Method as for Example 4, using the compound of Example 22 (38 mg) provided N,N-diethyl-4-[(N-benzyl)-3-methoxyphenyl-piperidin4-ylidene-methyl]-benzamide (46 mg, 98%):

¹H-NMR (400 MHz, CDCl₃) δ 1.12 (3 H, br, CH₃CH₂N—), 1.25 (3 H, br, CH₃CH₂N—), 2.38 (4H, m, piperidine CH—), 2.48 (4 H, br, piperidine CH—), 3.27 (2 H, br, CH₃CH₂N—), 3.52 (2H, s, Ph CH₂N), 3.53 (2 H, br, CH₃CH₂N—), 3.75 (3H, s, OCH₃), 6.65 (1 H, s, ArH), 6.69 (1H, d, J=8.0 Hz, ArH), 6.74 (1H, d, J=7.6 Hz, ArH), 7.13 (2 H, d, J=8.0 Hz, ArH), 7.13–7.32 (8H, m, ArH).

Its HCl salt: m.p. 100–110° C. (CH₂Cl₂); IR (NaCl) 3421, 2972, 1619, 1430, 1287 cm⁻¹;

Anal.Calcd.for C₃₁H₃₆N₂O₂.HCl.0.40CH₂Cl₂: C, 69.96%; H, 7.07%; N, 5.20%; Found: C, 69.94%; H, 7.06%; N, 5.15%.

EXAMPLE 24

Preparation of N,N-Diethyl-4-[(N-tert-butoxycarbonyl-piperidin-4-yl)-3-fluorophenyl-hydroxy-methyl]-benzamide (compound 38)

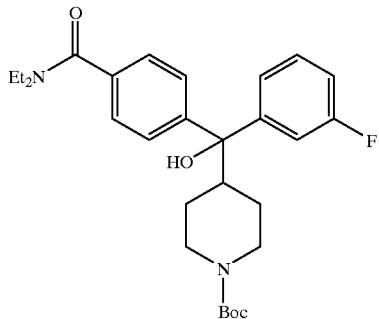

(38)

Method as for Example 19 using 3-bromofluorobenzene provided the title compound (257 mg, 27%:

¹H-NMR (400 MHz, CDCl₃) δ 1.03 (3 H, br, CH₃CH₂N—), 1.15 (3 H, br, CH₃CH₂N—), 1.19–1.29 (4 H, m, piperidine CH—), 1.35 (9 H, s, CH₃C), 2.39 (1H, m, piperidine CH—), 2.59 (2 H, br, piperidine CH—), 3.17 (2 H, br, CH₃CH₂N—), 3.28 (1H, s, OH), 3.45 (2 H, br, CH₃CH₂N—), 4.02 (2H, br, piperidine CH—), 6.80 (1 H, m, ArH), 7.15 (3 H, m, ArH), 7.18 (2H, d, J=8.0 Hz, ArH), 7.39 (2H, d, J=8.0 Hz, ArH).

EXAMPLE 25

Preparation of N,N-Diethyl-4-(3-fluorophenyl-piperidin-4-ylidene-methyl)-benzamide (compound 39)

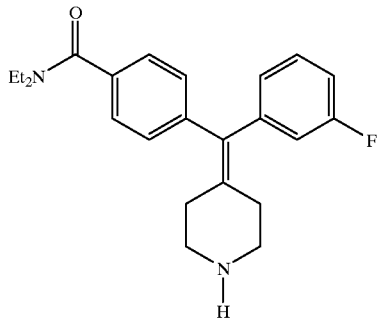

(39)

Method as for Example 20 using the compound of Example 24 (165 mg) provided N,N-Diethyl-4-(3-fluorophenyl-piperidin-4-ylidene-methyl)-benzamide (108 mg, 87%):

¹H-NMR (400 MHz, CDCl₃) δ 1.08 (3 H, br, CH₃CH₂N—), 1.19 (3 H, br, CH₃CH₂N—), 2.09 (1H, s, NH), 2.25 (4 H, m, piperidine CH—), 2.84 (4 H, br, piperidine CH—), 3.23 (2 H, br, CH₃CH₂N—), 3.47 (2 H, br, CH₃CH₂N—), 6.74 (1 H, m, ArH), 6.86 (2H, m, ArH), 7.06 (2 H, d, J=8.0 Hz, ArH), 7.18 (1H, m, ArH), 7.24 (2 H, d, J=8.0 Hz, ArH).

Its HCl salt: m.p. >70° C. (Dec.); IR (NaCl) 2978, 1605, 1478, 1432, 1290 cm⁻¹;

Anal.Calcd.for $C_{23}H_{27}N_2OF \cdot HCl \cdot 0.25\ CH_2Cl_2 \cdot 1.50H_2O$: C, 61.89%; H, 7.04%; N, 6.21%; Found: C, 61.97%; H, 6.95%; N, 6.22%.

E) Synthetic Scheme for the Preparation of the Compound of Example 26

The compound of Example 26 was prepared by following the procedure as is shown in Scheme 5 below.

stirred for 2 hr. The gray color precipitate formed during the reaction was filtered, washed with ether and collected, the mother solution was concentrated to dryness and AcOEt was added, the resulting precipitate was filtered, washed with ether and combined with the previous solid as the desired product (15.95 g, 88.7%).

$^1$H NMR: $(CDCl_3)$ δ: 2.19 (3H, s, $COC\underline{H}_3$), 7.2 (1H, s, br, —N$\underline{H}$), 7.23 (2H, m, Ar), 7.61 (2H, m, Ar)

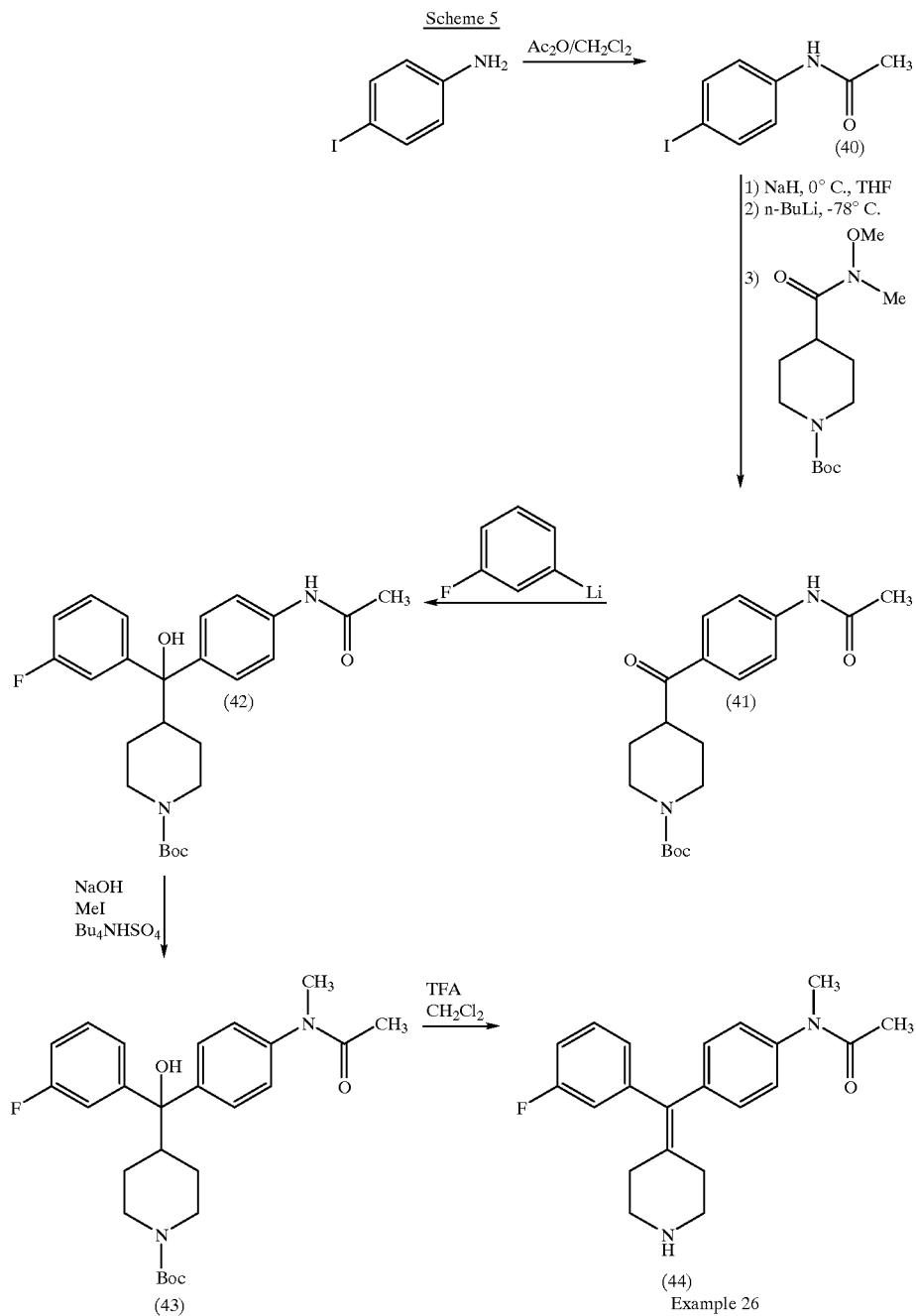

Scheme 5

(i) Preparation of Preparation of 4'-Iodo-acetanilide (compound 40)

To a solution of 4-Iodo-aniline (15 g, 69 mmol) in dry $CH_2Cl_2$ (100 ml) was added acetic anhydride(14.09 g, 138 mmol) at room temperature, the reaction mixture was then (ii) Preparation of 4-(4-acetamidobenzoyl)-N-t-butoxylcarbonylpiperidine (compound 41)

To a solution of 4'-iodo-acetanilide (11.7 g, 45 mmol) in dry THF (200 ml) was added NaH (1.62 g, 67.5 mmol) at 0° C., the reaction mixture was stirred for 30 min while temperature was warming up to room temperature, following by the slow addition of n-BuLi (1.6 M in Heptane, 54 mmol) at −78° C. The mixture was stirred for 15 min then N-t-Butoxylcarbonyl N'-methyl-N'methoxyl-isonipecotamide(6.15 g, 30 mmol) in THF (10 ml) was added dropwise via syringe. The reaction mixture was warmed up to r.t. and then quenched with aqueous NH$_4$Cl solution, and extracted with ethyl acetate (2×100 ml) The organic layer was washed with saturated (aq)NH$_4$Cl, brine, dried over MgSO$_4$ and concentrated to give a crude product, which was further purified by silica gel column chromatography using MeOH—CH$_2$Cl$_2$ (0:100~5:95) to provide the desired product (9.02 g, 87%).

$^1$H NMR: (CDCl$_3$) δ: 1.47 (9H, s (CH$_3$)$_3$), 1.6–1.8 (4H, m, piperidine), 2.21 (3H, s, COCH$_3$), 2.9 (2H, m, piperidine), 3.37 (1H, m, COCH—), 4.15 (2H, m, piperidine), 7.64 (2H, m, Ar), 7.86 (1H, s, br, —CONH), 7.91 (2H, m, Ar)

(iii) Preparation of 4-(α-Hydroxy-α-(4-N-t-butoxylcarbonylpiperidinyl)-3-Fluorobenzyl) acetanilide (compound 42)

Method as described for the preparation of compound 4 but substituting 3-fluoro-1-iodobenzene for 1-bromonaphthalene to give the title compound. (93%)

$^1$H NMR: (DMSO-D$_6$) δ: 1.2–1.3 (4H, m, piperidine), 1.37 (9H, s, (CH$_3$)$_3$), 2.0 (3H, s, COCH$_3$), 2.65 (3H, br, piperidine), 3.95 (2H, m, piperidine), 6.98 (1H, m, Ar), 7.21–7.50 (7H, m, Ar), 9.85 (1H, s, OC—NH)

(iv) Preparation of N-methyl-4-(α-Hydroxy-α-(4-N-t-butoxylcarbonylpiperidinyl)-3-Fluorobenzyl) acetanilide (compound 43)

To a 2M (aq)NaOH solution (10 ml), tetrabutylammonium hydrogen sulphate(1.35 g, 3.97 mmol) was added, followed by the addition of 4-(α-Hydroxy-α-(4-N-t-butoxylcarbonylpiperidinyl)-3-fluorobenzyl)acetanilide (825 mg, 1.86 mmol) and methyl iodide (769 mg, 5.4 mmol) in 10 ml of dichloromethane. The reaction mixture was then refluxed for 1 hr, cooled down to r.t. The dichloromethane layer was collected and evaporated to ~1 ml. Ethyl acetate was added and the precipitate was filtered out. The organic phase was washed with brine and dried over MgSO4, concentrated to give a solid which was further purified by MPLC using MeOH—CH$_2$Cl$_2$ (5:95) as to give the pure titled compound (770 mg, 93%).

$^1$H NMR: (CDCl$_3$) δ:1.2–1.5 (4H, m, piperidin), 1.42 (9H, s, (CH$_3$)$_3$), 1.83 (3H, s, COCH$_3$), 2.52 (1H, m, —CH—C—OH), 2.70 (2H, m, piperidine), 2.86 (1H, s, br, —OH), 3.21 (3H, s, NCH$_3$), 4.15 (2H, s, br, piperidine), 6.90 (1H, m, Ar), 7.12–7.60 (7H, m, Ar)

EXAMPLE 26

Preparation of N-methyl-4-(3-Fluorophenyl-piperidin-4-ylidenemethyl)acetanilide (compound 44)

To a solution of N-methyl-4-(α-Hydroxy-α-(4-N-t-butoxylcarbonylpiperidinyl)-3-fluorobenzyl) acetanilide (300 mg, 0.657 mmol) in dry dichloromethane (5 mL) was added trifluoroacetic acid (5.0 mL) at r.t. The reaction mixture was refluxed for 4 hr., and then condensed. The residue was dissolved in AcOEt (50 ml). The resulting solution was washed with 2 N (aq)NaOH, (aq) NH$_4$Cl and brine, dried over MgSO$_4$. Removal of solvents gave a crude product, which was purified by MPLC eluting with MeOH—CH$_2$Cl$_2$—NH$_4$OH (5:95:1) to provide the pure product (176 mg, 79%). mp. 235–237° C. dec.

IR (NaCl Film): (HCl salt) ν(max.)=2961, 2722, 2480, 1658, 1608, 1580, 1507, 1429, 1381 cm$^{-1}$.

$^1$H NMR: (CDCl$_3$) δ: 1.89 (3H, s, COCH$_3$), 1.95 (1H, s, —NH) 2.32(4H, m, piperazine), 2.92 (4H, m, piperazine), 3.26 (3H, s, N—CH$_3$), 6.81–7.28 (8H, m, Ar) $^{13}$C NMR: (CDCl$_3$) δ: 22.4, 33.2, 33.3, 37.0, 48.3, 113.3(m, C—F), 116.5(m, C—F), 125.4, 126.6, 129.5, 129.6, 130.9, 133.7, 137.7, 141.2, 142.8, 144.2, 161.3, 163.8, 170.4. ANALYSIS: (%)

Anal.Calcd.for: C$_{21}$H$_{23}$N$_2$FO•HCl: C, 67.28; H, 6.45; N, 7.47. Found: C, 66.88; H, 6.44; N, 7.16.

F) Synthetic Scheme for the Preparation of the Compound of Example 27

The compound of Example 27 was prepared by following the procedure as is shown in Scheme 6 below.

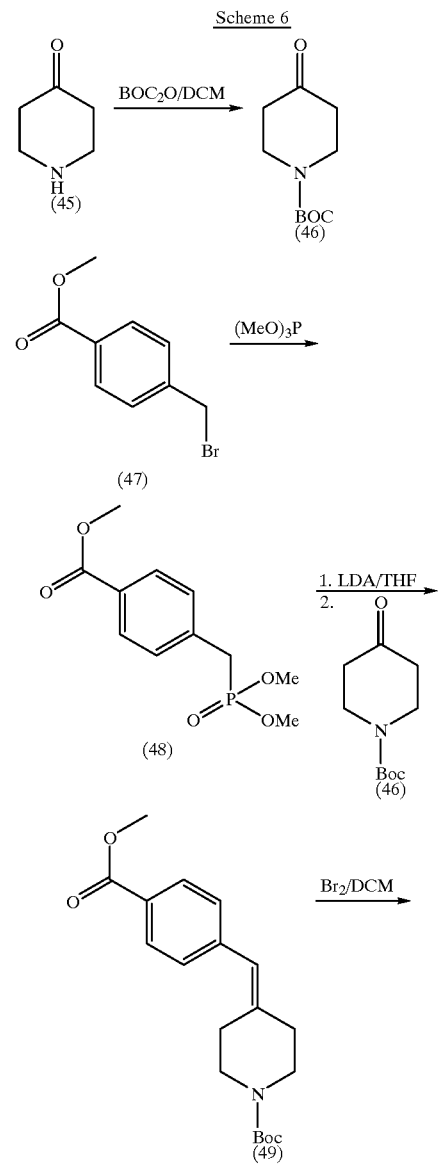

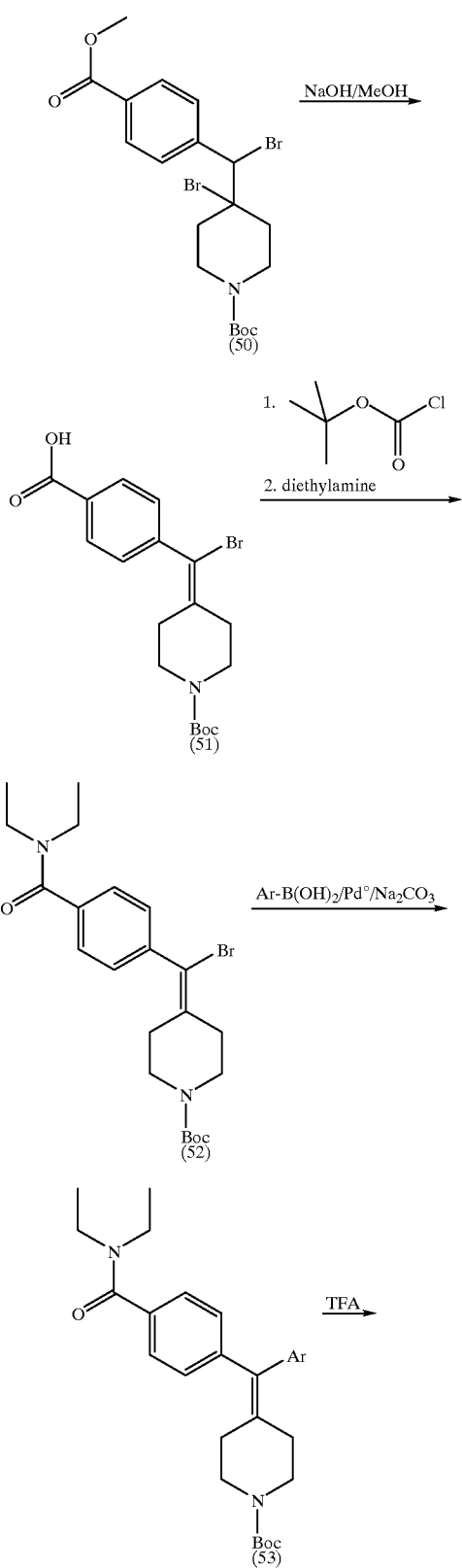

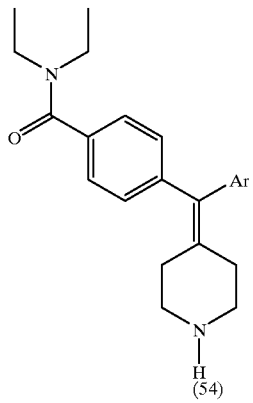

Example 27

(i) Preparation of N-tert-Butoxylcarbonyl-4-piperidone (compound 46)

A mixture of compound 45 (50 g, 0.325 mol) and di-tert-butyl dicarbonate (71 g, 0.325 mol) in 300 mL of dichloromethane were stirred at 0° C. while triethylamine (133 g, 1.32 mol) was added dropwise. The mixture was allowed to warm to room temperature and was stirred for 12 hrs. The solvent was evaporated and the crude product was partitioned between water (400 mL) and diethyl ether (400 mL). The aqueous phase was washed with an additional portion of diethyl ether (400 mL). The combined ether was washed with water (400 mL) and brine (400 mL) dried over $MgSO_4$. Removal of solvent gave compound 46 as a pale yellow solid. (55.3 g, 85%):

$\delta_H$(400 MHz, $CDCl_3$) 1.50 (s, 9H), 2.45 (t, 4H, J=6.1 Hz), 3.72 (t, 4H, J=61 Hz)

(ii) Preparation of 4-(4-Methoxycarbonyl-benzylidene)-piperidine-1-carboxylic acidtert-butyl ester (compound 49)

Methyl 4-(bromomethyl) benzoate (compound 47) (11.2 g, 49 mmol) was dissolved in 25 mL trimethyl phosphite and refluxed under $N_2$ for 5 hrs. Excess trimethyl phosphite was removed by co-distillation with toluene to give crude 4-(Dimethoxy-phosphorylmethyl)-benzoic acid methyl ester (compound 48).

$\delta_H$(400 MHz, $CDCl_3$) 3.20 (d, 2H, J=22 Hz), 3.68 (d, 3H 10.8 Hz), 3.78 (d, 3H, 11.2 Hz), 3.91 (s, 3H), 7.38 (m, 2H), 8.00 (d, 2H, J=8 Hz.

The crude product (compound 48) was dissolved in dry THF (200 mL) under $N_2$ and cooled to −78° C. Lithium diisopropylamide (32.7 mL 1.5 M in hexanes, 49 mmol) was added dropwise. The solution was allowed to warm to room temperature. A solution of compound 46 (9.76 g, 49 mmol in 100 mL dry THF) was added to the reaction dropwise and was stirred under $N_2$ for 12 hrs. Water (300 mL) and ethyl acetate (300 mL) were added to the reaction mixture and extracted. The aqueous phase was washed with ethyl acetate (2×300 mL). The combined ethyl acetate was dried over $MgSO_4$ and evaporated to give a crude product, which was purified by silica gel chromatography (0–33% ethyl acetate in hexanes) to provide compound 49 as a white solid (5.64 g, 35%).

$\delta_H$(400 MHz, $CDCl_3$) 1.44 (s, 1H), 2.31 (t, J=5.5 Hz, 2H), 2.42 (t, J=5.5 Hz, 2H), 3.37 (t, J=5.5 Hz, 2H), 3.48 (t, J=5.5

Hz, 2H), 3.87(s, 3H), 6.33 (s, 1H), 7.20 (d, J=6.7 Hz, 2H), 7.94 (d, J,=6.7 Hz, 2H). $\delta_{c-13}$ (CDCl$_3$) 28.3, 29.2, 36.19, 51.9, 123.7, 127.8, 128.7, 129.4, 140.5, 142.1, 154.6, 166.8 ppm. $v_{max}$(NaCl) cm$^{-1}$ 3424, 2974, 2855, 1718, 1688, 1606, 1427, 1362, 1276.

Analysis calculated for C$_{19}$H$_{25}$NO$_4$: C 68.86%, H 7.60%, N 4.23%; actual: C 69.1%, H7.69%, N 4.25%.

(iii) Preparation of 4-Bromo-4-[bromo-(4-methoxycarbonyl-phenyl)-methyl]-piperidine-1-carboxylic acid tert-butyl ester (compound 50)

To a solution of compound 49 (5.2 g, 16 mmol) in dry dichloromethane (200 mL) was added K$_2$CO$_3$ (1.0 g). A bromine solution (2.9 g, 18 mmol in 30 mL DCM) was then added dropwise at 0° C. and stirred for 1.5 hrs at room temperature. The K$_2$CO$_3$ was removed by filtration and the solvent was evaporated to dryness. The crude product was dissolved in ethyl acetate (200 mL) and washed with water (200 mL), 0.5 M HCl (200 mL) and brine (200 mL), dried over MgSO$_4$. The solvent was evaporated to give crude product which was recrystallized from methanol to give compound 50 as a white solid (6.07 g, 78%).

$\delta_H$(400 MHz, CDCl$_3$) 1.28 (s, 9H), 1.75 (m, 2H), 1.90 (m, 2H), 2.1 (m, 4H), 3.08 (br, 4H), 3.90 (s, 3H), 4.08 (br, 4H), 5.14 (s, 1H), 7.57 (d, J=8.4 Hz, 2H) 7.98 (d, J=8.4 Hz, 2H). $\delta_{c-13}$ (400 MHz, CDCl$_3$) 28.3, 36.6, 38.3, 40.3, 52.1, 63.2, 72.9, 129.0, 130.3, 130.4, 141.9, 154.4, 166.3 ppm. $v_{max}$ (NaC) cm$^{-1}$ 3425,2969, 1725, 1669, 1426, 1365, 1279, 1243.

Analysis calculated for: C$_{19}$H$_{25}$Br$_2$NO$_4$: V46.6%, H 5.13%, N 2.85%; actual: 46.64%, H 5.16%, N 2.89%.

(iv) Preparation of 4-[Bromo-(4-caboxy-phenyl)-methylene]-piperidine-1-carboxylic acid tert-butyl ester (compound 51)

To a solution of compound 50 (5.4 g 11 mmol) in methanol (300 mL) at 40° C. was added 2.0 M NaOH (100 mL). The reaction was stirred for 3 hrs at 40° C. The crude salt was isolated by filtration. The solid was dried overnight en vacuo. The dry salt was dissolved in 40% acetonitrile/water and the pH was adjusted to 2 using concentrated HCl. The desired product (7) (3.8 g, 87%) was isolated as a white powder by filtration.

$\delta_H$(400 MHz, CDCl$_3$) 1.45 (s, 9H), 2.22 (dd, J=5.5 Hz, 6.1 Hz, 2H), 2.64 (dd, J=5.5 Hz, 6.1 Hz, 2H), 3.34 (dd, J=5.5 Hz, 6.1 Hz, 2H), 3.54 (dd, J=5.5 Hz, 6.1 Hz, 2H), 7.35 (d, J=6.7 Hz, 2H), 8.08 (d, J=6.7 Hz, 2H). $\delta_{c-13}$ (400 MHz, CDCl$_3$) 28.3, 31.5, 34.2, 44.0, 115.3, 128.7, 129.4, 130.2, 137.7, 145.2, 154.6, 170.3.

Analysis calculated for: C$_{18}$H$_{22}$BrNO$_4$: C 54.56%, H 5.60%, N 3.53%; actual: C 54.66%, H 5.68%, N 3.59%.

(v) Preparation of 4-[Bromo-(4-diethylcarbamoyl-phenyl)-methylene]-piperidine-1-carboxylic acid tert-butyl ester (compound 52)

To a solution of compound 51 (1.0 g, 2.5 mmol) in dry dichloromethane (10 mL) at -20° C. was added iso-butylchloroformate (450 mg, 3.3 mmol). After 20 min at -20° C. diethylamine (4 mL) was added and the reaction was allowed to warm to room temperature. After 1.5 hrs the solvent was evaporated and the reaction mixture was partitioned between ethyl acetate and water. The ethyl acetate was washed with water and brine and dried over MgSO$_4$ and removed by evaporation. The crude product was purified by silica gel chromatography (0–60% ethyl acetate in heptanes) to give the product (compound 52) as white needles (800 mg, 73%).

$\delta_H$(400 MHz, CDCl3) 1.13 (br, 3H), 1.22 (br, 3H), 1.44 (s, 9H), 2.22 (t, J=5.5 Hz, 2H), 2.62 (t, J=5.5 Hz, 2H), 3.31 (t, J=5.5 Hz, 2H), 3.52 (t, J=5.5 Hz, 2H), 7.27 (d, J=7.9 Hz, 2H), 7.33 (d, J=7.9 Hz, 2H). $\delta_{c-13}$ (400 MHz, CDCl$_3$) 12.71, 14.13, 28.3, 31.5, 34.2, 39.1, 43.2, 79.7, 115.9, 126.3, 129.3, 136.8, 137.1, 140.6, 154.6, 170.5.

Analysis calculated for: C$_{22}$H$_{31}$BrN$_2$O$_3$: C 58.3%, H 6.92%, N6.21%; actual: C 58.62%, 6.89%, 6.21%.

EXAMPLE 27

Preparation of N,N-Diethyl-4-[piperidin-4-ylidene (3-trifluoromethyl-phenyl)-methyl]-benzamide (compound 54, Ar=3-Trifluoromethylphenyl) (general procedure)

The Suzuki coupling of compound 52 with a variety of boronic acids and the subsequent deprotection were performed on a small scale in parallel. The reactions and liquid-liquid extractions were carried out in 25×150 mm culture tubes. The protocol for a typical reaction is outlined below.

To a solution of compound 52 (25 mg, 57 µmol) and Tetrakis(triphenyl phosphine) palladium(0) (5 mg, 4.3 µmol) in xylenes (degassed, 0.5 mL) was added 3-Trifluorophenyl boronic acid (28.5 mg, 150 µmol) in ethanol (degassed, 0.5 mL) followed by 150 µL of 2M Na$_2$CO$_3$ (aq) (300 µmol). The reaction was allowed to procede at 80° C. for 1.5 hrs under Ar. The reaction was diluted with water (1 mL) and diethyl ether (1 mL) and vortexed. The organic phase was isolated and evaporated to give a crude product (compound 9, Ar=3-Trifluoromethylphenyl).

The Boc group was removed by treating the crude product with 1 mL of TFA. After 30 minutes at room temperature the TFA was evaporated to give the crude TFA salt. The salt was neutralized with 1 M NH$_4$OH(1.0 M) and extracted into diethyl ether (2×1 mL). The ether phase was acidified with 4.0 M HCl in dioxane (200 µL) and the HCl salt was extracted into water (2×1 mL). The aqueous salt solution was washed with diethyl ether (2× 1 mL) and lyophilized to yield the product (compound 54, Ar=3-Trifluoromethylphenyl) as a white powder (10 mg, 39%).

$^1$H NMR (CDCl$_3$) (base) δ 1.11 (br, 3H), 1.20 (br, 3H), 2.26 (t, J=5.6 Hz, 2H), 2.31 (t, J=5.6 Hz, 2H), 2.88–2.91 (m, 4H), 3.27 (br, 2H), 3.52 (br, 2H), 7.10–7.47 (m, *H).

Analysis calculated for: C$_{24}$H$_{28}$N$_2$OF$_3$Cl×1.80 H$_2$O: C, 59.39; H, 6.56; N, 5.77; Actual: C, 59.39; H, 5.90; N, 5.77.

EXAMPLES 28–52

By following the same procedure as described for compound 54 of Example 27 but substituting the respective boronic acids for 3-trifluoromethylphenylboronic acid, the following compounds were also prepared.

EXAMPLE 28

N,N-Diethyl-4-(3-nitrophenyl-piperidin-4-ylidene-methyl)-benzamide (compound 55)

3-nitrophenylboronic acid was used.

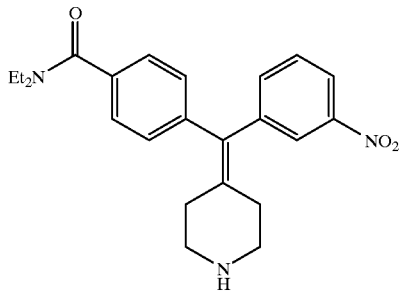

(55)

¹H NMR (CDCl3) (base) δ 1.11 (br, 3H), 1.21 (br, 3H), 2.27–2.34 (m, 4H), 2.92 (t, J=6.0 Hz, 4H), 3.26 (br, 2H), 3.52 (br, 2H), 7.10 (d, J=8.4 Hz, 2H), 7.31 (d, J=8.4 Hz, 2H), 7.40–7.50 (m, 2H), 7.95–8.08 (m, 2H)

EXAMPLE 29

N,N-Diethyl-4-(4-toluyl-piperidin-4-ylidene-methyl)-benzamide (compound 56)

p-toluylboronic acid was used.

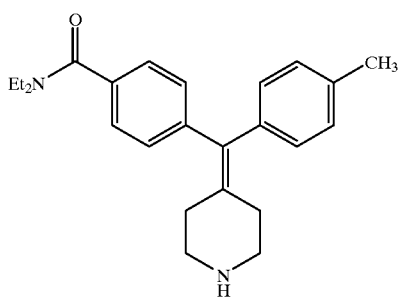

(56)

1H NMR (CDCl3) (base) δ 1.10 (br, 3H), 1.19 (br, 3H), 2.29 (s, 3H), 2.26–2.31 (m, 4H), 2.86–2.88 (m, 4H), 3.25 (br, 2H), 3.49 (br, 2H), 6.95–7.28 (m, 8H)

EXAMPLE 30

N,N-Diethyl-4-(4-formylphenyl-piperidin-4-ylidene-methyl)-benzamide (compound 57)

4-formylphenylboronic acid was used.

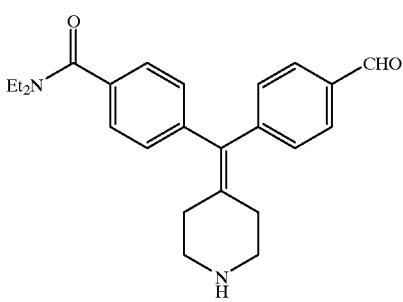

(57)

1H NMR (CDCl3) (base) δ 1.10 (br, 3H), 1.20 (br, 3H), 2.28–2.33 (m, 4H), 2.89–2.92 (m, 4H), 3.25 (br, 2H), 3.50 (br, 2H), 7.08–7.79 (m, 8H), 9.95 (s, 1H)

EXAMPLE 31

N,N-Diethyl-4-(3-chloro-4-fluorophenyl-piperidin-4-ylidene-methyl)-benzamide (compound 58)

3-chloro-4-fluorophenylboronic acid was used.

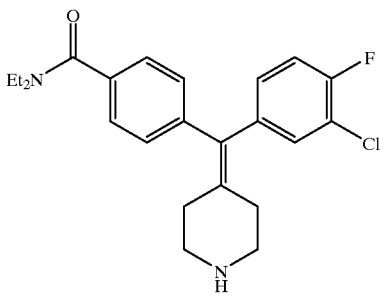

(58)

1H NMR (CDCl₃) (base) δ 1.10 (br, 3H), 1.20 (br, 3H), 2.26–2.30 (m, 4H), 2.86–2.91 (m, 4H), 3.25 (br, 2H), 3.50 (br, 2H), 6.93–7.30 (m, 7H)

EXAMPLE 32

N,N-Diethyl-4-(4-fluorophenyl-piperidin-4-ylidene-methyl)-benzamide (compound 59)

4-fluorophenylboronic acid was used.

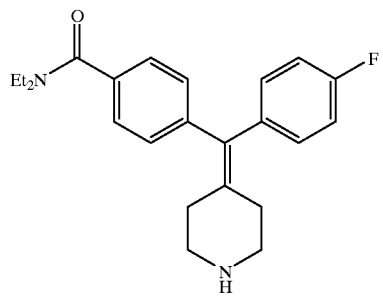
(59)

1HNMR (CDCl$_3$) (base) δ 1.11 (br, 3H), 1.16 (br, 3H), 2.25 (s, 4H), 2.84 (s, 4H), 3.20 (br, 2H), 3.47 (br, 2H), 6.92 (m, 2H), 7.01 (m, 4H), 7.23 (d, J=8.8 Hz, 2H)

EXAMPLE 33

N,N-Diethyl4-(2-fluorophenyl-piperidin4-ylidene-methyl)-benzamide (compound 60)

2-fluorophenylboronic acid was used.

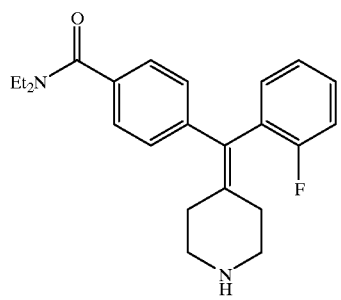
(60)

1H NMR (CDCl3) (base) δ 1.11 (br, 3H), 1.15 (br, 3H), 2.10 (t, J=5.2 Hz, 2H), 2.27 (t, J=5.2 Hz, 2H), 2.83(m, 4H), 3.20 (br, 2H), 3.45 (br, 2H), 6.94–7.03 (m, 3H), 7.10–7.23 (m, 5H)

EXAMPLE 34

N,N-Diethyl-4-(2,4-dichlorophenyl-piperidin-4-ylidene-methyl)-benzamide (compound 61)

2,4-dichlorophenylboronic acid was used.

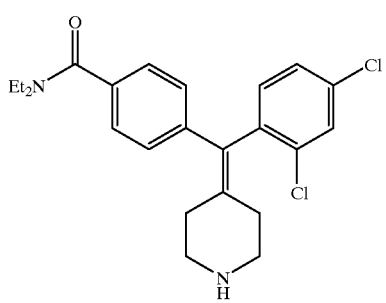
(61)

1H NMR (DMSO) (HCl salt) δ 1.07 (br, 6H), 2.24 (t, 2H), 2.50 (t, 2H), 3.10 (t, 2H), 3.30 (t, 2H), 3.31 (br, 2H), 3.43 (br, 2H), 7.25 (d, J=8.4 Hz, 2H), 7.32 (d, J=8.4 Hz, 2H), 7.43 (d, J=8.0 Hz, 1H), 7.47 (d, J=8.0 Hz, 1H), 7.68 (s, 1H), 9.20 (br, 2H)

EXAMPLE 35

N,N-Diethyl-4-(3,5-dichlorophenyl-piperidin-4-ylidene-methyl)-benzamide (compound 62)

3,5-dichlorophenylboronic acid was used.

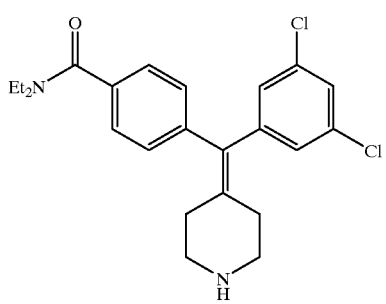
(62)

1H NMR (DMSO) (HCl salt) δ 1.03 (br, 6H), 2.36–2.38 (m, 4H), 3.0–3.2 (m, 4H), 3.2 (br, 2H), 3.38 (br, 2H), 7.19 (s, 1H), 7.21 (d, J=8.0 Hz, 2H), 7.29 (d, J=8.0 Hz, 2H), 7.49 (s, 2H), 9.10 (br, 2H)

EXAMPLE 36

N,N-Diethyl-4-(3-acetylphenyl-piperidin-4-ylidene-methyl)-benzamide (compound 63)

3-acetylphenylboronic acid was used.

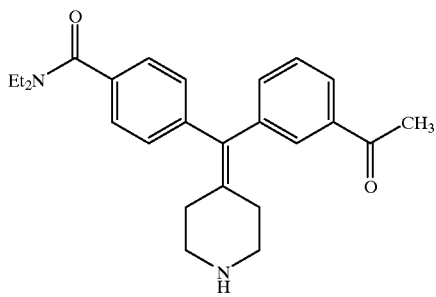

(63)

1H NMR (CDCl3) (base) δ 1.11 (br, 3H), 1.20 (br, 3H), 2.26 (t, J=5.6 Hz, 2H), 2.32 (t, J=5.6 Hz, 2H), 2.55 (s, 3H), 2.92–2.88 (m, 4H), 3.26 (br, 2H), 3.51 (br, 2H), 7.11 (d, J=8.0 Hz, 2H), 7.29 (d, J=8.0 Hz, 2H), 7.29 (d, J=7.2 Hz, 1H), 7.37 (t, J=8.0 Hz, 1H), 7.70 (s, 1H), 7.79 (d, J=7.2 Hz, 1H)

EXAMPLE 37

N,N-Diethyl-4-(3,5-trifluoromethylphenyl-piperidin-4-ylidene-methyl)-benzamide (compound 64)

3,5-trifluoromethylphenylboronic acid was used.

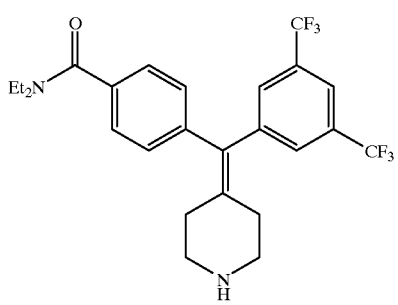

(64)

1H NMR (DMSO) (HCl salt) δ 1.06 (br, 3H), 1.08 (br, 3H), 2.33 (br, 2H), 2.41 (br, 2H), 3.12 (br, 6H), 3.38 (br, 2H), 7.24 (d, J=7.6 Hz, 2H), 7.30 (d, J=7.6 Hz, 2H), 7.84 (s, 2H), 8.00 (s, 2H), 8.9 (br, 2H)

EXAMPLE 38

N,N-Diethyl-4-(3-thiophenyl-piperidin-4-ylidene-methyl)-benzamide (compound 65)

3-thiophenylboronic acid was used.

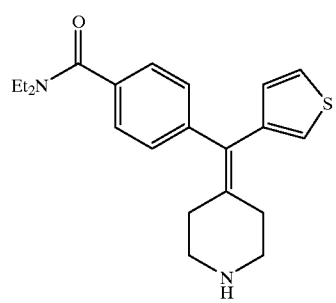

(65)

1HNMR (DMSO) (HCl salt) δ 1.10 (br, 6H), 2.44 (t, 2H), 2.58 (t, 2H), 3.10–3.15 (m, 4H), 3.21 (br, 2H), 3.44 (br, 2H), 6.86 (d, J=4.8 Hz, 1H), 7.20 (d, J=8.0 Hz, 2H), 7.32 (d, J=8.0 Hz, 2H), 7.33 (s, 1H), 7.52 (d, J=4.8 Hz, 1H)

EXAMPLE 39

N,N-Diethyl-4-(2-thiophenyl-piperidin-4-ylidene-methyl)-benzamide (compound 66)

2-thiophenylboronic acid was used.

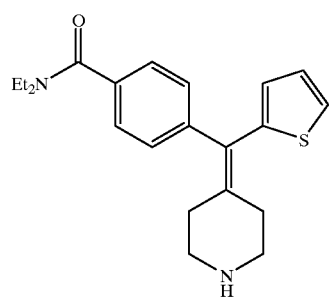

(66)

1H NMR (CDCl3) (base) δ 1.12 (br, 3H), 1.20 (br, 3H), 2.24 (t, J=5.2 Hz, 2H), 2.50 (t, J=5.2 Hz, 2H), 2.85 (t, J=5.6 Hz, 2H), 2.92 (t, J=5.6 Hz, 2H), 3.27 (br, 2H, 3.51 (br, 2H), 6.75 (d, J=3.6 Hz, 1H), 6.93 (t, J=3.6 Hz, 1H), 7.16 (d, J=7.2 Hz, 2H), 7.21 (d, J=3.6 Hz, 1H), 7.30 (d, J=7.2 Hz, 2H)

EXAMPLE 40

N,N-Diethyl-4-(4-methylthiophenyl-piperidin-4-ylidene-methyl)-benzamide (compound 67)

4-methylthiophenylboronic acid was used.

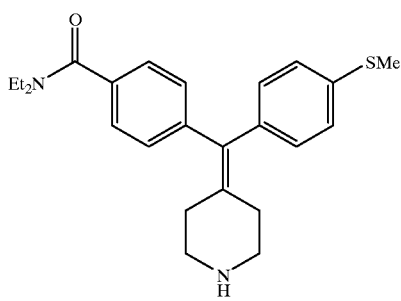
(67)

1H NMR (CDCl3) (base) δ 1.11 (br, 3H), 1.20 (br, 3H), 2.32–2.75 (m, 4H), 2.45 (s, 3H), 2.90–2.87 (m, 4H), 3.26 (br, 2H), 3.51 (br, 2H), 7.01 (d, J=6.0 Hz, 2H), 7.10 (d, J=6.0 Hz, 2H), 7.15 (d, J=6.8 Hz, 2H), 7.27 (d, J=6.8 Hz, 2H)

EXAMPLE 41

N,N-Diethyl-4-(3-aminophenyl-piperidin-4-ylidene-methyl)-benzamide (compound 68)

3-aminophenylboronic acid was used.

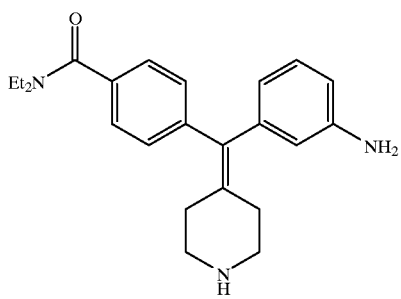
(68)

1H NMR (CDCl3) (base) δ 1.11 (br, 3H), 1.20 (br, 3H), 2.27–2.33 (m, 4H), 2.86–2.90 (m, 4H), 3.27 (br, 2H), 3.51 (br, 2H), 3.57 (br, 2H), 3.68 (s, 1H), 6.39 (s, 1H), 6.52 (dd, J=1.6 Hz, J=7.6 Hz, 2H), 7.06 (t, J=8.0 Hz, 1H), 7.12 (d, J=6.4 Hz, 2H), 7.26 (d, J=6.4 Hz, 2H)

EXAMPLE 42

N,N-Diethyl-4-(4-trifluoromethylphenyl-piperidin-4-ylidene-methyl)-benzamide (compound 69)

4-trifluoromethylphenylboronic acid was used.

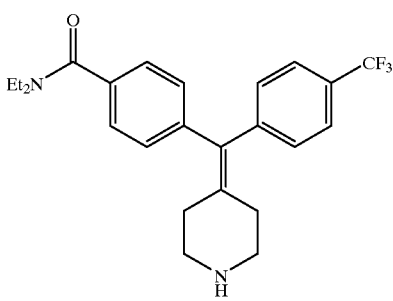
(69)

1H NMR(DMSO) (HCl salt) δ 1.05 (br, 6H), 2.35 (t, 2H), 2.40 (t, 2H), 3.09 (m, 6H), 3.35 (br, 2H), 7.17 (d, J=8.0 Hz, 2H), 7.28 (d, J=8.0 Hz, 2H), 7.35 (d, J=8.0 Hz, 2H), 7.67 (d, J=8.0 Hz, 2H), 8.71 (br, 2H)

EXAMPLE 43

N,N-Diethyl-4-(4-methoxyphenyl-piperidin-4-ylidene-methyl)-benzamide (compound 70)

4-methoxyphenylboronic acid was used.

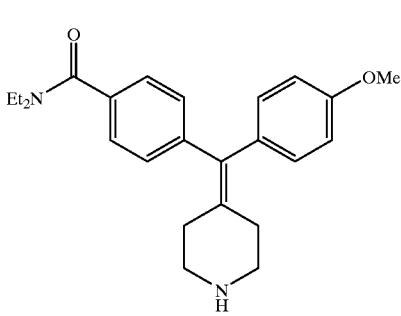
(70)

1H NMR (CDCl3) (base) δ 1.12 (br, 3H), 1.19 (br, 3H), 2.29 (m, 4H), 2.87 (m, 4H), 3.27 (br, 2H), 3.51 (br, 2H), 3.77 (s, 3H), 6.80 (m, 2H), 7.00 (m, 2H), 7.10 (d, J=8.4 Hz, 2H), 7.26 (d, J=8.4 Hz)

EXAMPLE 44

N,N-Diethyl4-(3,4-dichlorophenyl-piperidin-4-ylidene-methyl)-benzamide (compound 71)

3,4-dichlorophenylboronic acid was used.

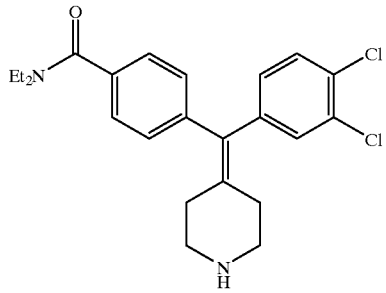
(71)

1H NMR (CDCl3) (base) δ 1.12 (br, 3H), 1.20 (br, 3H), 2.28 (t, J=5.6 Hz, 4H), 2.89 (m, 4H), 3.27 (br, 2H), 3.52 (br, 2H), 6.8–7.4 (m, 7H)

EXAMPLE 45

N,N-Diethyl-4-(2-trifluoromethylphenyl-piperidin-4-ylidene-methyl)-benzamide (compound 72)

2-trifluoromethylphenylboronic acid was used.

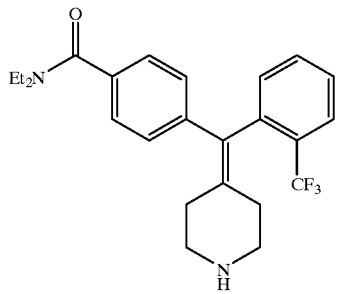
(72)

1H NMR (CDCl3) (base) δ 1.05 (br, 3H), 1.16 (br, 3H), 1.95 (m, 2H), 2.35–2.41 (m, 2H), 2.7–2.9 (m, 4H), 3.20 (br, 2H), 3.48 (br, 2H), 7.2–7.6 (m, 8H)

EXAMPLE 46

N,N-Diethyl-4-(3-toluyl-piperidin-4-ylidene-methyl)-benzamide (compound 73)

m-tolylboronic acid was used.

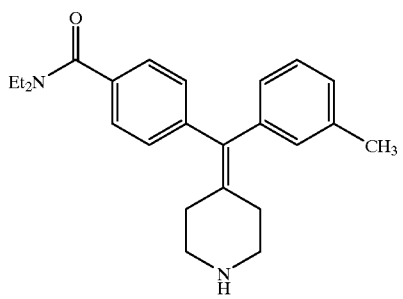
(73)

1H NMR (CDCl3) (base) δ 1.11 (br, 3H), 1.19 (br, 3H), 2.28 (s, 3H), 2.29 (m, 4H), 2.89 (m, 4H), 3.27 (br, 2H), 3.51 (br, 2H), 6.8–7.3 (m, 8H)

EXAMPLE 47

N,N-Diethyl-4-(2-methoxyphenyl-piperidin-4-ylidene-methyl)-benzamide (compound 74)

2-methoxyphenylboronic acid was used.

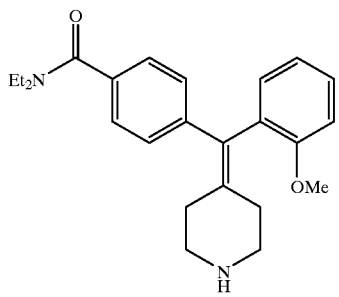
(74)

1H NMR (CDCl3) (base) δ 1.09 (br, 3H), 1.18 (br, 3H), 2.10 (q, J=4.8 Hz, 2H), 2.31 (q, ƒ=4.8 Hz, 2H), 2.8–2.9 (m, 4H), 3.25 (br, 2H), 3.50 (br, 2H), 3.68 (s, 3H), 6.83–6.90 (m, 2H), 7.0 (d, 1H), 7.15–7.25 (m, 5H)

EXAMPLE 48

N,N-Diethyl-4-(3-formylphenyl-piperidin-4-ylidene-methyl)-benzamide (compound 75)

3-formylphenylboronic acid was used.

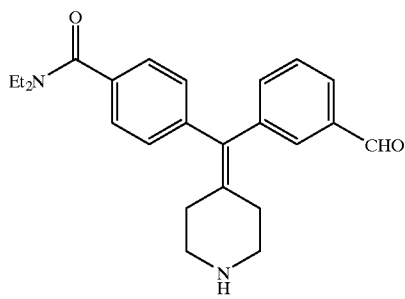
(75)

1H NMR (CDCl3) (base) δ 1.15 (br, 3H), 1.20 (br, 3H), 2.26–2.34 (m, 4H), 2.90–2.92 (m, 4H), 3.28 (br, 2H), 3.2 (br, 2H), 7.11–7.31 (m, 8H), 9.96 (s, 1H)

EXAMPLE 49

N,N-Diethyl-4-(2-naphtyl-piperidin-4-ylidene-methyl)-benzamide (compound 76)

2-naphtylboronic acid was used.

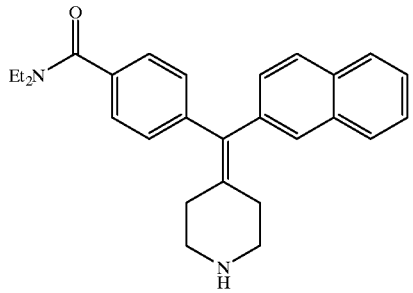
(76)

1H NMR (CDCl3) (base) δ 1.11 (br, 3H), 1.20 (br, 3H), 2.35–2.39 (m, 4H), 2.91–2.96 (m, 4H), 3.27 (br, 2H), 3.51 (br, 2H), 7.16–7.40 (m, 5H), 7.42–7.44 (m, 2H), 7.57 (s, 1H), 7.72–7.79 (m, 2H)

EXAMPLE 50

N,N-Diethyl-4-(2-formylphenyl-piperidin-4-ylidene-methyl)-benzamide (compound 77)

2-formylphenylboronic acid was used.

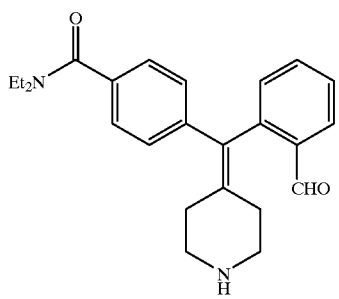
(77)

1H NMR (CDCl3) (base) δ 1.09 (br, 3H), 1.18 (br, 3H), 1.70–2.10 (m, 2H), 2.40–2.49 (m, 2H), 2.76–2.84 (m, 2H), 2.85–2.97 (m, 2H), 3.23 (br, 2H), 3.48 (br, 2H), 7.13–7.40 (m, 6H), 7.53–7.55 (m, 1H), 7.90 (d, J=7.6 Hz, 1H), 10.27 (s, 1H)

EXAMPLE 51

N,N-Diethyl-4-(4-acetylphenyl-piperidin-4-ylidene-methyl)-benzamide (compound 78)

4-acetylphenylboronic acid was used.

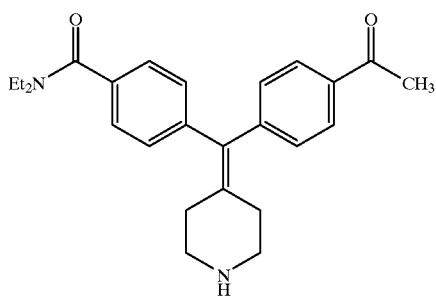
(78)

1H NMR (CDCl3) (base) δ 1.11 (br, 3H), 1.20 (br, 3H), 2.30–2.35 (m, 4H), 2.56 (s, 3H), 2.92 (m, 4H), 3.27 (br, 2H), 3.52 (br, 2H), 7.10–7.30 (m, 6H), 7.87 (d, J=7.2 Hz, 2H)

EXAMPLE 52

N,N-Diethyl-4-(3-trifluoromethylphenyl-piperidin-4-ylidene-methyl)-benzamide (compound 79)

3-trifluoromethylphenylboronic acid was used.

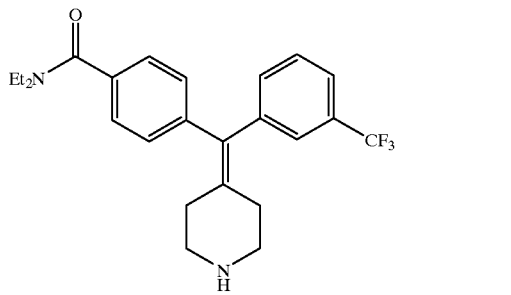

(79)

1H NMR (CDCl3) (base) δ 1.11 (br, 3H), 1.20 (br, 3H), 2.26 (t, J=5.6 Hz, 2H), 2.31 (t, J=5.6 Hz, 2H), 2.88–2.91 (m, 4H), 3.27 (br, 2H), 3.52 (br, 2H), 7.10–7.47 (m, 8H)

EXAMPLE 53

Preparation of N,N-Diethyl-4-([1-(2,6-Diamino-hexanoyl)-piperidin-4-ylidene]-phenyl-methyl)-benzamide (compound 80)

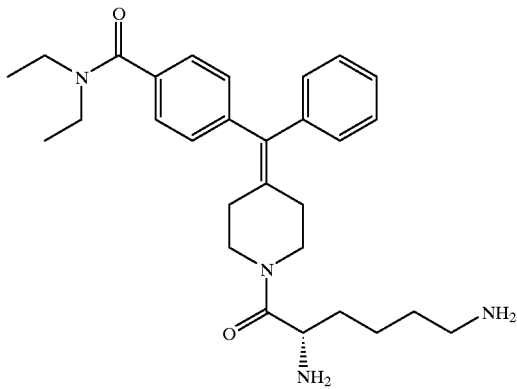

(80)

L-Boc-Lysine(Cbz) (0.38 g, 1.0 mmol) was dissolved in dry tetrahydrofuran (5 mL) under nitrogen at −15° C. N-Methylmorpholine (0.1 mL, 1.0 mmol) then isobutyl chloroformate (0.13 mL, 1 mmol) was added. After stirring 10 minutes, N,N-Diethyl-4-(phenyl-piperidin-4-ylidene-methyl)-benzamide (compound 6) (0.35 g, 1.0 mmol) was added in tetrahydrofuran (1 mL) and the temperature was allowed to rise to 25° C. for 2 h. The reaction mixture was evaporated onto silica gel. MPLC on silica gel (0 to 100% ethyl acetate in heptane) gave 0.4 g.

The product (0.40 g, 0.56 mmol) was dissolved in methylene chloride (10 mL) and treated with trifluoroacetic acid (3 mL) for 30 min, then the volatiles were evaporated. The residue was dissolved in acetic acid (25 mL) and subjected to hydrogenolysis 1.5 h with hydrogen (1 atm) over palladium on carbon (10%, 0.10 g). The solvent was evaporated and the residue purified by chromatography on a short reverse phase (RP-18) column, eluting with 0 to 30% acetonitrile in water. The free amine was extracted with 5% potassium carbonate/methylene chloride to give 123 mg and then treated with two equivalents of hydrochloric acid in methanol/water. Lyophilization gave the dihydrochloride salt.

$^1$H NMR: (free amine, CD$_3$OD): δ=1.0–1.7(m, 16H, amide-Me, piperidine-H, lysine-H), 2.3–2.7 and 3.0–4.5 (m, 11H, amide-H, piperidine-H, lysine-H),4.8 (s, 4H, 2 NH$_2$), 7.10–7.50 (m, 9H, Ar—H). C$_{29}$H$_{40}$N$_4$O$_2$×2.4H$_2$O×2 HCl, requires: C:58.76, H:7.96, N:9.43. Found C:58.70, H:7.51, N:9.33.

EXAMPLE 54

Preparation of 4-[(4-Diethylcarbamoyl-phenyl)-phenyl-methylene]-piperidine-1-carboxylic acid phosphono-oxymethyl ester Compound 81)

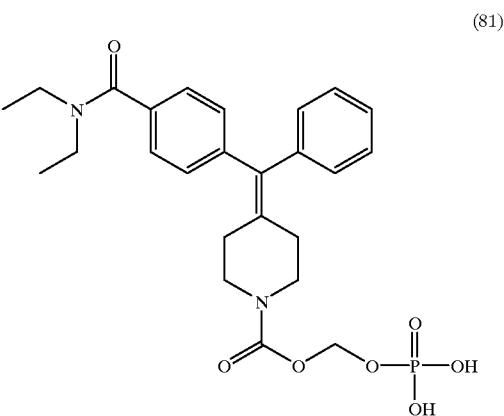

(81)

N,N-Diethyl-4-(phenyl-piperidin-4-ylidene-methyl)-benzamide (compound 6) (0.62 g, 1.8 mmol) was dissolved in methylene chloride (10 mL) and 1,8-bisdiaminonaphtalene (0.42 g, 2.0 mmol) was added. The solution was cooled to 0° C. and chloromethyl chloroformate (0.25 g, 2.0 mmol) added dropwise in methylene chloride (1 mL). After 2 h at 25° C., a further portion of first 1,8-bisdiaminonaphtalene (0.21 g, 1.0 mmol), then chloromethyl chloroformate (0.12 g, 1.0 mmol) was added. After a total of 4 hours, the solution was washed with 1 M HCl, brine and dried (MgSO$_4$) and evaporation gave 0.62 g. The residue was dissolved in toluene (25 mL), silver dibenzylphosphate (0.81 g, 2.1 mmol) was added and the mixture was heated 3 h at 80° C. The solution was filtered, then washed with 5% potassium carbonate solution, brine, dried (K$_2$CO$_3$) and evaporated. MPLC on silica gel (0 to 100% ethyl acetate in heptane) gave 0.66 g (0.96 mmol, 54%). The residue was dissolved in ethyl acetate (50 mL) and subjected to hydrogenolysis (1 atm hydrogen) with palladium on carbon (10%, 0.3 g) for 2 h. After filtration and evaporation of the solvent, the product was treated with two equivalents of sodium hydroxide in methanol/water. Lyophilization gave the disodium salt of the product as a white solid.

$^1$H NMR: (D$_2$O): δ=1.03, 1.20 (2m, 6H, amide-Me), 2.34 (m, 4H, piperidine-H), 3.19–3.61 (m, 8H, amide-CH$_2$, piperidine-H), 5.44 (d, J=13 Hz, 2H, OCH$_2$O), 7.18–7.36 (m, 9H, Ar—H).

Compounds 80 and 81 respectively, are suitable prodrugs of the compounds of the general formula (I).

G) Synthetic Scheme for the Preparation of the Compounds of Examples 55–57

The compounds of Examples 55, 56 and 57 were prepared by following the procedure of Scheme 7 below.

Scheme 7

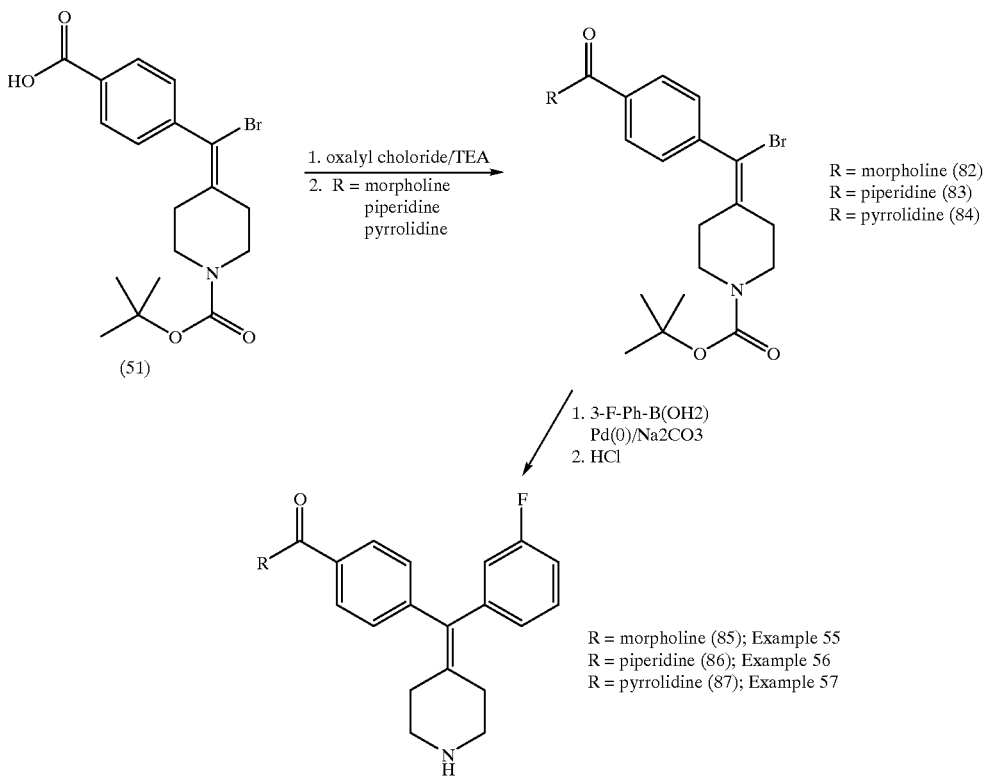

R = morpholine (85); Example 55
R = piperidine (86); Example 56
R = pyrrolidine (87); Example 57

(i) Preparation of tert-butyl-4-{bromo[4-(morpholinocarbonyl)phenyl]methylene}-1-piperidinecarboxylate (compound 82)

To a solution of compound 51, prepared according to scheme 6, (0.25 g, 0.625 mmole) and freshly distilled triethylamine (0.5 mL) in dichloromethane (12 mL), was added oxalyl chloride (0.38 mL 2.0 M, 0.75 mmole) dropwise at room temperature. The solution was stirred for 10 minutes at room temperature and the solvent and excess reagents were removed in vacuo to give the acid chloride as a crude product which was used in the next step without further purification.

Morpholine (56 mg, 0.65 mmole) was added to a solution of the acid chloride (0.65 mmole) and triethylamine (0.5 mL) in dichloromethane (5 mL). The reaction was allowed to proceed for one hour at room temperature. The solvent was then removed in vacuo. The crude product was partitioned between ethyl acetate (25 mL) and water (25 mL). The water was washed with ethyl acetate and the combined ethyl acetate was washed with 2M NaOH (2–25 mL), (2M HCl (2–25 mL), brine (1–25 mL) and dried over magnesium sulfate. The solvent was removed in vacuo to give the product (compound 82) (294 mg, 97% yield).

$^1$H nmr CDCl$_3$ (400 MHz) 1.44 (s, 9H), 2.21 (t, J=5.6 Hz, 2H), 2.62 (t, J=5.6 Hz, 2H), 3.31 (t, J=5.6 Hz, 2H), 3.52 (t, J=5.6 Hz, 2H), 3.69 (br, 8H), 7.31 (d, J=6.4 Hz, 2H), 7.37 (d, J=6.4 Hz, 2H).

(ii) Preparation of tert-butyl-4-{bromo[4-(piperidinocarbonyl)phenyl]methylene}-1-piperidinecarboxylate (compound 83)

Same procedure as described for the preparation of compound 82, but using piperidine in place of morpholine.

$^1$H nmr CDCl$_3$ (400 MHz) 1.44 (s, 9H), 1.51 (br, 2H), 1.66 (br, 4H), 2.21 (t, J=5.6 Hz, 2H), 2.62 (t, J=5.6 Hz, 2H), 3.31 (t, J=5.6 Hz, 2H), 3.33(br, 2H), 3.52 (t, J=5.6 Hz, 2H), 3.68 (br, 2H), 7.26 (d, J=8.4 Hz, 2H), 7.35 (d, J=8.4 Hz, 2H)

(iii) Preparation of tert-butyl-4-{bromo[4-(tetrahydro-1H-1-pyrrolylcarbonyl)phenyl]methylene}-1-piperidinecarboxylate (compound 84)

Same procedure as described for the preparation of compound 82, but using pyrrolidine in place of morpholine.

$^1$H nmr CDCl$_3$ (400 MHz) 1.44 (s, 9H), 1.87 (q, J=6.8 Hz, 2H), 1.95 (q, J=6.8 Hz, 2H), 2.20 (t, J=5.6 Hz, 2H), 2.62 (t, J=5.6 Hz, 2H), 3.31 (t, J=5.6 Hz, 2H), 3.43 (t, J=6.8 Hz, 2H), 3.52 (t, J=5.6 Hz, 2H), 3.63 (t, J=6.8 Hz, 2H), 7.27 (d, J=8.0 Hz, 2H), 7.47 (d, J=8.0 Hz, 2H)

EXAMPLE 55

Preparation of 4-[(3-fluorophenyl)-piperidin-4-yl-methyl]-phenyl-morpholin-4-yl-methanone (compound 85)

To a solution of compound 82 (37 mg, 0.082 mmol) and tetrakis(triphenyl phosphine) palladium(0) (5 mg, 0.0043 mmol) in xylenes (degassed, 0.5 mL) was added 3-fluorophenyl boronic acid (25 mg, 0.18 mmol) in ethanol (degassed, 0.5 mL) followed by 150 μL 2M Na$_2$CO$_3$ (aq) (300 μmol). The reaction was allowed to proceed at 80° C. for 2 hrs under argon. The reaction was diluted with water (1 mL) and diethyl ether (1 mL) and vortexed. The organic phase was isolated and evaporated to give a crude product which was used without further purification.

The Boc group was removed by treating the crude product with 1 mL of TFA. After 30 minutes at room temperature the TFA was evaporated to give the crude TFA salt. The salt was neutralized with 1 M NH$_4$OH (1.0 M) and extracted into diethyl ether (2×1 mL). The ether phase was acidified with 4.0 M HCl in dioxane (200 μL) and the HCl salt was extracted into water (2×1 mL). The aqueous salt solution was washed with diethyl ether (2×1 mL) and lyophilized to yield the product as a white powder.

$^1$H NMR CDCl$_3$ (400 MHz) δ 2.67 (m, 4H), 3.19 (m, 4H), 3.45 (br, 2H), 3.68 (br, 6H), 6.75 (d, J=9.6 Hz, 1H), 6.85 (d, J=8.0 Hz, 1H), 6.95 (m, 1H), 7.11 (d, J=7.6 Hz, 2H), 7.25 (s, 1H), 7.35 (d, J=7.6 Hz, 2H).

EXAMPLE 56

Preparation of 4-[(3-fluorophenyl)-piperidin-4-yl-methyl]-phenyl-piperdin-1-yl-methanone (compound 86)

Same procedure as described for the preparation of compound 85, but using compound 83 as starting material.

$^1$H NMR CDCl$_3$ (400 MHz) δ 1.51 (br, 2H), 1.65 (br, 4H), 2.60 (br, 4H), 3.14 (br, 4H), 3.33 (br, 2H), 3.68 (br, 2H), 6.76 (d, J=8.0 Hz, 1H), 6.86 (d, J=8.0 Hz, 1H), 6.93 (t, J=8.0 Hz, 1H), 7.08 (d, J=8.4 Hz, 2H), 7.25 (s, 1H), 7.32 (d, J=8.4 Hz, 2H).

$^1$H NMR CDCl$_3$ (400 MHz) δ 1.84–1.89 (m, 2H), 1.90–1.98 (m, 2H), 2.60–2.63 (m, 4H), 3.13–3.17 (m, 4H), 3.41 (t, J=6.8 Hz, 2H), 3.62 (t, J=6.8 Hz), 6.73 (d, J=8.8 Hz, 1H), 6.86 (d, J=7.2 Hz, 1H), 6.93 (m, 1H), 7.10 (d, J=8.0 Hz, 2H), 7.25 (s, 1H), 7.45 (d, J=8.0 Hz, 2H).

H) Synthetic Scheme for the Preparation of the Compounds of Examples 58–68

The compounds of Examples 58–68 were prepared by following the procedure of Scheme 8(a)–(c) below.

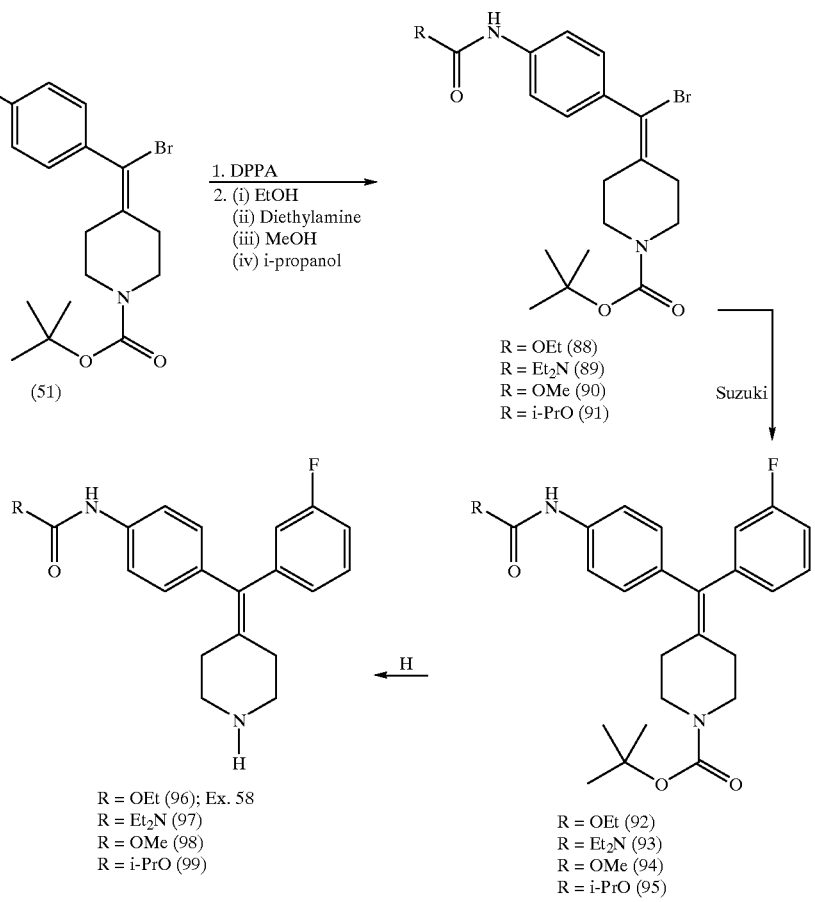

EXAMPLE 57

Preparation of 4-[(3-fluorophenyl)-piperidin-4-yl-methyl]-phenyl-pyrolidin-1-yl-methanone (compound 87)

Same procedure as for the preparation of compound 85, but using compound 84 as starting material.

Scheme 8(b)
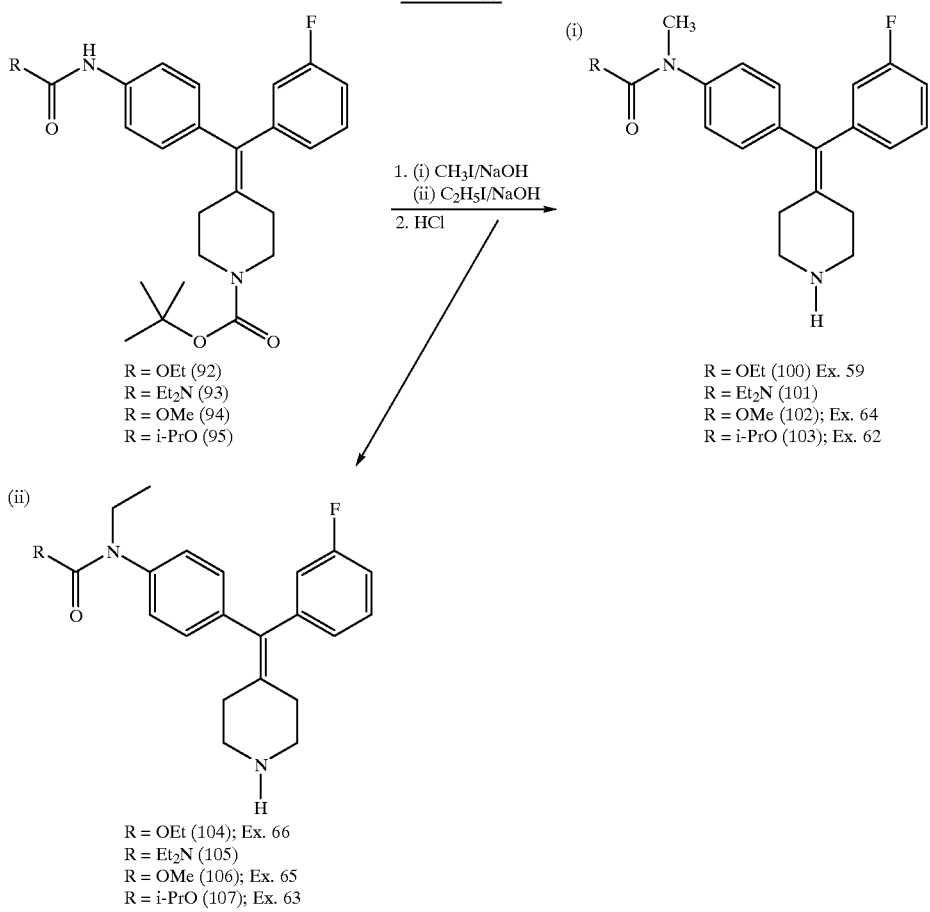
Scheme 8(c)
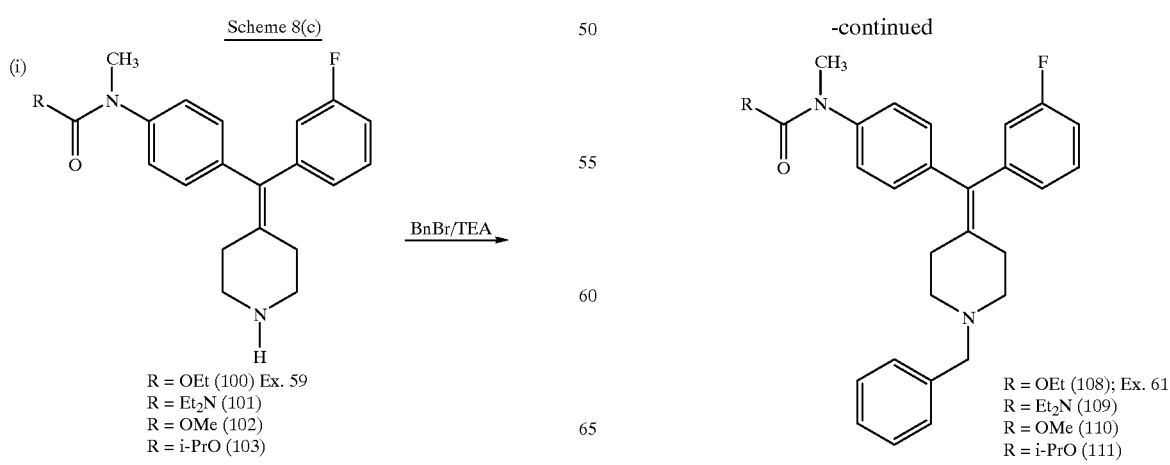

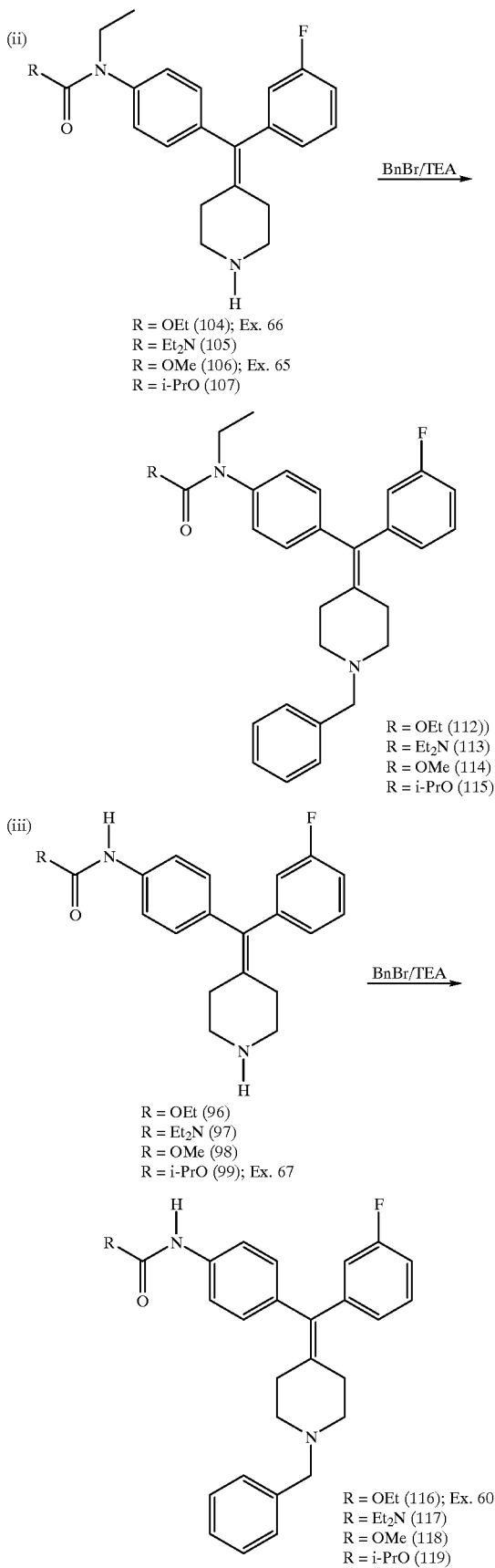

(i) Preparation of 4-[Bromo-(4-ethoxycarbonylaminophenyl)-methyl]-piperidine-1-carboxylic acid tert-butyl ester (compound 88)

To a mixture of compound 51, prepared according to Scheme 6, (0.25 g, 0.625 mmole) in toluene (5 mL), was added diphenylphosphorylazide (0.192 g, 0.70 mmole) and triethyl amine (0.1 mL, 0.7 mmole). After stirring the mixture under argon at 95° C. for two hours an excess of anhydrous ethanol (2 mL) and triethylamine (0.1 mL) were added and the solution was stirred at 95° C. for an additional 5 hours. After cooling to room temperature the reaction mixture was partitioned between water and diethyl ether. The ether was washed with water, dried over magnesium sulfate and removed in vacuo to give the product (compound 88) as a tan foam (300 mg, 99% yield).

$^1$H NMR (400 MHz) (CDCl$_3$) 1.30 (t, J=7.2 Hz, 3H), 1.44 (s, 9H), 2.22 (t, J=6.0 Hz, 2H), 2.60 (t, J=6.0 Hz, 2H), 3.31 (t, J=6.0 Hz, 2H), 3.51 (t, J=6.0 Hz, 2H), 4.21 (q, J=7.2 Hz, 2H), 6.58 (s, 1H), 7.19 (d, J=8.4 Hz, 2H), 7.33 (d, J=8.4 Hz, 2H).

(ii) Preparation of 4-[(4-ethoxycarbonylaminophenyl)-(3-fluorophenyl)-methyl]-piperidine-1-carboxylic acid tert-butyl ester (compound 92)

The Suzuki coupling of the four vinyl bromides (compounds 88–91) with 3-fluorophenyl boronic acid was performed in parallel. The reactions and liquid—liquid extractions were carried out in 25 mm×150 mm culture tubes. The protocol for a typical reaction is outlined below.

To a solution of compound 88 (0.30 g, 0.625 mmoles) and tetrakis(triphenyl phosphine), palladium(0) (50 mg) in toluene (degassed, 5 mL) was added 3-fluorophenyl boronic acid (0.182 g, 1.3 mmoles) in ethanol (degassed, 5 mL) followed by 0.75 mL 2M Na$_2$CO$_3$ (aq) (1.5 mmoles). The reaction was allowed to proceed at 80° C. for 3 hrs under argon. The reaction was diluted with water and diethyl ether and vortexed. The organic phase was isolated and evaporated to give a crude product. The crude product was purified by silica gel chromatography (0–50% EtOAc in hexanes) to give the product (compound 92) as a white powder (0.166 g, 58% yield).

$^1$H NMR (400 MHz) (CDCl$_3$) δ 1.25 (t, J=7.2 Hz, 3H), 1.44 (s, 9H), 2.27–2.33 (m, 4H), 3.41–3.44 (m, 4H), 4.20 (q, J=7.2 Hz, 2H), 6.52 (s, 1H), 6.76 (d, J=10 Hz, 2H), 6.85–6.89 (m, 2H), 7.01 (d, J=8.8 Hz, 2H), 7.19–7.23 (m, 1H), 7.28 (d, J=8.8 Hz, 2H)

EXAMPLE 58

Preparation of 4-[(3-fluorophenyl)-piperidin-4-yl-methyl]-phenyl-carbamic acid ethyl ester (compound 96)

The removal of the BOC protecting group was performed on a small scale in parallel in test tubes (13 mm×100 mm). A typical procedure is described below.

The BOC group was removed by treating compound 92 (50 mg, 0.11 mmole) with HCl in dioxane (4.0 M, 2 mL). The mixture was stirred at room temperature for 30 mixutes. The solvent and HCl were removed in vacuo to yield the product compound 96 as a white powder after lyophilization (40 mg, 99% yield).

$^1$H NMR (400 MHz) (CDCl$_3$) δ 1.28 (t, J=7.2 Hz, 3H), 2.27–2.31 (m, 4H), 2.85–2.91 (m, 4H), 4.19 (q, J=7.2 Hz, 2H), 6.50 (s, 1H), 6.76 d, J=10 Hz, 1H), 6.85–6.89 (m, 2H), 7.01 (d, J=8.8 Hz, 2H), 7.19–7.23 (m, 1H), 7.28 (d, J=8.8 Hz, 2H).

EXAMPLE 59

Preparation of 4-[(3-fluorophenyl)-piperidin-4-yl-methyl]-phenyl-methyl carbamic acid ethyl ester (compound 100)

The alkylation of the amide nitrogen was performed on a small scale in parallel in test tubes (13 mm×100 mm). A typical procedure is outline below.

To a solution of compound 92 (50 mg, 0.11 mmoles) in dichloromethane (1.5 mL) was added methyl iodide (31 mg, 0.22 mmoles), aqueous sodium hydroxide (1.0 mL, 2M) and tetrabutylammonium sulfate (44 mg, 0.13 mmoles). The solution was refluxed for one hour. After cooling to room temperature the dichloromethane was separated and evaporated. Ether was added to the residue and the white tetrabutylammonium iodide was removed by filtration. The ether was removed in vacuo to give the crude product compound 100 as a clear oil. The BOC group was removed by treatment with HCl in dioxane as described above to give the product as a white powder after lyophilization (17 mg, 42% yield).

$^1$H NMR (400 MHz) (CDCl$_3$) δ 1.23 (t, J=7.2 Hz, 3H), 2.27–2.33 (m, 4H), 2.85–2.91 (m, 4H), 3.26 (s, 3H), 4.15 (q, J=7.2 Hz, 2H), 6.78 (d, J=10 Hz, 1H), 6.85–6.89 (m, 2H), 7.05 (d, J=8.0 Hz, 2H), 7.14 (d, J=8.0 Hz, 2H) 7.19–7.23 (m, 1H).

EXAMPLE 60

Preparation of 4-[(1-benzylpiperidin-4-yl)-(3-fluorophenyl)-methyl]-phenyl-carbamic acid ethyl ester (compound 116)

The benzylation of compound 100 was performed on a small scale in parallel in test tubes (13 mm×100 mm). A typical procedure is outline below.

The free base form of compound 100 was obtained by addition of ammonium hydroxide (1M, 0.5 mL) to an aqueous solution of compound 100 (0.046 mmoles) and extracted into ether. The ether was removed in vacuo to give an oil which was dissolved in dichloromethane and treated with benzyl bromide (0.14 mL of 0.5 M in dichloromethane) and triethylamine (0.05 mL). The solution was stirred at room temperature for 5 hours. The solvent was removed in vacuo. The product was dissolved in water/acetonitrile/HCl (2:1:0.5 M) and lyophilized to give the product compound 108 as a white powder.

$^1$H NMR (400 MHz) (CDCl$_3$) δ 1.28 (t, J=7.2 Hz, 3H), 2.33–2.36 (m, 4H), 2.38–2.46 (m, 4H), 3.51 (s, 2H), 4.19 (q, J=7.2 Hz, 2H), 6.50 (s, 1H), 6.78 d, J=10 Hz, 1H), 6.85–6.89 (m, 2H), 7.05 (d, J=8.0 Hz, 2H), 7.19–7.30 (m, 7H).

EXAMPLES 61–68

The following compounds were also made by following the synthesis routes described in Schemes 8(a)–(c).

TABLE 1

| Example | Compound | Chemical structure | Characterization data [$^1$H NMR; 400 MHz (CDCl$_3$)] | Scheme |
|---------|----------|--------------------|--------------------------------------------------------|--------|
| 61 | 108 | 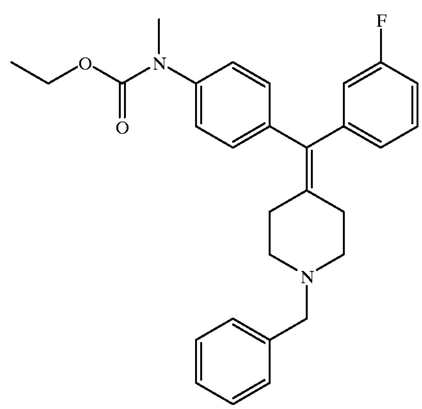 | δ 1.17(t, J=7.6Hz, 3H), 2.28–2.35(m, 4H), 2.40–2.45 (m, 4H), 3.21(s, 3H), 3.50(s, 2H), 4.10(q, J=7.2Hz, 2H), 6.73(d, J=8.7Hz, 1H), 6.85 (m, 2H), 7.01(d, J=8.8Hz, 2H), 7.2–7.3(m, 8H) | 8 (c) |
| 62 | 103 | 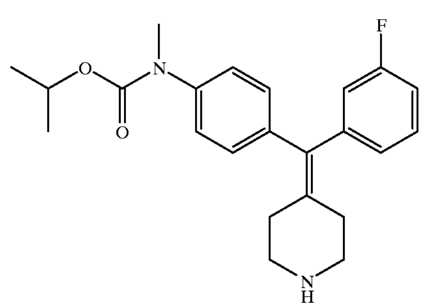 | δ 1.21(d, J=6.8Hz, 6H), 2.28(t, J=5.6Hz, 2H), 2.31 (t, J=5.6Hz, 2H), 2.88(t, J=5.6Hz, 4H), 3.25(s, 3H), 4.93(quin, J=6.0Hz, 1H), 6.78(d, 1H), 6.87(d, 2H), 7.04(d, 2H), 7.14(d, 2H), 7.15–7.29(m, 2H) | 8 (b) |

TABLE 1-continued

| Example | Compound | Chemical structure | Characterization data [¹H NMR; 400 MHz (CDCl₃)] | Scheme |
|---------|----------|--------------------|--------------------------------------------------|--------|
| 63 | 107 | 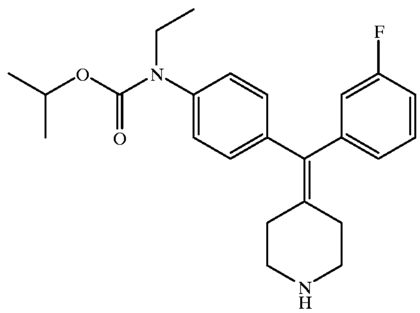 | δ 1.14(t, J=7.2Hz, 3H), 1.20(d, J=6.4Hz, 6H), 2.92 (t, J=5.2Hz, 2H), 2.33(t, J=5.2Hz, 2H), 2.90(t, J=5.2 Hz, 4H), 3.66(q, J=7.6Hz), 2H), 4.93(quin, J=6.0Hz, 1H), 6.79(d, 1H), 6.88(d, 2H), 7.02(d, 2H), 7.15(d, 2H), 7.18–7.25(m, 2H) | 8 (b) |
| 64 | 102 | 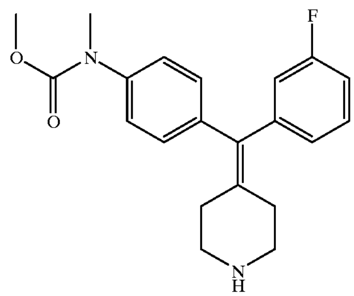 | δ 2.27–2.33(m, 4H), 2.88– 2.90(m, 4H), 3.27(s, 3H), 3.70(s, 3H), 6.79(d, 10Hz, 1H), 6.88–6.90(m, 2H), 7.06 (d, J=8.4Hz, 2H), 7.13(d, J=8.4Hz, 2H), 7.20–7.25(m, 1H) | 8 (b) |
| 65 | 106 | 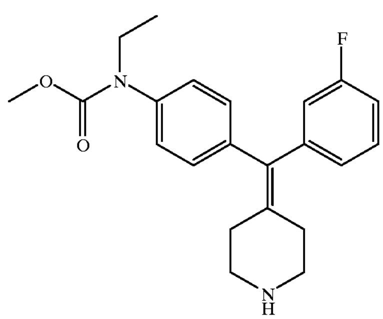 | δ 1.13(t, J=6.8Hz, 3H), 2.27–2.33(m, 4H), 2.88– 2.90(m, 4H), 3.67(s, 3H), 3.68(q, J=6.8Hz, 2H), 6.79 (d, 10Hz, 1H), 6.88–6.90 (m, 2H), 7.06(d, J=8.4Hz, 2H), 7.13(d, J=8.4Hz, 2H), 7.20–7.25(m, 1H) | 8 (b) |
| 66 | 104 | 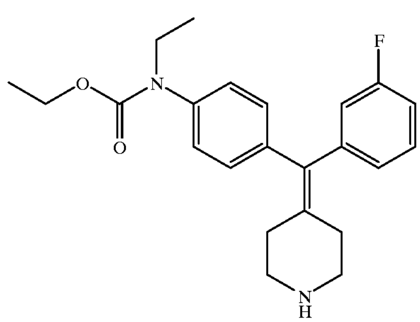 | δ 1.13(t, J=6.8Hz, 3H), 1.21(t, J=7.2Hz, 3H), 2.30–2.36(m, 4H), 2.91– 2.93(m, 4H), 3.67(q, J=6.8 Hz, 2H), 4.13(q, J=6.8Hz, 2H), 6.79(d, 10Hz, 1H), 6.88–6.90(m, 2H), 7.06(d, J=8.4Hz, 2H), 7.13(d, J=8.4Hz, 2H), 7.20–7.25 (m, 1H) | 8 (b) |

TABLE 1-continued

| Example | Compound | Chemical structure | Characterization data [$^1$H NMR; 400 MHz (CDCl$_3$)] | Scheme |
|---|---|---|---|---|
| 67 | 99 | 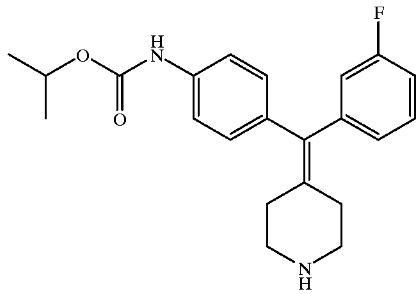 | δ 1.26(d, J=6.0Hz, 6H), 2.27–2.32(m, 4H), 2.87–2.89(m, 4H), 4.95–5.02(m, 1H), 6.56(s, 1H), 6.79(d, 10Hz, 1H), 6.88–6.90(m, 2H), 7.01(d, J=8.4Hz, 2H), 7.20–7.25(m, 1H), 7.27(d, J=8.4Hz, 2H) | 8 (b) |
| 68 | 98 | 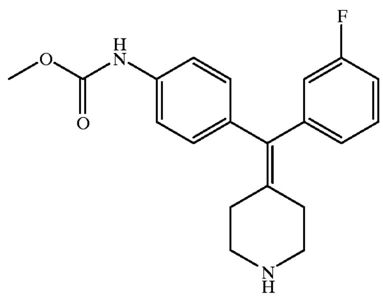 | δ 2.27–2.31(m, 4H), 2.86–2.89(m, 4H), 3.75(s, 3H), 6.64(s, 1H), 6.76–6.80(m, 1H), 6.85–7.00(m, 2H), 7.02(d, J=8.8Hz, 2H), 7.18–7.22(m, 1H), 7.28(d, J=8.8Hz, 2H) | 8 (b) |

The best mode of performing the invention known at present, is to use the compounds 6, 7, 9, 10, 12, 26.27, 34, 39, 44, 58, 59, 62, 69, 71, 104, 106, and 109.

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc.

Preferred pharmaceutically acceptable salts are the hydrochlorides and citrates.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

BIOLOGICAL EVALUATION

A) IN VITRO MODEL

Cell Culture

Human 293S cells expressing cloned human $\mu$, $\delta$, and $\kappa$ receptors and neomycin resistance were grown in suspension at 37° C. and 5% $CO_2$ in shaker flasks containing calcium-free DMEM 10% FBS, 5% BCS, 0.1% Pluronic F-68, and 600 $\mu$g/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l (for $\mu$g protein, see Table 1) were added to iced 12×75 mm polypropylene tubes containing 100 $\mu$l of the appropriate radioligand (see Table 1) and 100 $\mu$l of test peptides at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 $\mu$l MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves.

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are feasable). The specific radioligand binding was expressed as pmole/mg membrane protein. Values of $K_\delta$ and $B_{max}$ from individual experiments were obtained from non-linear fits of specifically bound (B) vs. nM free (F) radioligand from individual according to a one-site model.

B) BIOLOGICAL MODEL (IN VIVO MODEL)

FREUND'S COMPLETE ADJUVANT (FCA), AND SCIATIC NERVE CUFF INDUCED MECHANO-ALLODYNIA IN RAT

Animals

Male Sprague-Dawley rats (Charles River, St-Constant, Canada) weighing 175–200 g at the as time of surgery were used. They were housed in groups of three in rooms thermostatically maintained at 20° C. with a 12:12 hr light/dark cycle, and with free access to food and water. After arrival, the animals were allowed to acclimatize for at least 2 days before surgery. The experiments were approved by the appropriate Medical Ethical Committee for animal studies.

EXPERIMENTAL PROCEDURE

FREUND'S COMPLETE ADJUVANT

The rats were first anesthetized in a Halothane chamber after which 10 $\mu$l of FCA was injected s.c. into the dorsal region of the left foot, between the second and third external digits. The animals were then allowed to recover from anesthesia under observation in their home cage.

SCIATIC NERVE CUFF

The animals were prepared according to the method described by Mosconi and Kruger (1996). Rats were anesthetized with a mixture of Ketamine/Xylazine i.p. (2 ml/kg) and placed on their right side and an incision made over, and along the axis of, the lateral aspect of the left femur. The muscles of the upper quadriceps were teased apart to reveal the sciatic nerve on which a plastic cuff (PE-60 tubing, 2 mm long) was placed around. The wound was then closed in two layers with 3–0 vicryl and silk sutures.

DETERMINATION OF MECHANO-ALLODYNIA USING VON FREY TESTING

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill, USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

TESTING PROTOCOL

The animals were tested on postoperative day 1 for the FCA-treated group and on post-operative day 7 for the Sciatic Nerve Cuff group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

% MPE=Drug treated threshold (g)—allodynia threshold (g)×100
Control threshold (g)—allodynia threshold (g)

ADMINISTRATION OF TEST SUBSTANCE

Rats were injected (subcutaneously, intraperitoneally, or orally) with a test substance prior to von Frey testing, the time between administration of test compound and the von Frey test varied depending upon the nature of the test compound.

Definitions:
The following abbreviations have the indicated meanings:
Ac=acetyl
Ar=aryl
t-BOC=tertiary-butoxycarbonyl
t-Bu=tertiary-butyl
Et=ethyl
iPr=isopropyl
to Me=methyl
Ph=phenyl
Pr=propyl
r.t.=room temperature
TFA=trifluoroacetic acid
THF=tetrahydrofuran
TMEDA=N,N,N',N'-tetramethylethylenediamine

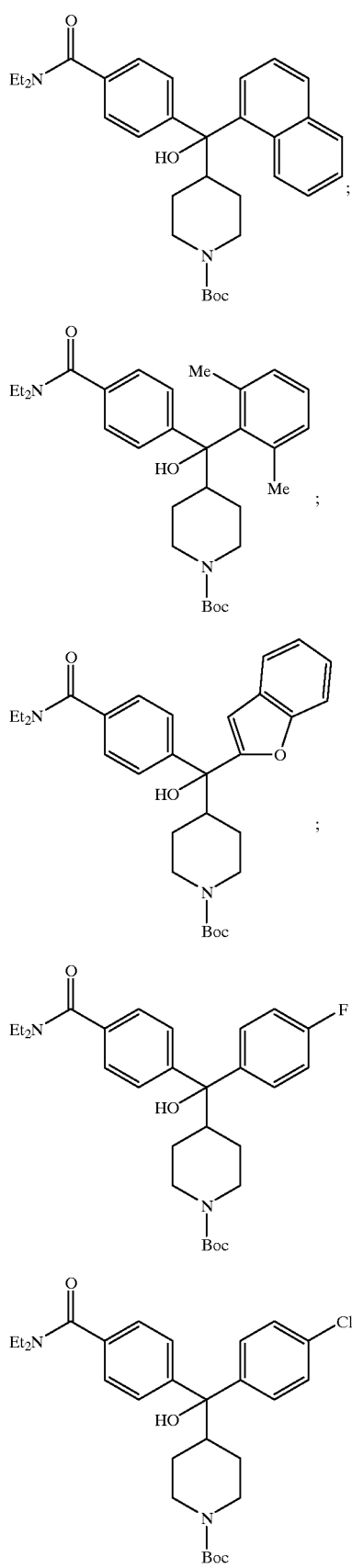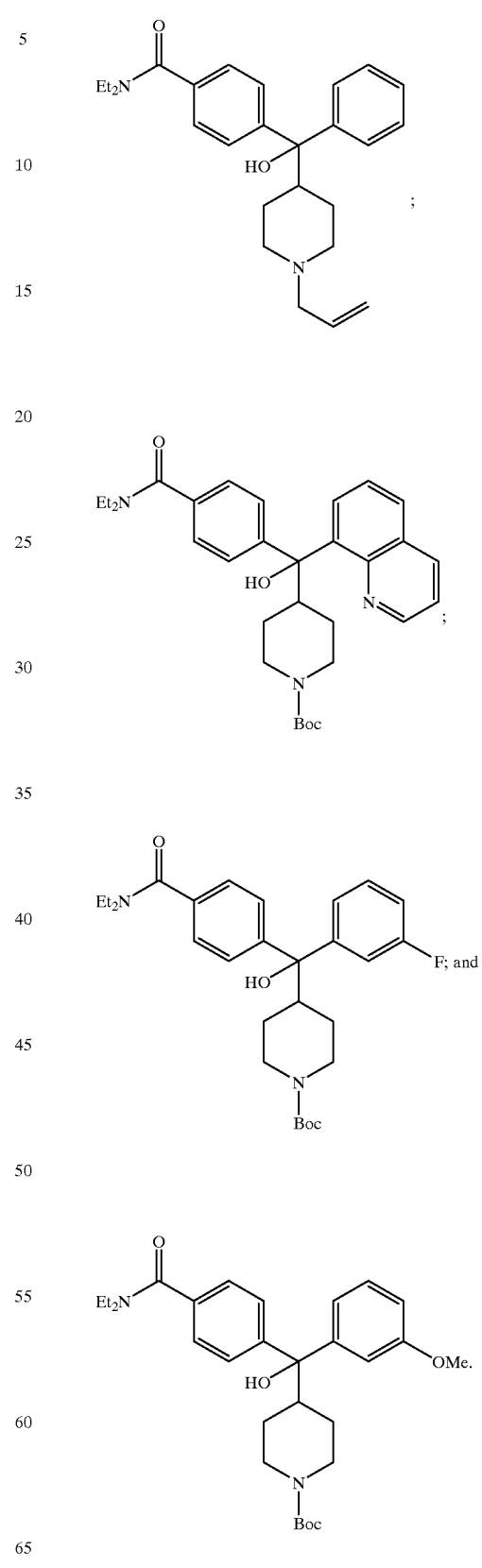

What is claimed is:
1. A compound of the general formula (I)

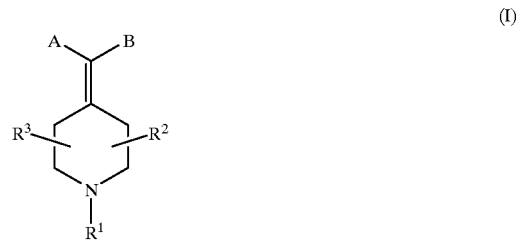

(I)

wherein:

$R^1$ is selected from hydrogen, a branched or straight $C_1$–$C_6$ alkyl, $C_1$–$C_6$ alkenyl, $C_3$–$C_8$ cycloalkyl, $C_4$–$C_8$ (alkyl-cycloalkyl) wherein alkyl is $C_1$–$C_2$ alkyl and cycloalkyl is $C_3$–$C_6$ cycloalkyl;

$C_6$–$C_{10}$ aryl; or heteroaryl having from 5 to 10 atoms selected from any of C, S, N and O;

wherein the aryl and heteroaryl may optionally and independently be substituted by 1 or 2 substituents independently selected from any of hydrogen, $CH_3$, —$(CH_2)_pCF_3$, halogen, —$CONR^5R^4$, —$COOR^5$, —$COR^5$, —$(CH_2)_pNR^5R^4$, —$(CH_2)_pCH_3(CH_2)_pSOR^5R^4$, —$(CH_2)_pSO_2R^5$, and —$(CH_2)_pSO_2NR^5$, wherein $R^4$ and $R^5$ are each and independently as defined for $R^1$ above and p is 0, 1 or 2;

($C_1$–$C_2$ alkyl)-$C_6$–$C_{10}$ aryl); or ($C_1$–$C_2$ alkyl)heteroaryl, the heteroarylmoieties having from 5 to 10 atoms selected from any of C, S, N and O, and where the aryl or heteroaryl may optionally and independently be substituted by 1 or 2 substituents independently selected from any of hydrogen, $CH_3$, —$(CH_2)_qCF_3$, halogen, —$CONR^5R^4$, —$COOR^5$, —$COR^5$, —$(CH_2)_qNR^5R^4$, —$(CH_2)_qCH_3(CH_2)_qSOR^5R^4$, —$(CH_2)_qSO_2R^5$, —$(CH_2)_qSO_2NR^5$ and —$(CH_2)_pOR^5$, wherein $R^4$ and $R^5$ are each and independently as defined for $R^1$ above and q is 0, 1 or 2; and

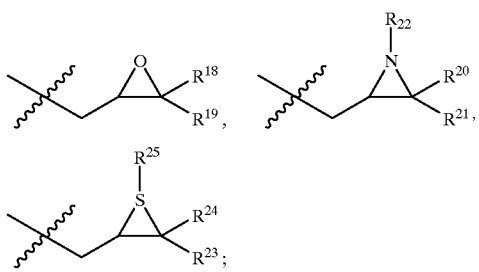

wherein $R^{18}$, $R^{19}$, $R^{20}$, $R^{21}$, $R^{22}$, $R^{23}$, $R^{24}$ and $R^{25}$ are each and independently hydrogen, $C_1$–$C_6$ alkyl or $C_1$–$C_6$ alkenyl;

$R^2$ and $R^3$ are each and independently hydrogen or $C_1$–$C_6$ alkyl;

A is selected from

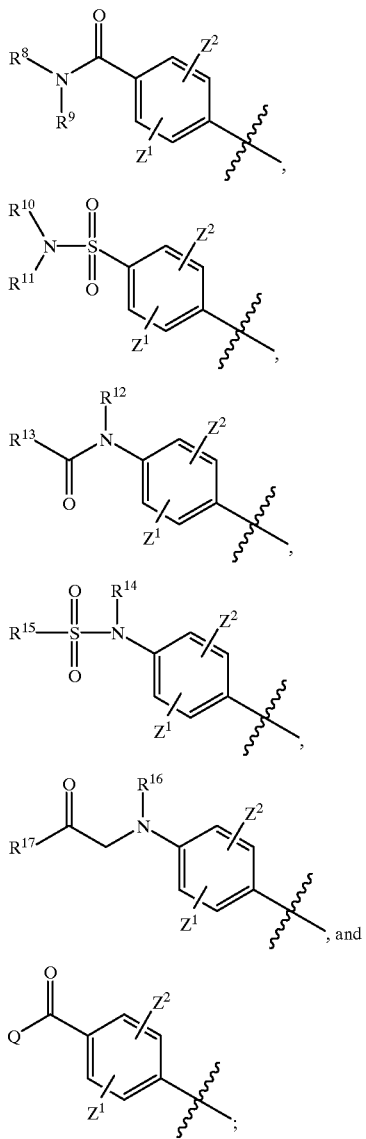

wherein $R^8, R^9, R^{10}, R^{11}, R^{12}, R^{13}, R^{14}, R^{15}, R^{16}$ and $R^{17}$ are each and independently as defined for $R^1$ above, and where in the phenyl ring of each A substituent maybe optionally and independently substituted at any position of the phenyl ring by 1 or 2 substituents $Z^1$ and $Z^2$ which are each and independently selected from hydrogen, $CH_3$, $-(CH_2)_qCF_3$, halogen, $CONR^6R^7$, $-COOR^6$, $-COR^6$, $-(CH_2)_rNR^6R^7$, $-(CH_2)_rCH_3$ $(CH_2)_rSOR^6$, $-(CH_2)_rSO_2R^6$ and $-(CH_2)_rSO_2NR^6R^7$ wherein $R^6$ and $R^7$ are each and independently as defined for $R^1$ above and r is 0, 1, or 2;

Q is a $C_5$–$C_6$ hydroaryl or heterohydroaromatic having 5 or 6 atoms selected from any one of C, S, N and O; $C_5$–$C_6$ cycloalkyl, or heterocycloalkyl having 5 or 6 atoms selected from any one of C, N, O and S; and where each Q may optionally be substituted by a substituent $Z^1$ and $Z^2$ as defined above;

B is a substituted or unsubstituted aromatic, heteroaromatic, hydroaromatic or heterohydroaromatic moiety having from 5 to 10 atoms selected from any of C, S, N and O, optionally and independently substituted by 1 or 2 substituents independently selected from hydrogen, $CH_3$, $-(CH_2)_tCF_3$, halogen, $-(CH_2)_tCONR^5R^4$, $-(CH_2)_tNR^5R^4$, $-(CH_2)_tCOR^5$, $-(CH_2)_tCOOR^5$, $-OR^5$, $-(CH_2)_tSOR^5$, $-(CH_2)_tSO_2R^5$, and $-(CH_2)_tSO_2NR^5R^4$, wherein $R^4$ and $R^5$ are each and independently as defined for $R^1$ above, and t is 0, 1, 2 or 3;

$R^4$ and $R^5$ are each and independently as defined for $R^1$ above;

as well as pharmaceutically acceptable salts of the compounds of the formula (I), and isomers, hydrates, isoforms and prodrugs thereof with the proviso that:
when A is:

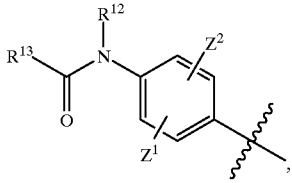

$R_1$ is H;
$R_{12}$ is $CH_3$
and $R_{13}$ is a $C_1$–$C_2$ alkyl,
then B is not an unsubstituted phenyl.

2. A compound of the formula (I) according to claim 1, wherein

A is selected from

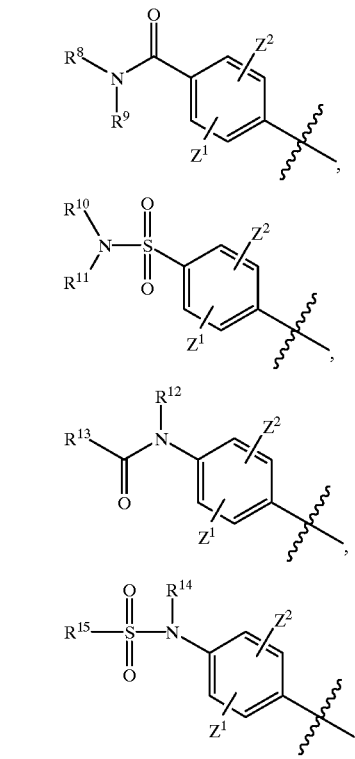

-continued

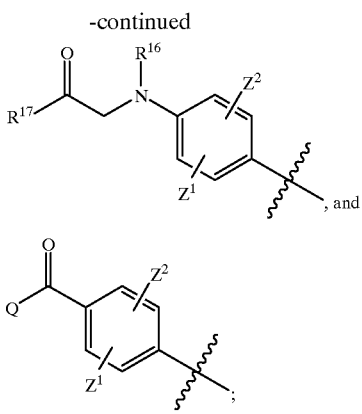, and;

wherein $R^8$, $R^9$, $R^{10}$, $R^{11}$, $R^{12}$, $R^{13}$, $R^{14}$, $R^{15}$, $R^{16}$ and $R^{17}$ is each and independently as defined for $R^1$ above, and wherein the phenyl ring of each A substituent may be optionally and independently substituted at any position of the phenyl ring by 1 or 2 substituents $Z^1$ and $Z^2$ which are each and independently selected from hydrogen, $CH_3$, —$(CH_2)_qCF_3$, halogen, —$CONR^6R^7$, —$COOR^6$, —$COR^6$, —$(CH_2)_rNR^6R^7$, —$(CH_2)_rCH_3(CH_2)_rSOR^6$, —$(CH_2)_rSO_2R^6$ and —$(CH_2)_rSO_2NR^6R^7$ wherein $R^6$ and $R^7$ is each and independently as defined for $R^1$ above, and r is 0, 1, or 2;

Q is selected from morpholine, piperidine and pyrrolidine;

$R^1$, $R^4$, and $R^5$ is each and independently selected from hydrogen, a branched or straight $C_1$–$C_4$ alkyl, $C_3$–$C_5$ cycloalkyl, $C_4$–$C_8$ (alkyl-cycloalkyl) wherein alkyl is $C_1$–$C_2$ alkyl and cycloalkyl is $C_3$–$C_6$ cycloalkyl; $C_6$–$C_{10}$ aryl; and heteroaryl having from 5 to 6 atoms selected from any of C, S, N and O; and where the aryl or heteroaryl may optionally and independently be substituted by 1 or 2 substituents independently selected from any of hydrogen, $CH_3$, —$(CH_2)_pCF_3$, halogen, —$CONR^5R^4$, —$COOR^5$, —$COR^5$, —$(CH_2)_pNR^5R^4$, —$(CH_2)_pCH_3(CH_2)_pSOR^5R^4$, —$(CH_2)_pSO_2R^5$, and —$(CH_2)_pSO_2NR^5$, wherein $R^4$ and $R^5$ is each and independently as defined for $R^1$ above and p is 0, 1 or 2;

B is selected from phenyl, naphthyl, indolyl, benzofuranyl, dihydrobenzofuranyl, benzothiophenyl, pyrryl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, pyrrolidinyl, and indazolinyl, each optionally and independently substituted by 1 or 2 substituents independently selected from hydrogen, $CH_3$, $CF_3$, halogen, —$(CH_2)_qCONR^5R^4$, —$(CH_2)_qNR^5R^4$, —$(CH_2)_qCOR^5$, —$(CH_2)_qCO_2R^5$, and —$OR^5$, wherein q is 0 or 1, and wherein $R^4$ and $R^5$ are as defined above;

$R^2$ and $R^3$ is each and independently hydrogen or methyl.

3. A compound of the formula (I) according to claim 2, wherein

A is

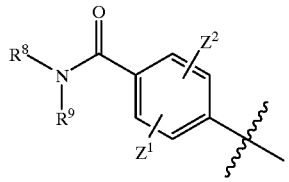

wherein $R^8$ and $R^9$ are both ethyl, and where the phenyl ring optionally and independently may be substituted at any position of the phenyl ring by 1 or 2 substituents $Z^1$ and $Z^2$ which are each and independently selected from hydrogen, $CH_3$, —$(CH_2)_qCF_3$, halogen, —$CONR^6R^7$, —$COOR^6$, —$COR^6$, —$(CH_2)_rNR^6R^7$, —$(CH_2)_rCH_3(CH_2)_rSOR^6$, —$(CH_2)_rSO_2R^6$ and —$(CH_2)_rSO_2NR^6R^7$ wherein $R^6$ and $R^7$ is each and independently as defined for $R^1$ above and r is 0, 1, or 2;

$R^1$ is selected from hydrogen, methyl, ethyl, —$CH_2CH=CH_2$, —$CH_2$-cyclopropyl, —$CH_2$-aryl, or $CH_2$-heteroaryl, the heteroaryl moieties having from 5 to 6 atoms selected from any of C, S, N and O;

B is selected from phenyl, naphthyl, indolyl, benzofuranyl, dihydrobenzofuranyl, benzothiophenyl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, and indazolinyl, each optionally and independently substituted by 1 or 2 substituents independently selected from hydrogen, $CH_3$, $CF_3$, halogen, —$(CH_2)_qCONR^5R^4$, —$(CH_2)_qNR^5R^4$, —$(CH_2)_qCOR^5$, —$(CH_2)_qCO_2R^5$, and —$OR^5$, wherein q is 0 or 1, and wherein $R^4$ and $R^5$ are as defined above; and $R^2$ and $R^3$ is each and independently hydrogen or methyl.

4. A compound of the formula (I) according to claim 1, which compound is any of

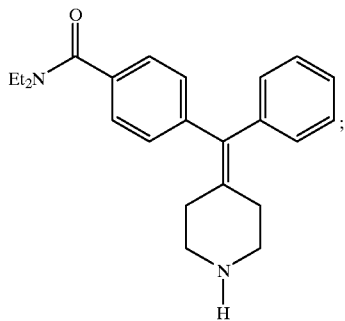;

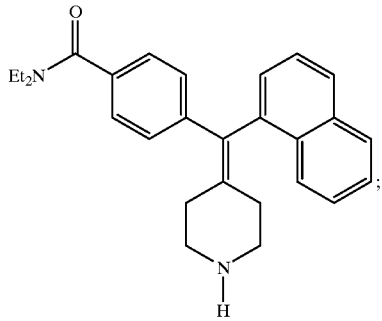;

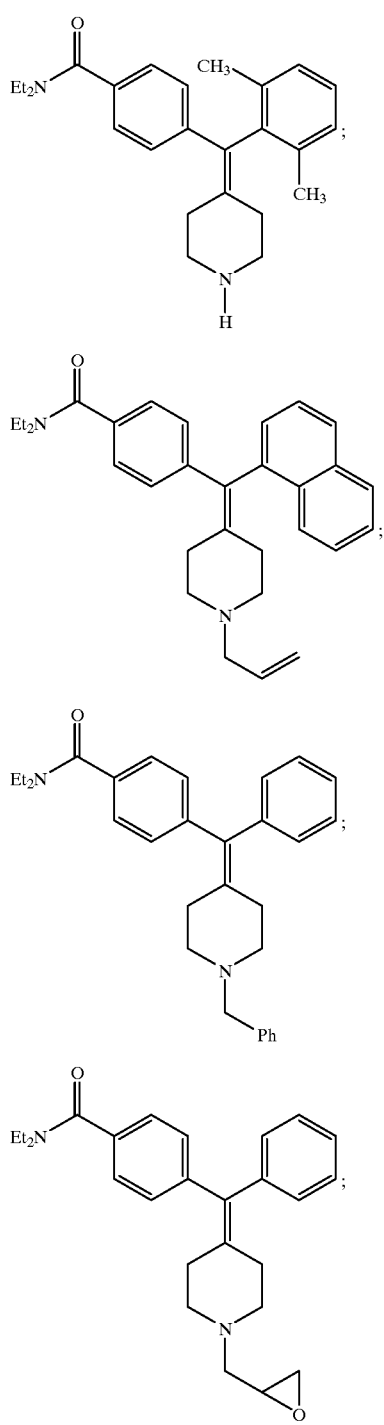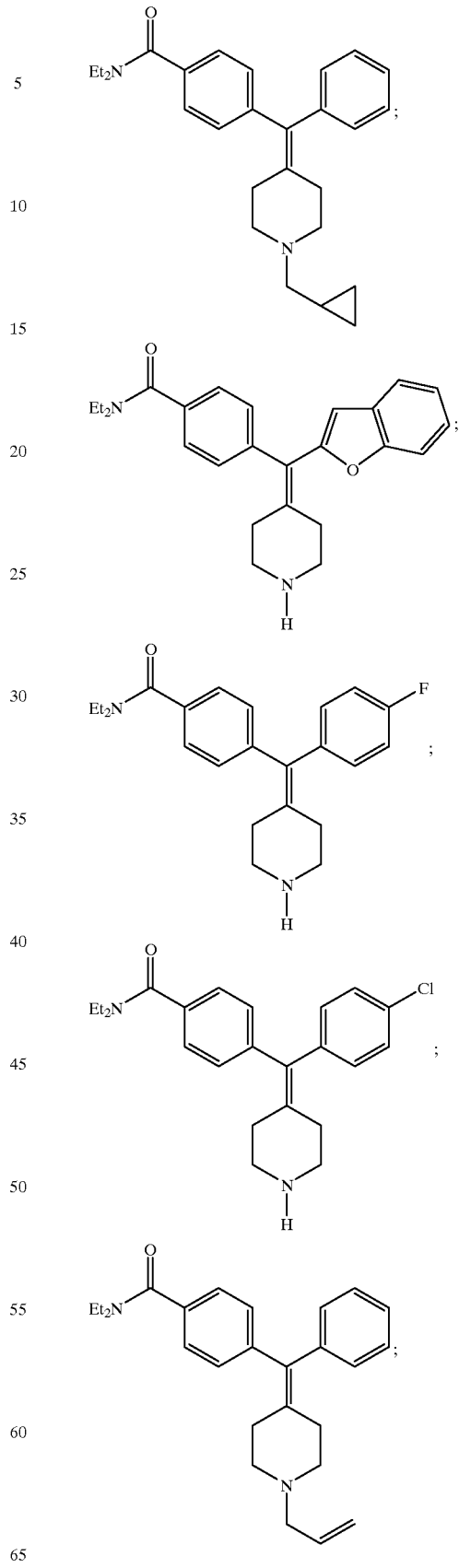

-continued
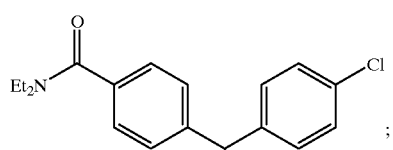
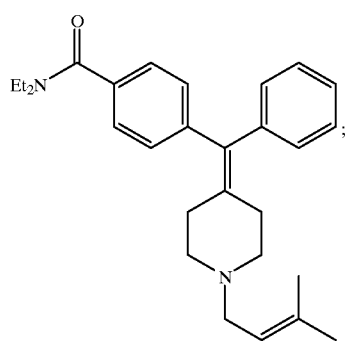
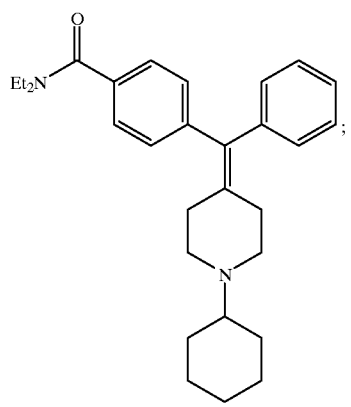
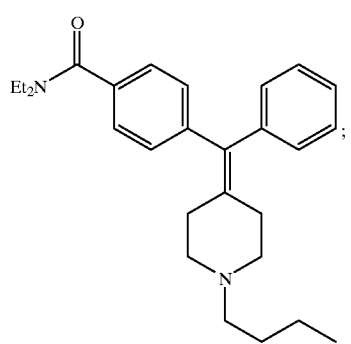
-continued
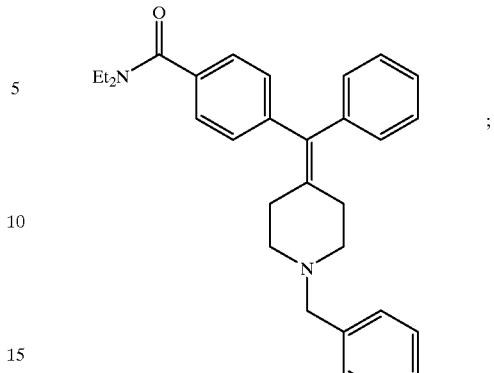
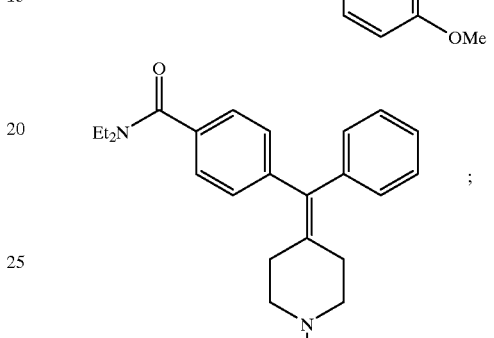
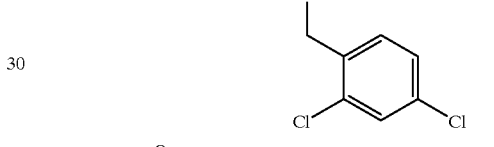
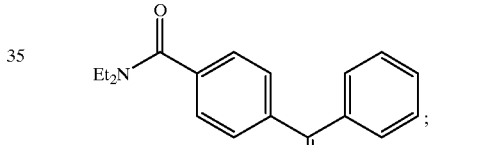

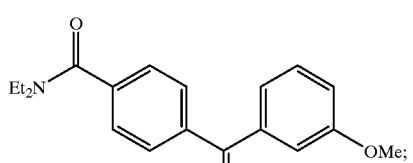
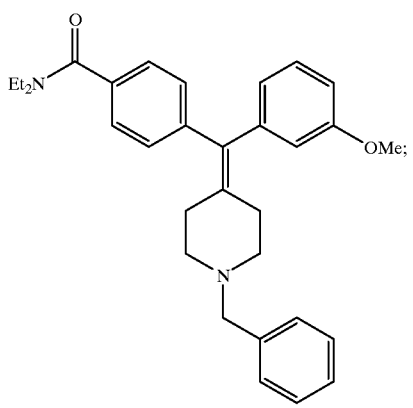
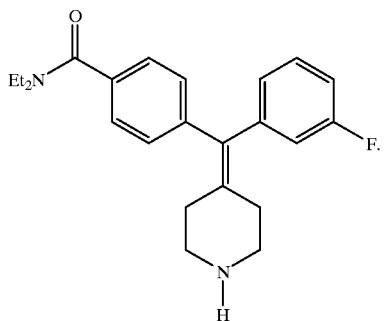
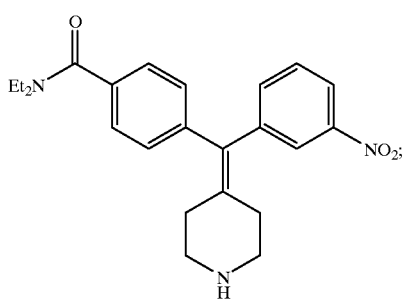
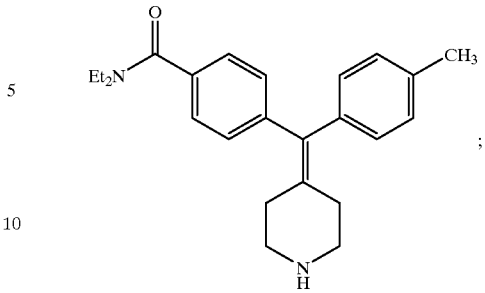
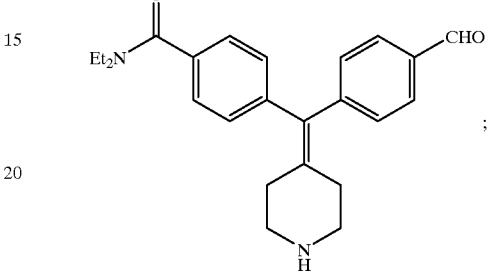
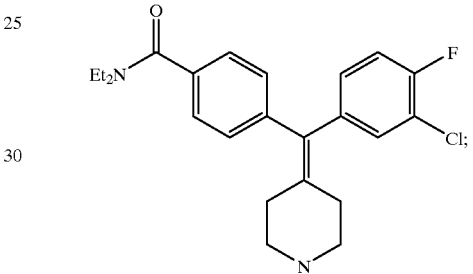
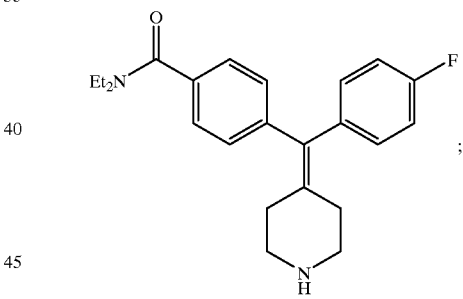
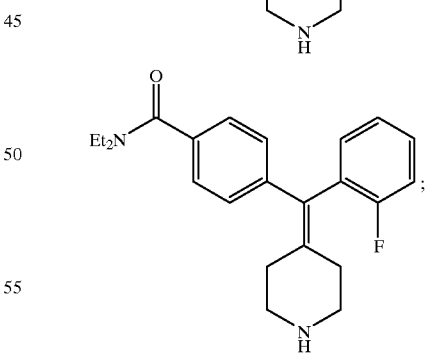

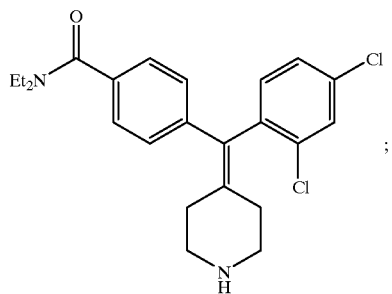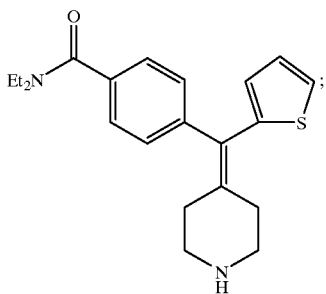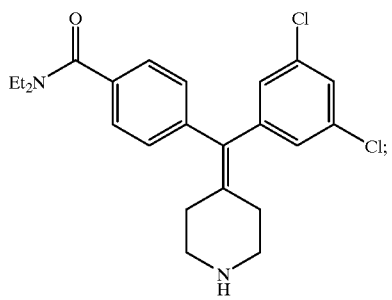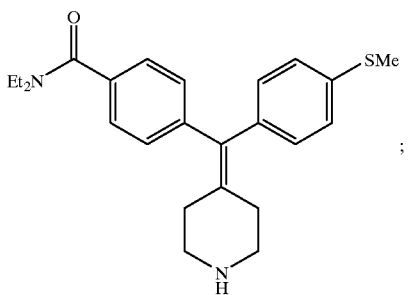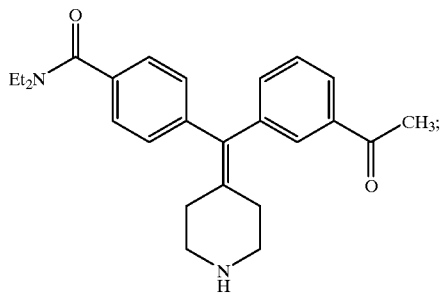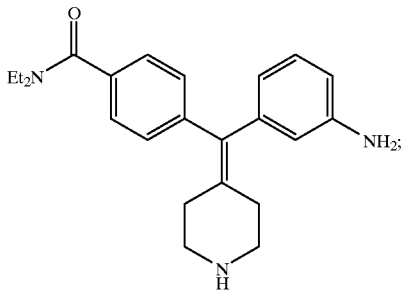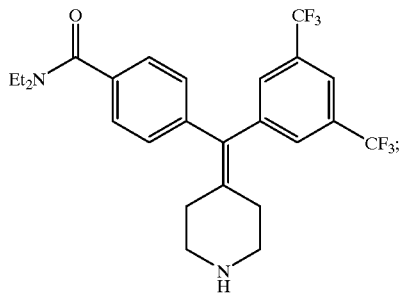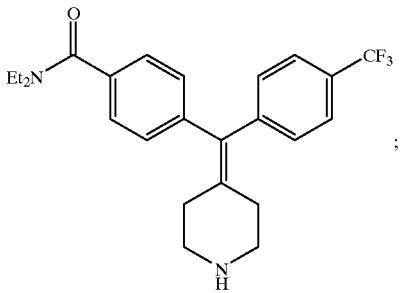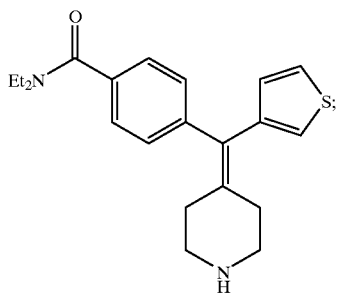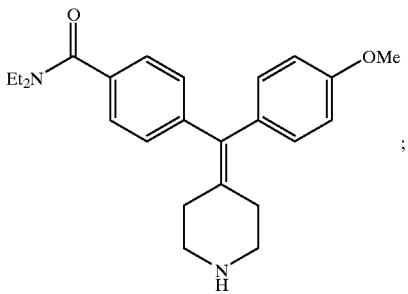

-continued
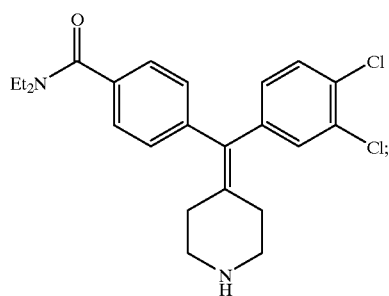
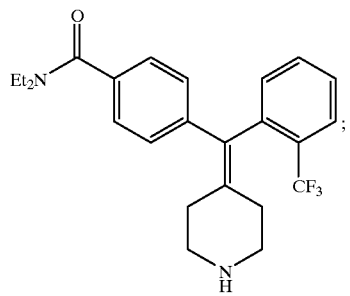
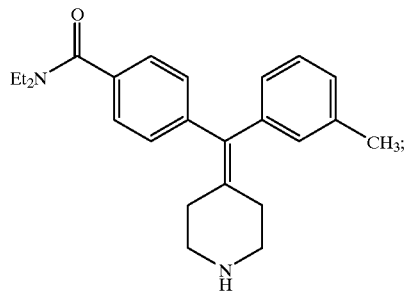
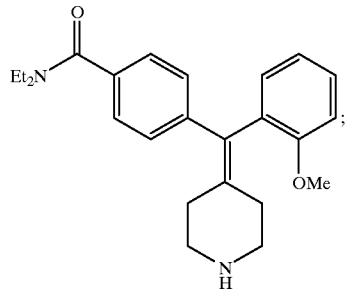
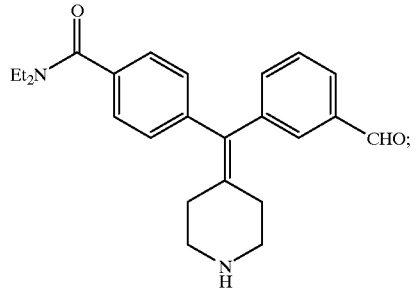
-continued
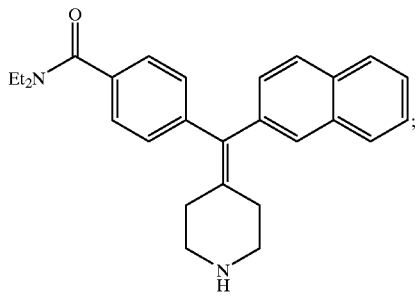
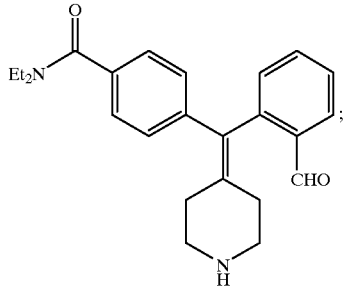
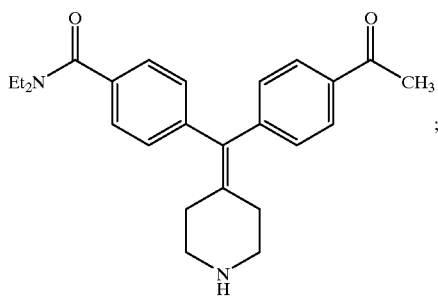
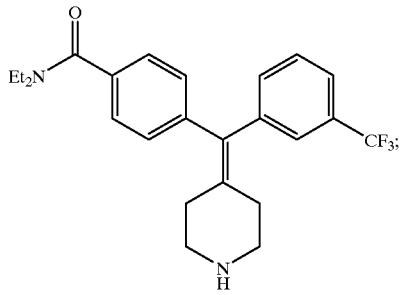
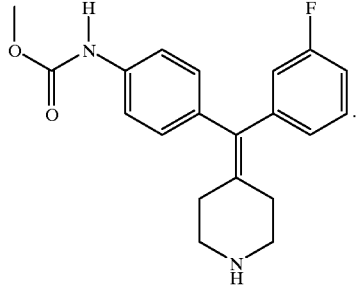

wherein R is morpholine, piperidine or pyrrolidine;
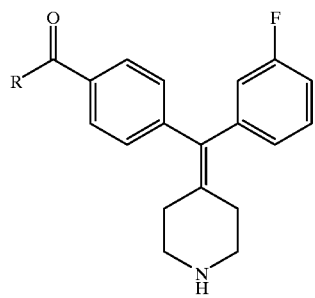
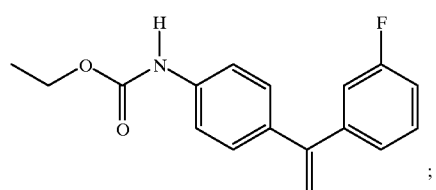
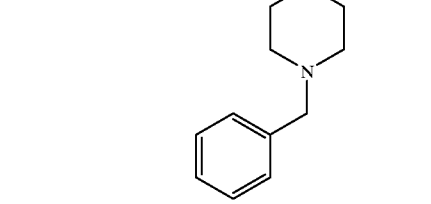
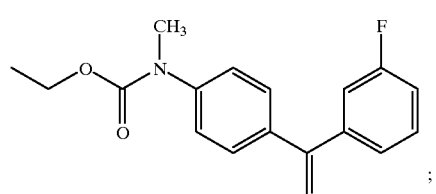
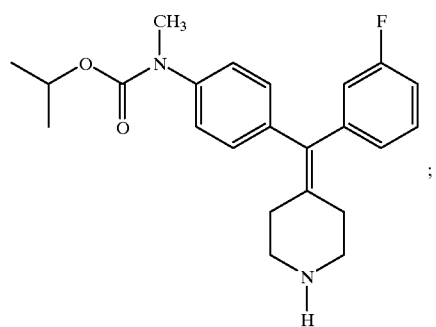
-continued
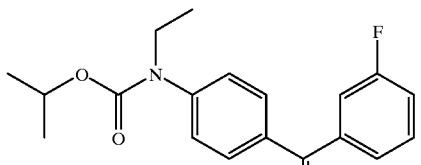
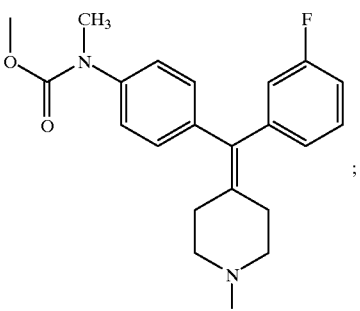
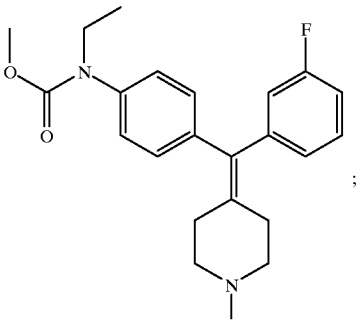
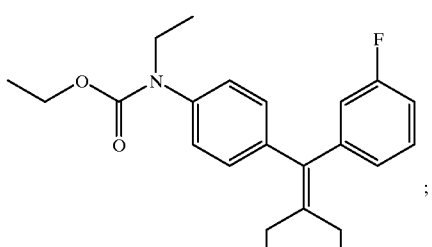
; and
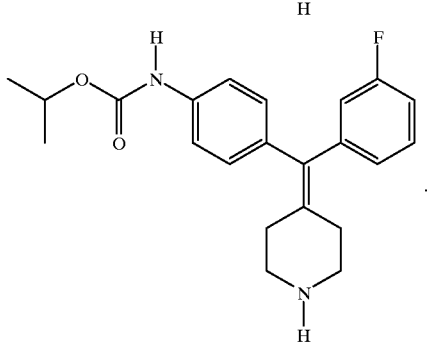

5. A compound according to claim 1, which is selected from

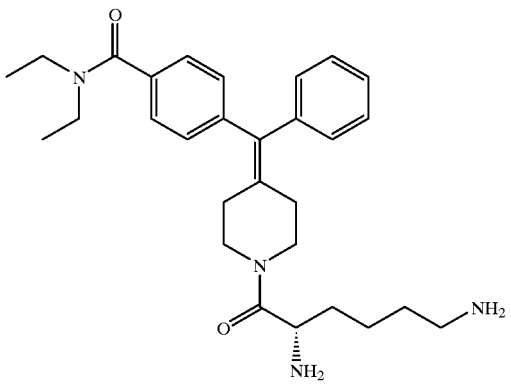

and

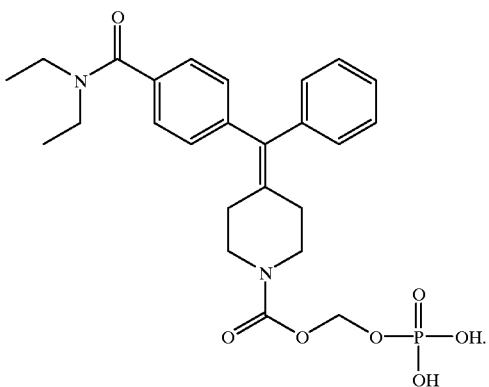

6. A compound according to any one of the preceding claims, in form of a hydrochloride, sulfate, tartrate or citrate salt.

7. An isotopically labelled compound of claim 1.

8. A pharmaceutical composition comprising a therapeutically effective amount of a compound according to claim 1 as an active ingredient, together with a pharmacologically and pharmaceutically acceptable carrier.

9. A method of treating a patient for pain, comprising administering an analgesically effective amount of a compound according to claim 1 to said patient.

10. A method of treating a patient for a spinal injury, comprising administering anopiod receptor antagonistic effective amount of a compound according to claim 1 to said patient.

11. A process for the preparation of a compound of the formula (I) according to claim 1, comprising a) reacting a ketone of the formula (l)

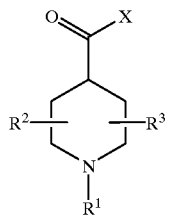

(l)

wherein $R^1$, $R^2$ and $R^3$ are as defined in formula (I) of claim 1, and X is a leaving group, is reacted with an organometallic reagent of the formula (j) or (k)

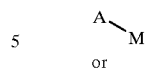

(j)

or

(k)

wherein A and B are as defined in formula (I) of claim 1, and M is a metal group; and wherein the reaction is optionally performed in the presence of a solvent, giving a compound of the formula (h)

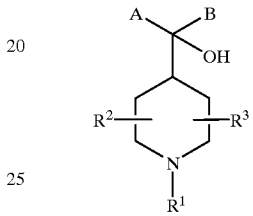

(h)

wherein A, B, $R^1$, $R^2$ and $R^3$ are as defined in formula (I) of claim 1, and wherein R1 also may be tert-butoxycarbonyl;

b) the compound of the formula (h) is dehydrated, giving a compound of the formula (l) of claim 1.

12. A compound of the formula

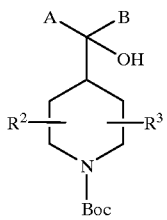

(h)

wherein A, B, $R^2$ and $R^3$ are as defined in claim 1.

13. A compound of the formula (h) according to step a) of claim 1, wherein

A is

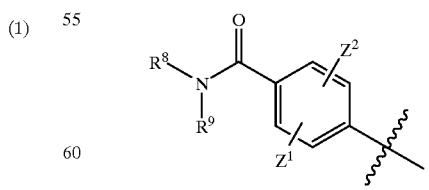

wherein $R^8$ and $R^9$ are both an ethyl group, and $Z^1$ and $Z^2$ are as defined in claim 1.

14. A compound according to claim 13, which compound is any of